US012595507B2

(12) United States Patent
Rudi et al.

(10) Patent No.: US 12,595,507 B2
(45) Date of Patent: Apr. 7, 2026

(54) METHOD FOR PREVENTING FALSE POSITIVES IN METHODS EMPLOYING DDNTP'S

(71) Applicants: NORWEGIAN UNIVERSITY OF LIFE SCIENCES, Ås (NO); HEDMARK UNIVERSITY OF APPLIED SCIENCES, Hamar (NO)

(72) Inventors: Knut Rudi, Ås (NO); Robert C. Wilson, Hamar (NO)

(73) Assignees: Norwegian University of Life Sciences, Ås (NO); Inland Norway University of Applied Sciences, Elverum (NO)

( * ) Notice: Subject to any disclaimer, the term of this patent is extended or adjusted under 35 U.S.C. 154(b) by 0 days.

(21) Appl. No.: 15/545,522

(22) PCT Filed: Feb. 1, 2016

(86) PCT No.: PCT/EP2016/052092

§ 371 (c)(1),
(2) Date: Jul. 21, 2017

(87) PCT Pub. No.: WO2016/120494

PCT Pub. Date: Aug. 4, 2016

(65) Prior Publication Data

US 2017/0369941 A1 Dec. 28, 2017

(30) Foreign Application Priority Data

Jan. 30, 2015 (GB) ...................................... 1501603

(51) Int. Cl.

*C12Q 1/6869* (2018.01)
*C12Q 1/6816* (2018.01)
*C12Q 1/6818* (2018.01)
*C12Q 1/6848* (2018.01)

(52) U.S. Cl.

CPC ......... *C12Q 1/6869* (2013.01); *C12Q 1/6816* (2013.01); *C12Q 1/6818* (2013.01); *C12Q 1/6848* (2013.01)

(58) Field of Classification Search

CPC .. C12Q 1/6869; C12Q 1/6816; C12Q 1/6818; C12Q 1/6848

See application file for complete search history.

(56) References Cited

U.S. PATENT DOCUMENTS

| | | | | |
|---|---|---|---|---|
| 5,102,785 | A * | 4/1992 | Livak | C12Q 1/6869 435/6.12 |
| 6,258,568 | B1 | 7/2001 | Nyren | |
| 6,682,887 | B1 | 1/2004 | Singh | |
| 2002/0015962 | A1 | 2/2002 | Nolan et al. | |
| 2002/0106653 | A1 | 8/2002 | Kurane et al. | |
| 2002/0187477 | A1 | 12/2002 | Xue et al. | |
| 2006/0281099 | A1 | 12/2006 | Breneman et al. | |
| 2007/0275377 | A1 | 11/2007 | Golz et al. | |
| 2009/0203085 | A1 * | 8/2009 | Kurn | C12Q 1/686 435/91.2 |
| 2009/0305249 | A1 | 12/2009 | Anderson et al. | |
| 2014/0272978 | A1 * | 9/2014 | Shi | C12Q 1/6869 435/6.11 |

FOREIGN PATENT DOCUMENTS

| | | | |
|---|---|---|---|
| CN | 1354261 | 6/2002 | |
| EP | 1 389 638 | 2/2004 | |
| EP | 2 439 283 | 4/2012 | |
| GB | 2485275 | 5/2012 | |
| JP | 2002-191372 | 7/2002 | |
| JP | 2003-189899 | 7/2003 | |
| JP | 2005-525797 | 9/2005 | |
| JP | 2007-527708 | 10/2007 | |
| JP | 2012-10666 | 1/2012 | |
| RU | 2 451 086 | 12/2010 | |
| WO | 99/50448 | 10/1999 | |
| WO | 99/53316 | 10/1999 | |
| WO | 00/55372 | 9/2000 | |
| WO | 03/066667 | 8/2003 | |
| WO | 2005/001124 | 1/2005 | |
| WO | 2005/061734 | 7/2005 | |
| WO | 2006/107881 | 10/2006 | |
| WO | WO-2006107881 A2 * | 10/2006 | C12N 5/1006 |
| WO | 2012/009813 | 1/2012 | |
| WO | 2012/024642 | 2/2012 | |
| WO | 2012/049279 | 4/2012 | |
| WO | 2012/095639 | 7/2012 | |
| WO | WO-2013056651 A1 * | 4/2013 | C12Q 1/6818 |
| WO | 2013/116780 | 8/2013 | |
| WO | 2016/101959 | 6/2016 | |

OTHER PUBLICATIONS

Cordeiro (Journal of Biotechnology(2013) vol. 168, pp. 90-94).*
Chen ( The pharmacogenomics Journal (2003) vol. 3, pp. 77-96).*
Bernard ( Rapid Cycle—Real-time PCR (2001) pp. 11-19).*
Schrader (Journal of applied microbiology (2012) vol. 113,pp. 1014-1026).*

(Continued)

*Primary Examiner* — Anne M. Gussow
(74) *Attorney, Agent, or Firm* — Wenderoth, Lind & Ponack, L.L.P.

(57) ABSTRACT

The present invention relates to a method which prevents undesirable binding of ddNTPs to double stranded polynucleotides when in the presence of a polymerase. Such methods may be used to prevent the appearance of false positives in methods employing ddNTPs, e.g. in sequence detection methods. The present invention also provides a method of avoiding a false Tm reading or false FRET effects (such as false positive quenching), for example in a melting curve analysis method. In particular a method is provided in which a target nucleotide sequence in a test polynucleotide is detected using a method in which a double stranded molecule is generated which may or may not comprise two labels depending on whether the target sequence is present in which the presence of the two labels is determined, preferably by performing a melting curve analysis.

18 Claims, 16 Drawing Sheets

Specification includes a Sequence Listing.

(56) References Cited

OTHER PUBLICATIONS

Wilson (ACS Nano(2009) vol. 3, pp. 955-1003).*
Miyata (J Biochem (1982) vol. 92, pp. 1539-1546).*
Chen, X. and Sullivan, P.F., 2003. Single nucleotide polymorphism genotyping: biochemistry, protocol, cost and throughput. The pharmacogenomics journal, 3(2), pp. 77-96. (Year: 2003).*
Bernard, P.S., Reiser, A. and Pritham, G.H., 2001. Mutation detection by fluorescent hybridization probe melting curves. In Rapid Cycle Real-Time PCR: Methods and Applications (pp. 11-19). Berlin, Heidelberg: Springer Berlin Heidelberg. (Year: 2001).*
Miyata, S. and Kihara, H.K., 1982. Properties of a DNA-Binding Protein in a Culture Medium of Thymus Cells. The Journal of Biochemistry, 92(5), pp. 1539-1546. (Year: 1982).*
Wilson, N.A., Abu-Shumays, R., Gyarfas, B., Wang, H., Lieberman, K.R., Akeson, M. and Dunbar, W.B., 2009. Electronic control of DNA polymerase binding and unbinding to single DNA molecules. Acs Nano, 3(4), pp. 995-1003. (Year: 2009).*
Rudi et al., "Real-time closed tube single nucleotide polymorphism (SNP) quantification in pooled samples by quencher extension (QEXT)", Nucleic Acids Research, 31(19): el17, pp. 1-5 (2003).
International Search Report and Written Opinion of the International Searching Authority, issued Apr. 18, 2016 in corresponding International Application No. PCT/EP2016/052092.
Clark, "Novel non-templated nucleotide addition reactions catalyzed by procaryotic and eucaryotic DNA polymerases", Nucleic Acid Research, vol. 16, No. 20, pp. 9677-9686, 1988.
Huang et al., "Multiplex Fluorescence Melting Curve Analysis for Mutation Detection with Dual-Labeled, Self-Quenched Probes", PLoS One, vol. 6, Issue 4, e19206, 2011.
Greene et al., "A Novel Method for SNP Analysis Using Fluorescence Polarization", PerkinElmer Life Sciences Publication P10131 rev. 07/01, pp. 1-8, 2002.
Rudi et al., "Multiplex real-time single nucleotide polymorphism detection and quantification by quencher extension", BioTechniques, vol. 40, No. 3, pp. 323-329, 2006.
Office Action issued Nov. 12, 2019 in Japanese Patent Application No. 2017-558783 with English-language translation.

* cited by examiner

FIG. 1

Overview of Liquid Array Diagnostics SNP Typing

A Main Steps of LAD

1. PCR amplification of genomic DNA with Forward & Reverse PCR primers (polymerase + dNTPs) to generate the amplified template for subsequent labeling of labeling probe.
2. Treatment of PCR reaction with Exonuclease I (degrades PCR primers) and phosphatase (degrades dNTPs)
3. Incubation at 85 deg C to inactivate the Exonuclease and phosphatase enzymes.
4. Addition of labeling probe, ddNTPs + polymerase; labeling for 5-20 cycles.
5. Addition of reporter probe (and proteinase K and/or phosphatase to alleviate the false positive effect); melting curve analysis and fluorescence detection.

B

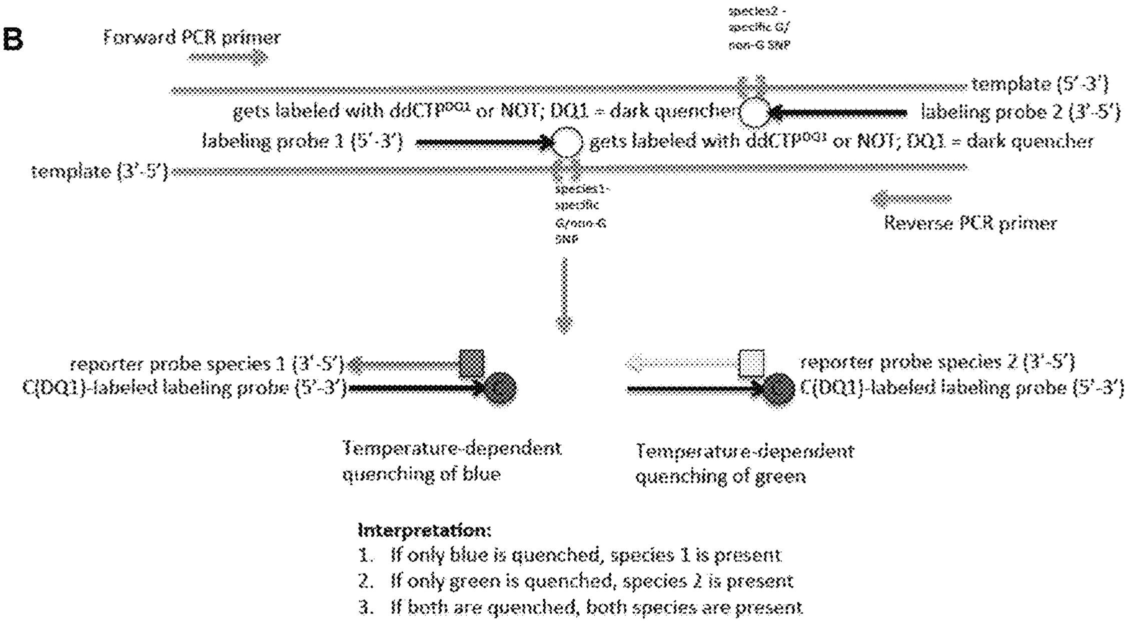

C

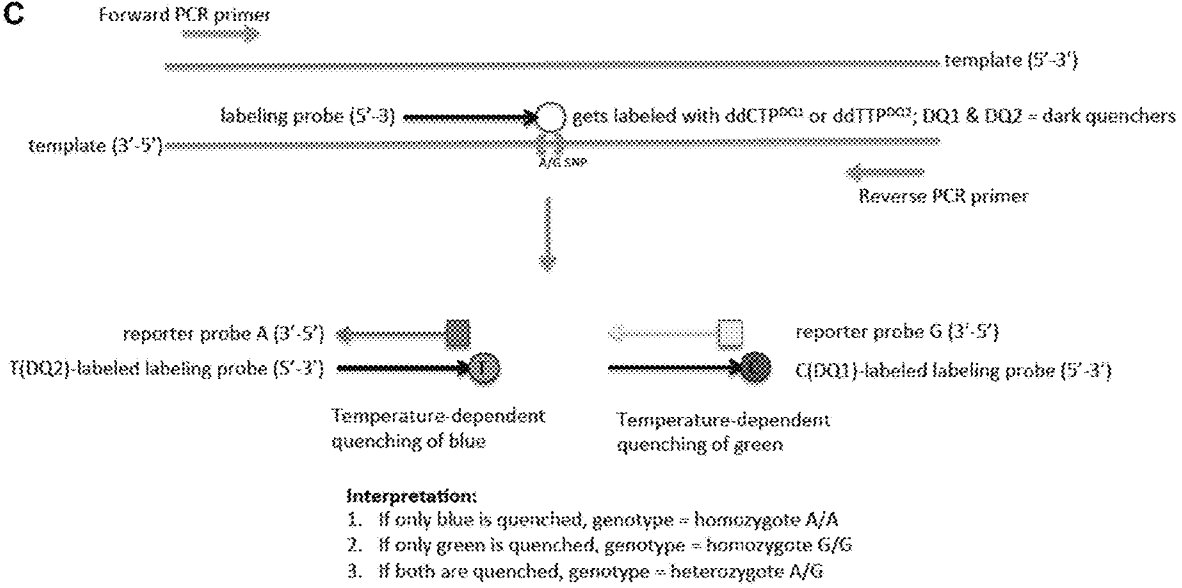

FIG. 8
A
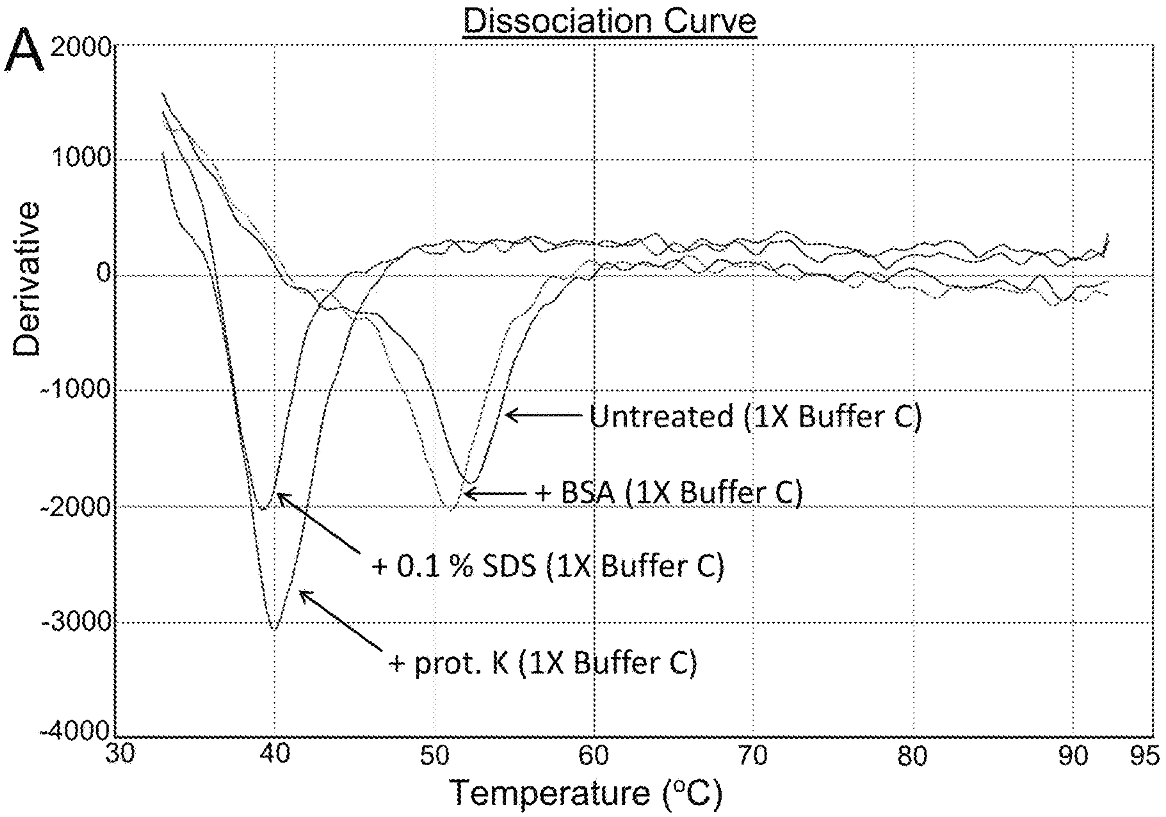
B
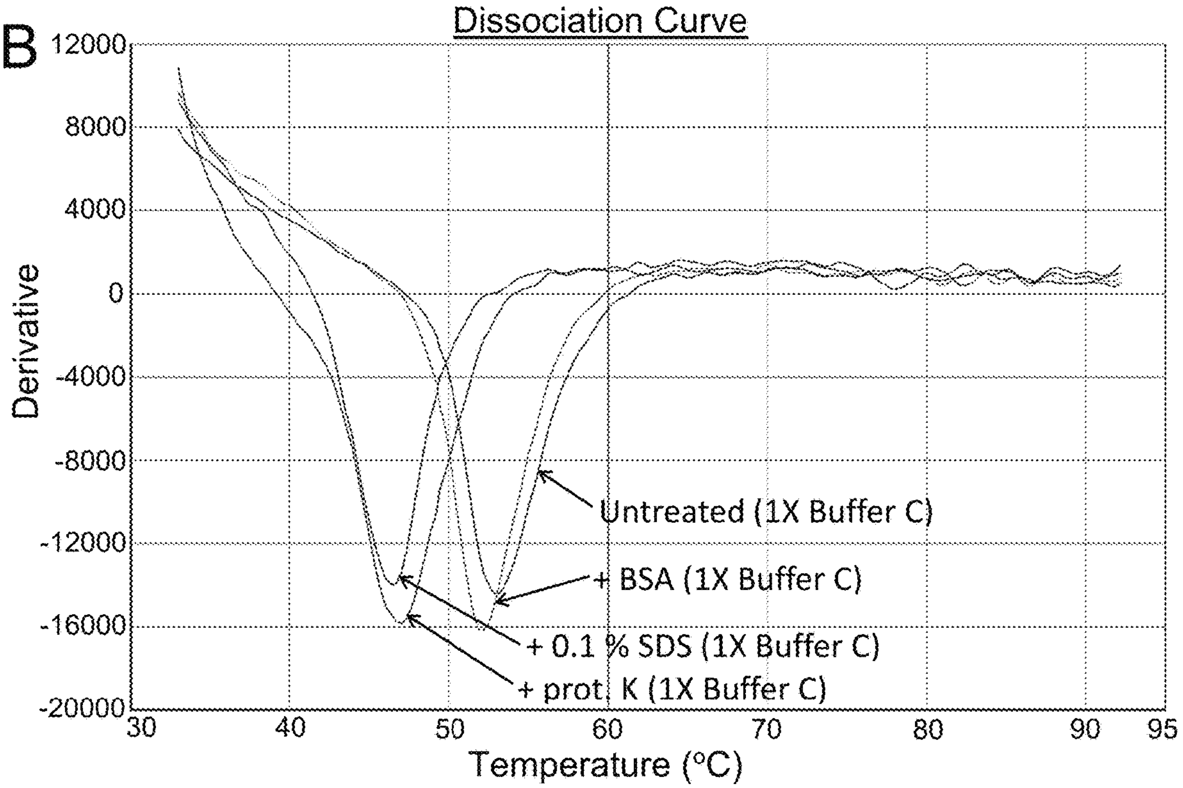

FIG. 9
A
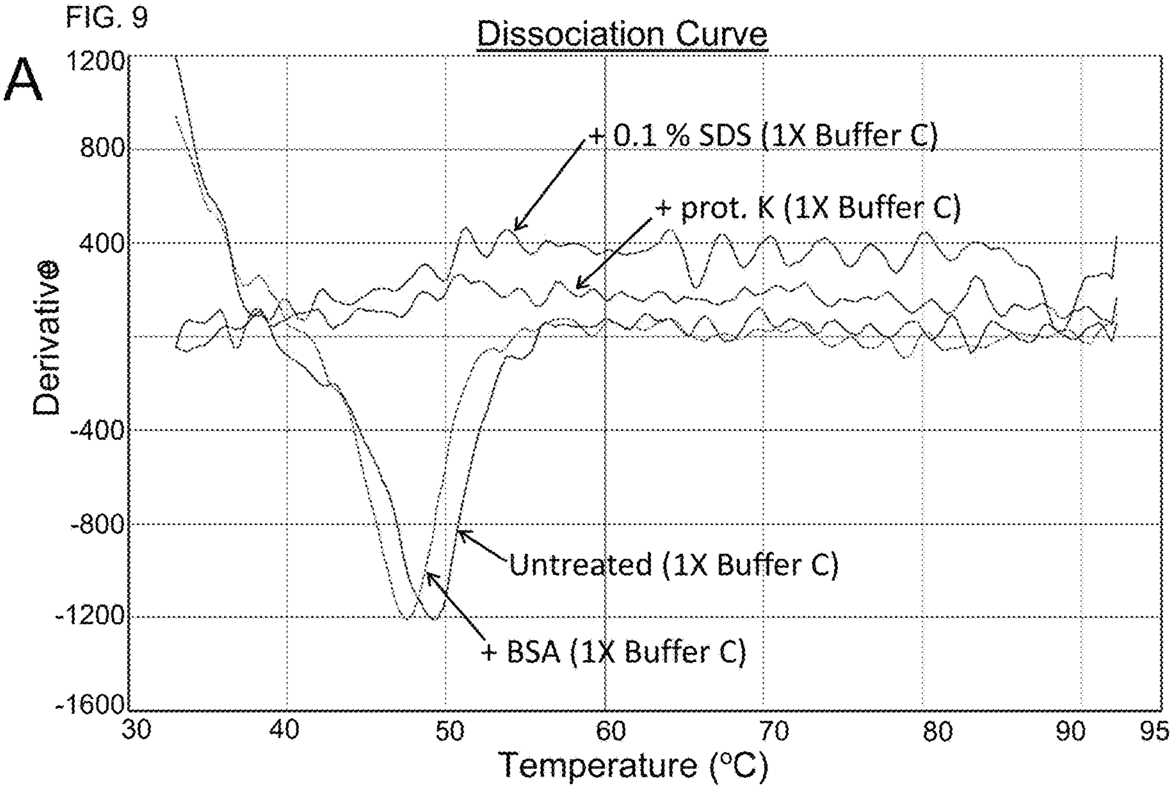
B
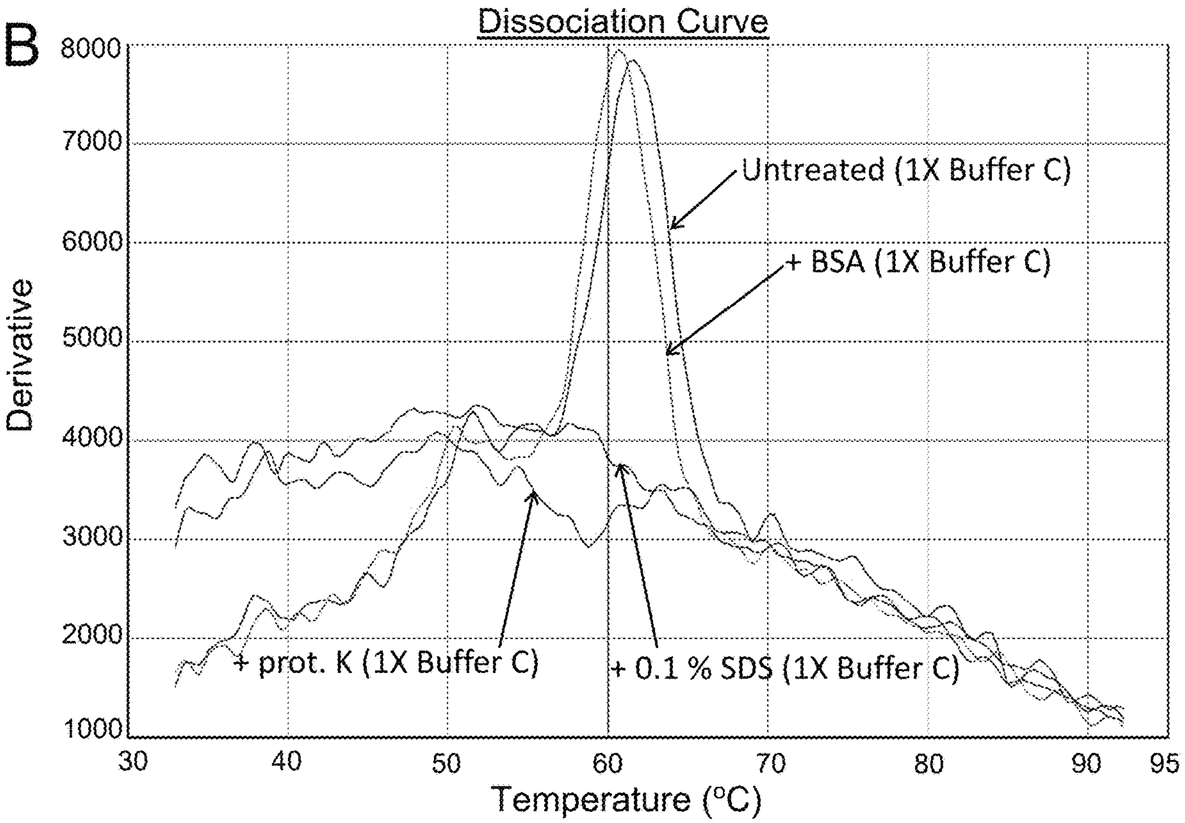

FIG. 10
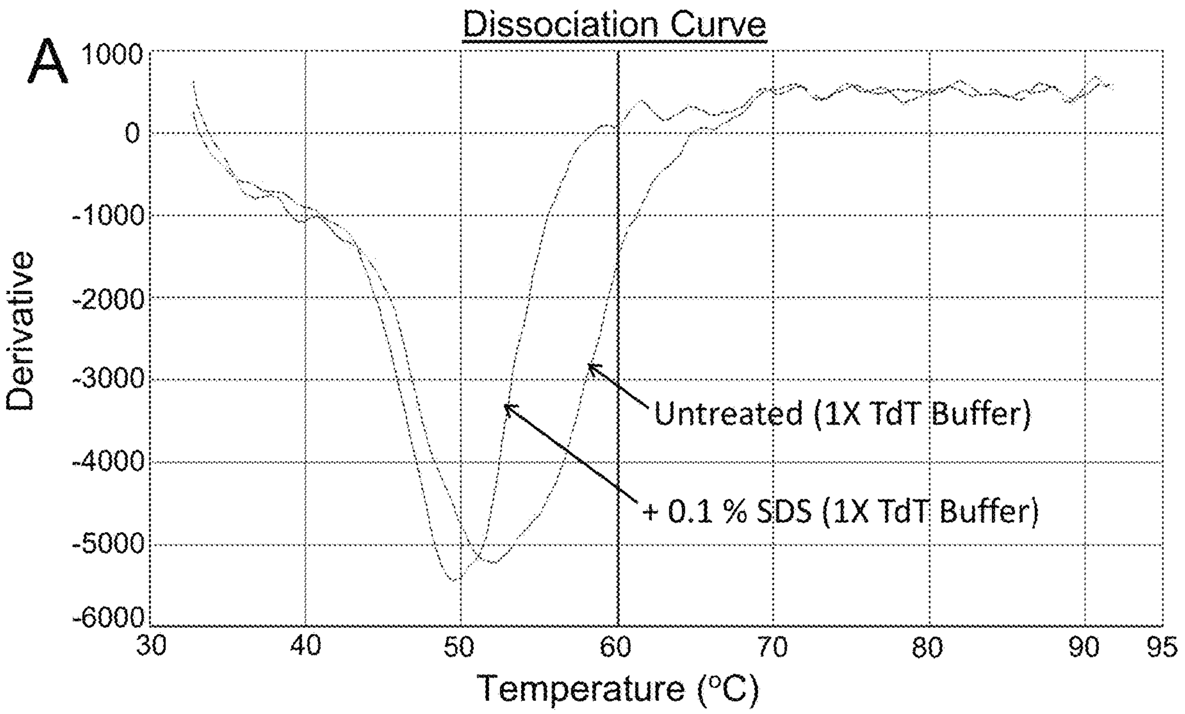
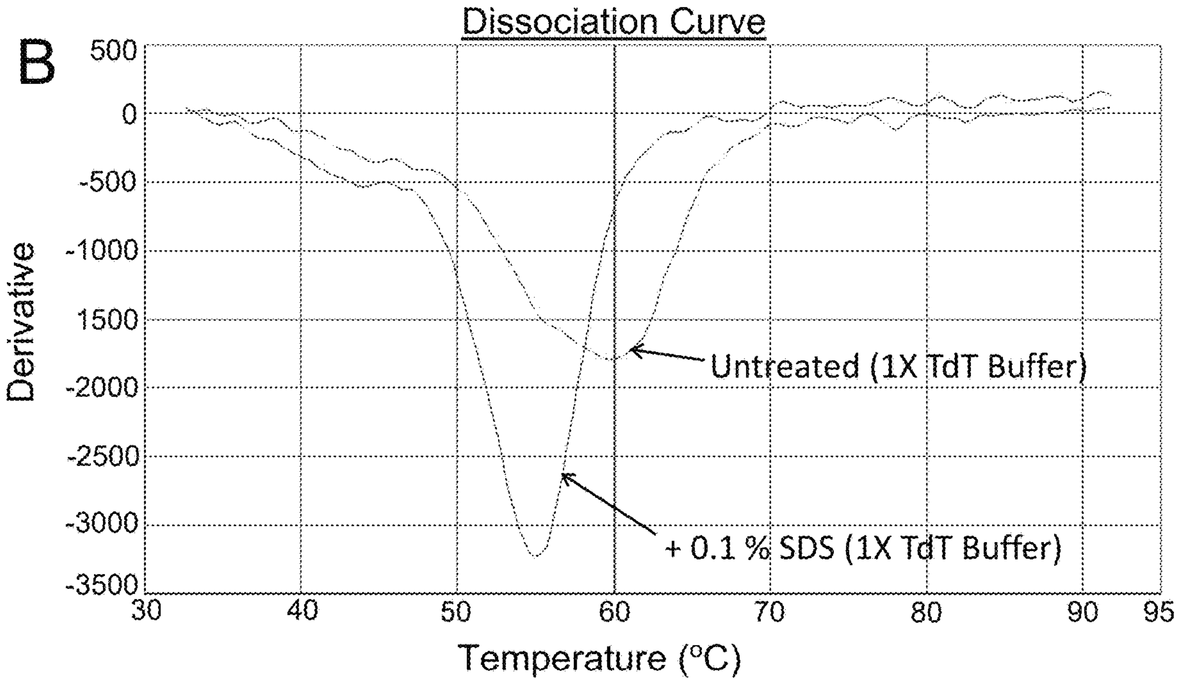

FIG. 10 (Cont.)
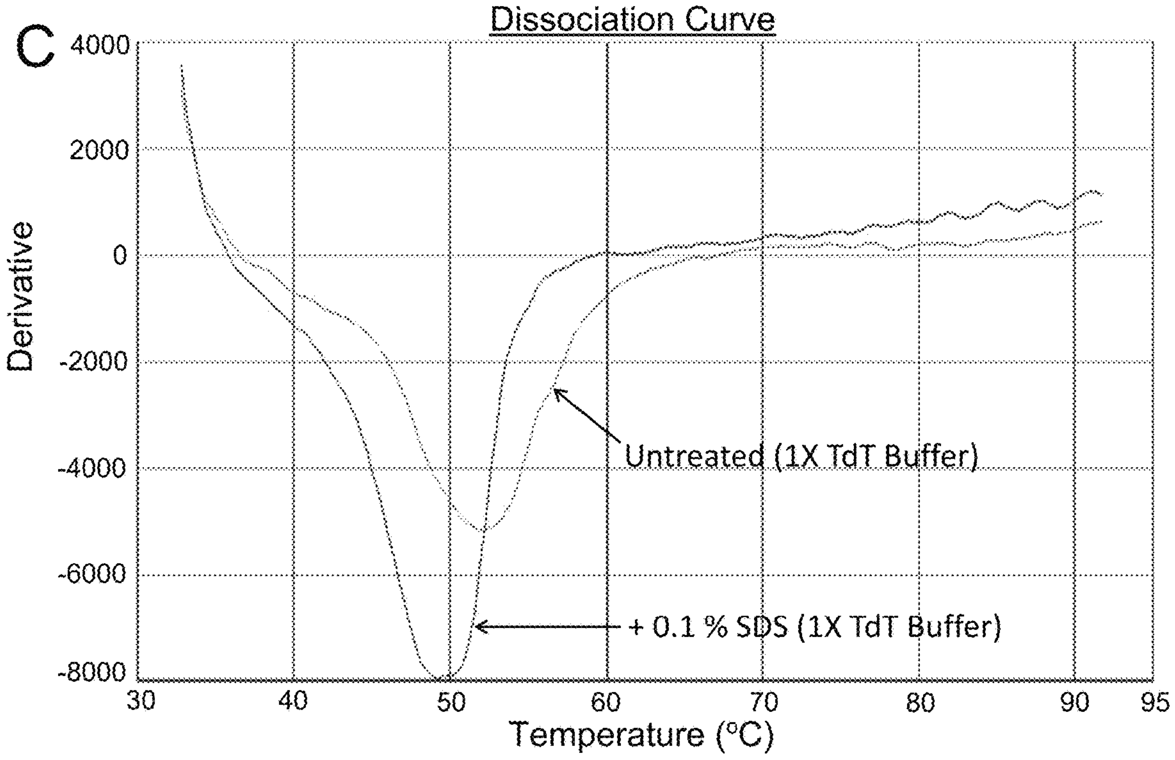
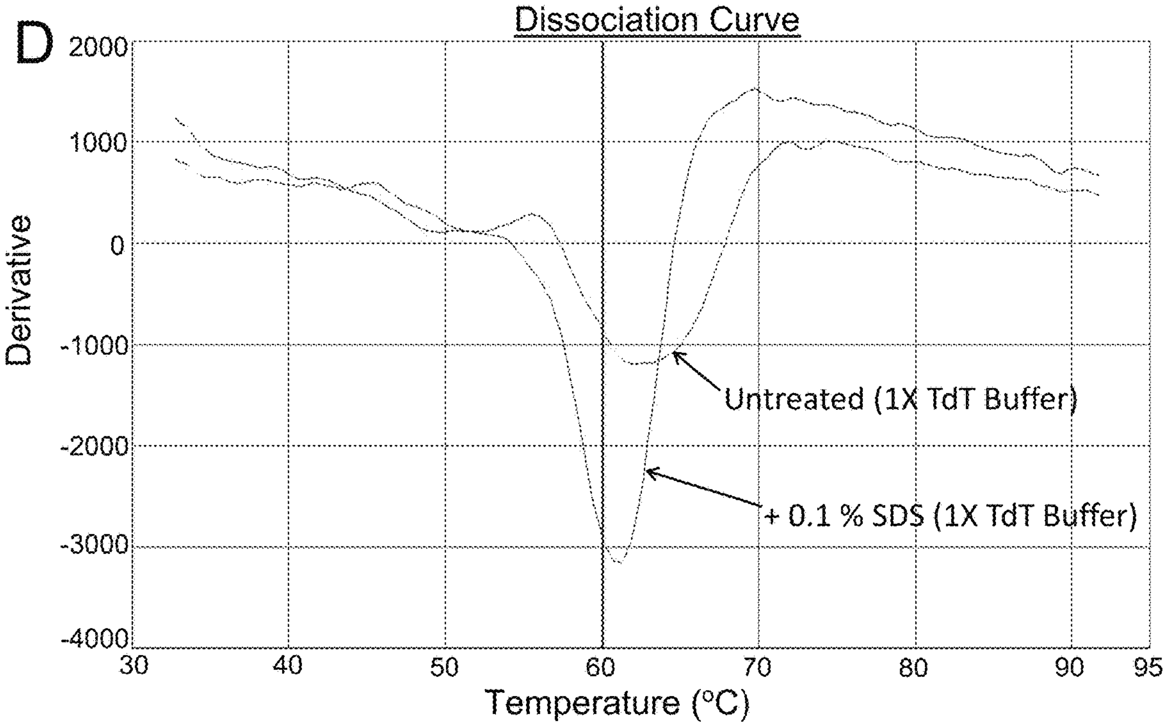

FIG. 11 (Cont.)
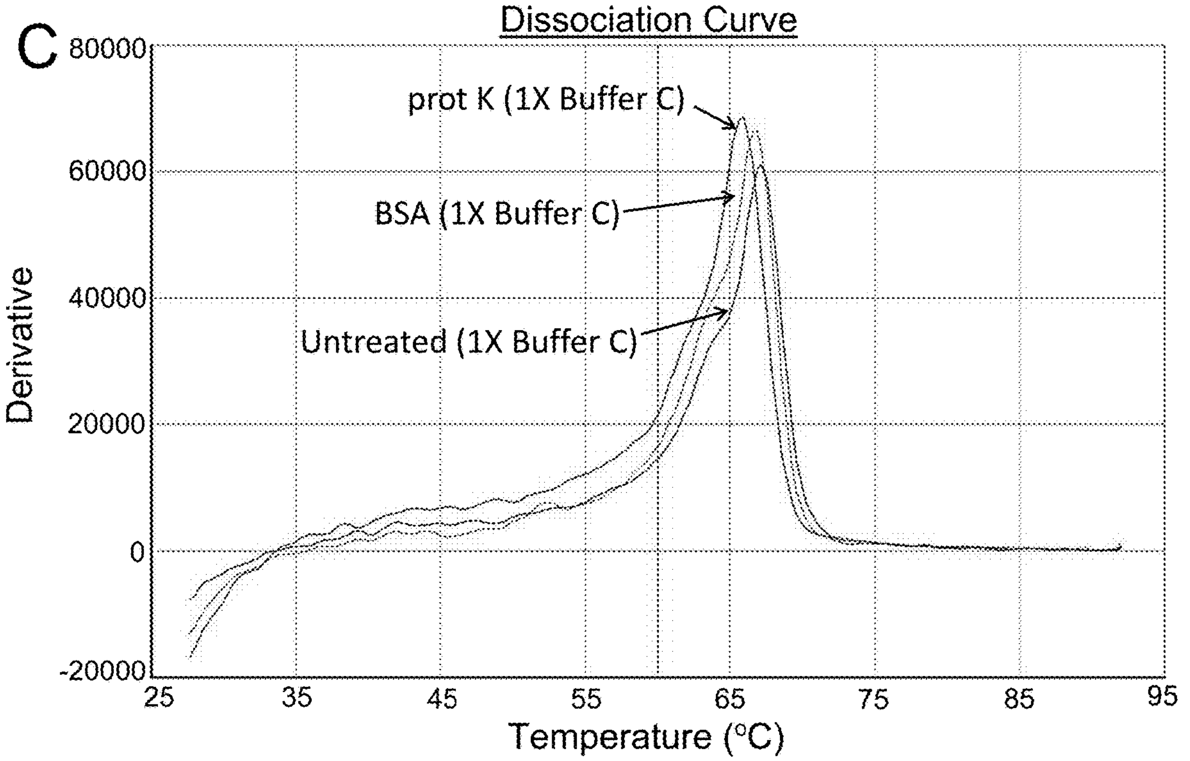
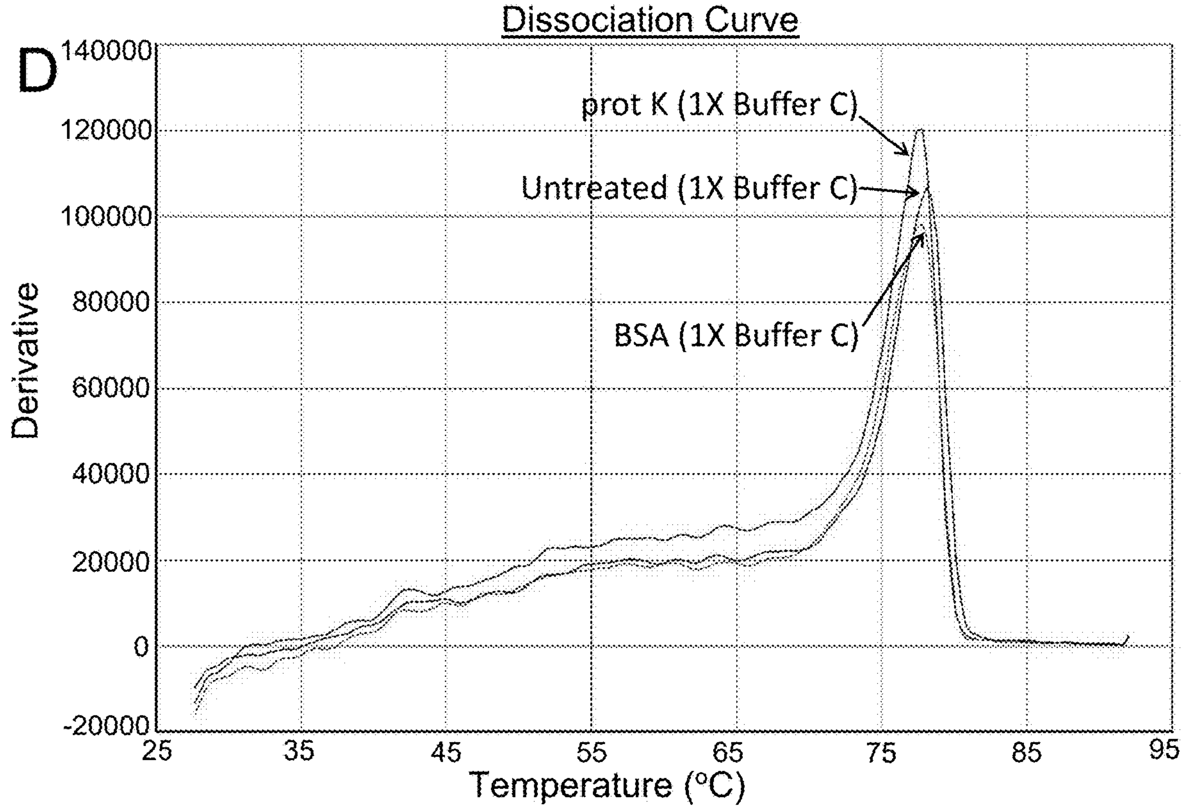

FIG. 12
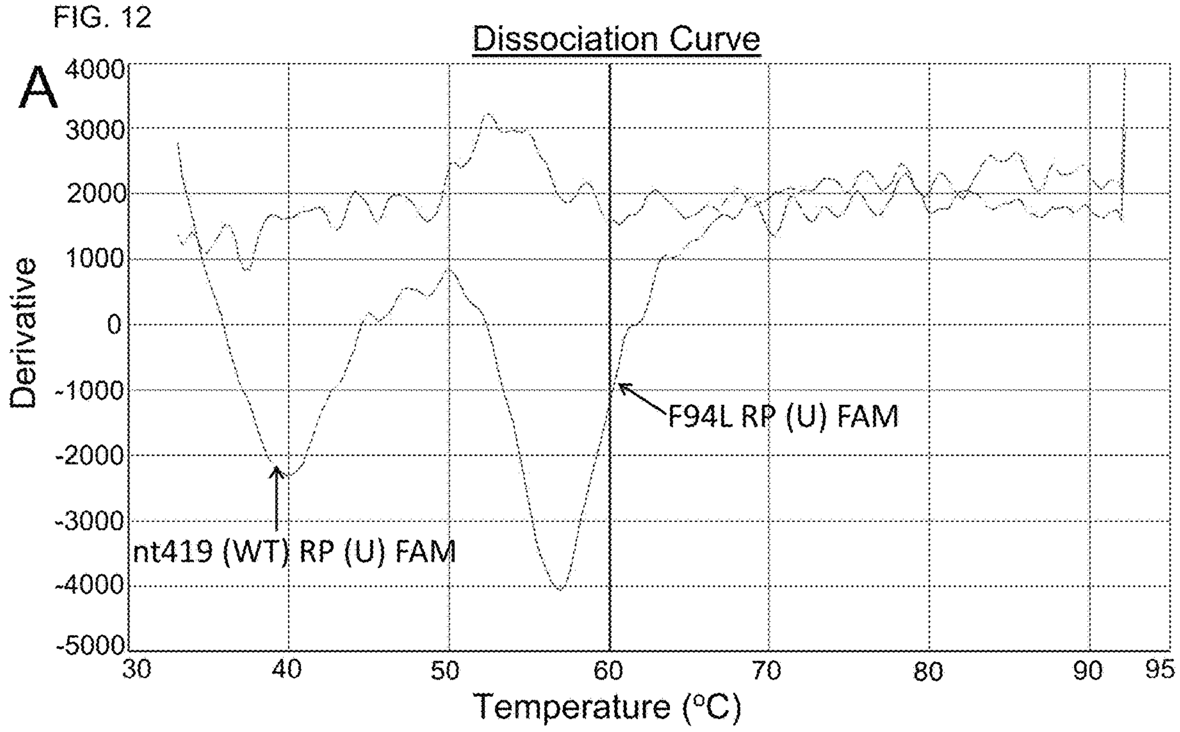
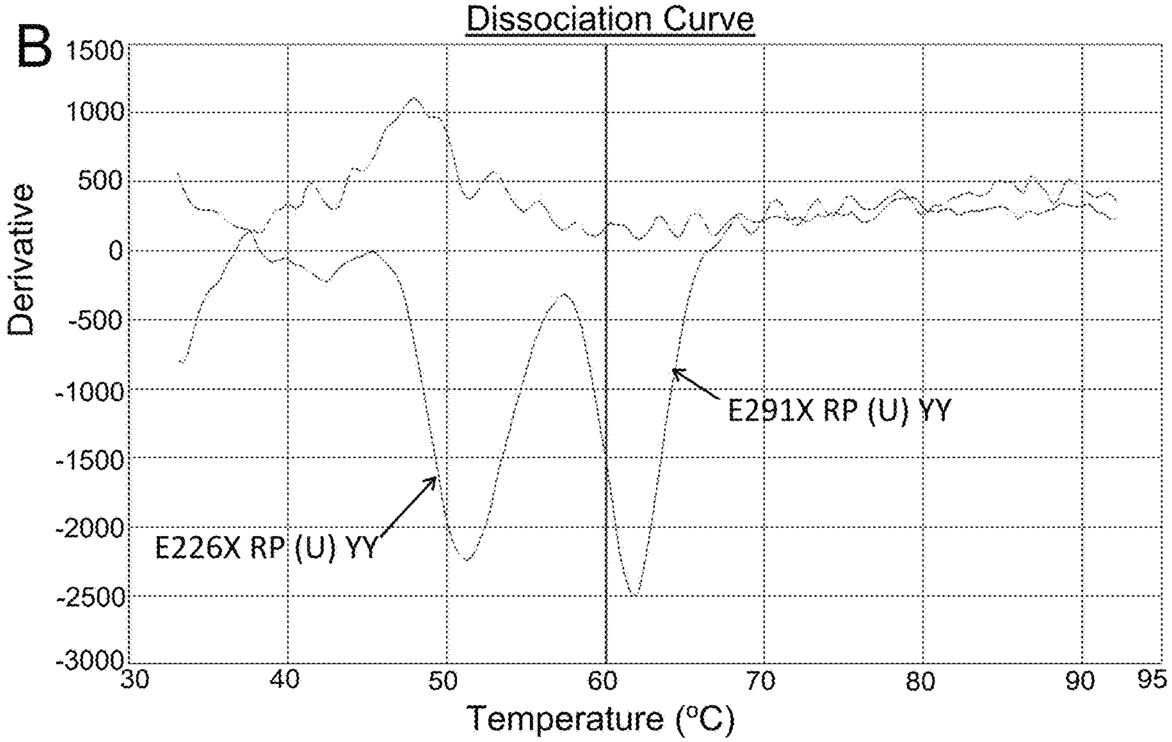

SEQUENCE LISTING

```
<160> NUMBER OF SEQ ID NOS: 49

<210> SEQ ID NO 1
<211> LENGTH: 28
<212> TYPE: DNA
<213> ORGANISM: Artificial Sequence
<220> FEATURE:
<223> OTHER INFORMATION: Primer 2_1 LP

<400> SEQUENCE: 1

caggtgtagc ggtgaaatgc gtagagat                                          28


<210> SEQ ID NO 2
<211> LENGTH: 28
<212> TYPE: DNA
<213> ORGANISM: Artificial Sequence
<220> FEATURE:
<223> OTHER INFORMATION: Primer 2_1_in1bFAMRevComp

<400> SEQUENCE: 2

atctctacgc atttcaccgc tacacctg                                          28


<210> SEQ ID NO 3
<211> LENGTH: 19
<212> TYPE: DNA
<213> ORGANISM: Artificial Sequence
<220> FEATURE:
<223> OTHER INFORMATION: Primer Faecali LP

<400> SEQUENCE: 3

cgtagttagc cgtcacttc                                                    19
```

-continued

<210> SEQ ID NO 4
<211> LENGTH: 20
<212> TYPE: DNA
<213> ORGANISM: Artificial Sequence
<220> FEATURE:
<223> OTHER INFORMATION: Primer Faecali RevComp +1 FAM

<400> SEQUENCE: 4
ggaagtgacg gctaactacg 20

<210> SEQ ID NO 5
<211> LENGTH: 19
<212> TYPE: DNA
<213> ORGANISM: Artificial Sequence
<220> FEATURE:
<223> OTHER INFORMATION: Primer Faecali RevComp FAM

<400> SEQUENCE: 5
gaagtgacgg ctaactacg 19

<210> SEQ ID NO 6
<211> LENGTH: 16
<212> TYPE: DNA
<213> ORGANISM: Artificial Sequence
<220> FEATURE:
<223> OTHER INFORMATION: Primer LAD LP GP2

<400> SEQUENCE: 6
gagctggggt agcagg 16

<210> SEQ ID NO 7
<211> LENGTH: 15
<212> TYPE: DNA
<213> ORGANISM: Artificial Sequence
<220> FEATURE:
<223> OTHER INFORMATION: Primer LAD LP GP2 -1(5')

<400> SEQUENCE: 7
agctggggta gcagg 15

<210> SEQ ID NO 8
<211> LENGTH: 17
<212> TYPE: DNA
<213> ORGANISM: Artificial Sequence
<220> FEATURE:
<223> OTHER INFORMATION: Primer LAD LP GP2 5'T

<400> SEQUENCE: 8
tgagctgggg tagcagg 17

<210> SEQ ID NO 9
<211> LENGTH: 15
<212> TYPE: DNA
<213> ORGANISM: Artificial Sequence
<220> FEATURE:
<223> OTHER INFORMATION: Primer LAD RP1 GP2atda -1 (FAM)

<400> SEQUENCE: 9
ctgctacccc agctc 15

<210> SEQ ID NO 10
<211> LENGTH: 17
<212> TYPE: DNA
<213> ORGANISM: Artificial Sequence
<220> FEATURE:

-continued

<223> OTHER INFORMATION: Primer LAD RP1 GP2atda +1T (FAM)

<400> SEQUENCE: 10
tcctgctacc ccagctc 17

<210> SEQ ID NO 11
<211> LENGTH: 18
<212> TYPE: DNA
<213> ORGANISM: Artificial Sequence
<220> FEATURE:
<223> OTHER INFORMATION: Primer LAD RP1 GP2atda +2T FAM

<400> SEQUENCE: 11
ttcctgctac cccagctc 18

<210> SEQ ID NO 12
<211> LENGTH: 16
<212> TYPE: DNA
<213> ORGANISM: Artificial Sequence
<220> FEATURE:
<223> OTHER INFORMATION: Primer LAD RP1 GP2atda 0 FAM

<400> SEQUENCE: 12
cctgctaccc cagctc 16

<210> SEQ ID NO 13
<211> LENGTH: 24
<212> TYPE: DNA
<213> ORGANISM: Artificial Sequence
<220> FEATURE:
<223> OTHER INFORMATION: Primer HR

<400> SEQUENCE: 13
gcttccggct cgtatgttgt gtgg 24

<210> SEQ ID NO 14
<211> LENGTH: 25
<212> TYPE: DNA
<213> ORGANISM: Artificial Sequence
<220> FEATURE:
<223> OTHER INFORMATION: Primer HU

<400> SEQUENCE: 14
cgccagggtt ttcccagtca cgacg 25

<210> SEQ ID NO 15
<211> LENGTH: 20
<212> TYPE: DNA
<213> ORGANISM: Artificial Sequence
<220> FEATURE:
<223> OTHER INFORMATION: Primer SP_MSTN gene_371-480

<400> SEQUENCE: 15
ctcctccact cctggaactg 20

<210> SEQ ID NO 16
<211> LENGTH: 18
<212> TYPE: DNA
<213> ORGANISM: Artificial Sequence
<220> FEATURE:
<223> OTHER INFORMATION: Primer ASP_MSTN gene_371-480

<400> SEQUENCE: 16
cgtcctggcg tggtagtc 18

-continued

<210> SEQ ID NO 17
<211> LENGTH: 26
<212> TYPE: DNA
<213> ORGANISM: Artificial Sequence
<220> FEATURE:
<223> OTHER INFORMATION: Primer SP_MSTN gene_2329-2688

<400> SEQUENCE: 17
ttatagctga tcttctaacg caagtg 26

<210> SEQ ID NO 18
<211> LENGTH: 22
<212> TYPE: DNA
<213> ORGANISM: Artificial Sequence
<220> FEATURE:
<223> OTHER INFORMATION: Primer ASP_MSTN gene_2329-2688

<400> SEQUENCE: 18
ctgggaaggt tacagcaaga tc 22

<210> SEQ ID NO 19
<211> LENGTH: 22
<212> TYPE: DNA
<213> ORGANISM: Artificial Sequence
<220> FEATURE:
<223> OTHER INFORMATION: Primer SP_MSTN gene_4787-4976

<400> SEQUENCE: 19
ggagagattt tgggcttgat tg 22

<210> SEQ ID NO 20
<211> LENGTH: 24
<212> TYPE: DNA
<213> ORGANISM: Artificial Sequence
<220> FEATURE:
<223> OTHER INFORMATION: Primer ASP_MSTN gene_4787-4976

<400> SEQUENCE: 20
tgcacaagat gggtatgagg atac 24

<210> SEQ ID NO 21
<211> LENGTH: 60
<212> TYPE: DNA
<213> ORGANISM: Artificial Sequence
<220> FEATURE:
<223> OTHER INFORMATION: Primer ASP60

<400> SEQUENCE: 21
ttgtgatgta gatggcggtt aggacggcag ttttatggag gtggataggt ctttactcag 60

<210> SEQ ID NO 22
<211> LENGTH: 30
<212> TYPE: DNA
<213> ORGANISM: Artificial Sequence
<220> FEATURE:
<223> OTHER INFORMATION: Primer ASP30

<400> SEQUENCE: 22
agttttatgg aggtggatag gtctttactc 30

<210> SEQ ID NO 23
<211> LENGTH: 20
<212> TYPE: DNA
<213> ORGANISM: Artificial Sequence
<220> FEATURE:
<223> OTHER INFORMATION: Primer ASP20

-continued

<400> SEQUENCE: 23
agttttatgg aggtggatag 20

<210> SEQ ID NO 24
<211> LENGTH: 16
<212> TYPE: DNA
<213> ORGANISM: Artificial Sequence
<220> FEATURE:
<223> OTHER INFORMATION: Primer ASP16

<400> SEQUENCE: 24
ttatggaggt ggatag 16

<210> SEQ ID NO 25
<211> LENGTH: 60
<212> TYPE: DNA
<213> ORGANISM: Artificial Sequence
<220> FEATURE:
<223> OTHER INFORMATION: Primer SP60

<400> SEQUENCE: 25
ctgagtaaag acctatccac ctccataaaa ctgccgtcct aaccgccatc tacatcacaa 60

<210> SEQ ID NO 26
<211> LENGTH: 21
<212> TYPE: DNA
<213> ORGANISM: Artificial Sequence
<220> FEATURE:
<223> OTHER INFORMATION: Primer D182N LP (C_U)

<400> SEQUENCE: 26
ttccagtata ccttgtaccg t 21

<210> SEQ ID NO 27
<211> LENGTH: 24
<212> TYPE: DNA
<213> ORGANISM: Artificial Sequence
<220> FEATURE:
<223> OTHER INFORMATION: Primer D182N RP (C)CY5

<400> SEQUENCE: 27
tttcggtaca aggtatactg gaat 24

<210> SEQ ID NO 28
<211> LENGTH: 27
<212> TYPE: DNA
<213> ORGANISM: Artificial Sequence
<220> FEATURE:
<223> OTHER INFORMATION: Primer C313Y LP (C_U)

<400> SEQUENCE: 28
ggatactttt gcaaaaatac aaattca 27

<210> SEQ ID NO 29
<211> LENGTH: 26
<212> TYPE: DNA
<213> ORGANISM: Artificial Sequence
<220> FEATURE:
<223> OTHER INFORMATION: Primer C313Y RP (U)FAM
<220> FEATURE:
<221> NAME/KEY: modified_base
<222> LOCATION: (3)..(11)
<223> OTHER INFORMATION: n is C-5 Propynyl-deoxyuridine
<220> FEATURE:
<221> NAME/KEY: modified_base
<222> LOCATION: (24)..(25)
<223> OTHER INFORMATION: n is C-5 Propynyl-deoxycytidine

<400> SEQUENCE: 29
aanttgtatt nttgcaaaag tatnnt 26

<210> SEQ ID NO 30
<211> LENGTH: 21
<212> TYPE: DNA
<213> ORGANISM: Artificial Sequence
<220> FEATURE:
<223> OTHER INFORMATION: Primer nt821 (del11) LP (U)

<400> SEQUENCE: 30
gggcttgatt gtgatgaaca c 21

<210> SEQ ID NO 31
<211> LENGTH: 18
<212> TYPE: DNA
<213> ORGANISM: Artificial Sequence
<220> FEATURE:
<223> OTHER INFORMATION: Primer nt821 RP (U) HEX

<400> SEQUENCE: 31
tttgttcatc actatcaa 18

<210> SEQ ID NO 32
<211> LENGTH: 18
<212> TYPE: DNA
<213> ORGANISM: Artificial Sequence
<220> FEATURE:
<223> OTHER INFORMATION: Primer Q204X LP (C_U)

<400> SEQUENCE: 32
ccaggcactg gtatttgg 18

<210> SEQ ID NO 33
<211> LENGTH: 23
<212> TYPE: DNA
<213> ORGANISM: Artificial Sequence
<220> FEATURE:
<223> OTHER INFORMATION: Primer Q204X RP2 (C) ROX

<400> SEQUENCE: 33
tttttcaaat actagtgcct ggg 23

<210> SEQ ID NO 34
<211> LENGTH: 20
<212> TYPE: DNA
<213> ORGANISM: Artificial Sequence
<220> FEATURE:
<223> OTHER INFORMATION: Primer E291X LP (C)

<400> SEQUENCE: 34
ccaatcccat ccaaaagctt 20

<210> SEQ ID NO 35
<211> LENGTH: 23
<212> TYPE: DNA
<213> ORGANISM: Artificial Sequence
<220> FEATURE:
<223> OTHER INFORMATION: Primer E291X RP (C) CY5
<220> FEATURE:
<221> NAME/KEY: modified_base
<222> LOCATION: (6)..(6)
<223> OTHER INFORMATION: n is C-5 propynyl deoxycytidine
<220> FEATURE:
<221> NAME/KEY: modified_base
<222> LOCATION: (8)..(8)

<223> OTHER INFORMATION: n is C-5 propynyl deoxyuridine

<400> SEQUENCE: 35
tttagntntt ggatgggatt gga 23

<210> SEQ ID NO 36
<211> LENGTH: 20
<212> TYPE: DNA
<213> ORGANISM: Artificial Sequence
<220> FEATURE:
<223> OTHER INFORMATION: Primer F94L LP (C)

<400> SEQUENCE: 36
ctggaactga ttgatcagtt 20

<210> SEQ ID NO 37
<211> LENGTH: 23
<212> TYPE: DNA
<213> ORGANISM: Artificial Sequence
<220> FEATURE:
<223> OTHER INFORMATION: Primer F94L RP3 (C) ROX

<400> SEQUENCE: 37
tttactgatc aatcagttcc agg 23

<210> SEQ ID NO 38
<211> LENGTH: 25
<212> TYPE: DNA
<213> ORGANISM: Artificial Sequence
<220> FEATURE:
<223> OTHER INFORMATION: Primer E226X LP (C)

<400> SEQUENCE: 38
ccattctcat ctaaagcttt gattt 25

<210> SEQ ID NO 39
<211> LENGTH: 25
<212> TYPE: DNA
<213> ORGANISM: Artificial Sequence
<220> FEATURE:
<223> OTHER INFORMATION: Primer E226X RP (C) CY5

<400> SEQUENCE: 39
aatcaaaact ttagatgaga atggc 25

<210> SEQ ID NO 40
<211> LENGTH: 20
<212> TYPE: DNA
<213> ORGANISM: Artificial Sequence
<220> FEATURE:
<223> OTHER INFORMATION: Primer E226X LP (U)

<400> SEQUENCE: 40
ctgaatccaa cttaggcatt 20

<210> SEQ ID NO 41
<211> LENGTH: 20
<212> TYPE: DNA
<213> ORGANISM: Artificial Sequence
<220> FEATURE:
<223> OTHER INFORMATION: Primer E226X RP (U)YY

<400> SEQUENCE: 41
atgcctaagc tggattcagg 20

<210> SEQ ID NO 42
<211> LENGTH: 23
<212> TYPE: DNA
<213> ORGANISM: Artificial Sequence
<220> FEATURE:
<223> OTHER INFORMATION: Primer E291X LP (U)

<400> SEQUENCE: 42
gttaccctct aactgtggat ttt 23

<210> SEQ ID NO 43
<211> LENGTH: 23
<212> TYPE: DNA
<213> ORGANISM: Artificial Sequence
<220> FEATURE:
<223> OTHER INFORMATION: Primer E291X RP (U)YY
<220> FEATURE:
<221> NAME/KEY: modified_base
<222> LOCATION: (5)..(22)
<223> OTHER INFORMATION: n is m5c

<400> SEQUENCE: 43
aaatncanag ttagagggta ang 23

<210> SEQ ID NO 44
<211> LENGTH: 18
<212> TYPE: DNA
<213> ORGANISM: Artificial Sequence
<220> FEATURE:
<223> OTHER INFORMATION: Primer F94L LP (U)

<400> SEQUENCE: 44
ggcatctctc tggacatc 18

<210> SEQ ID NO 45
<211> LENGTH: 18
<212> TYPE: DNA
<213> ORGANISM: Artificial Sequence
<220> FEATURE:
<223> OTHER INFORMATION: Primer F94L RP (U)FAM

<400> SEQUENCE: 45
atgtccagag agatgcca 18

<210> SEQ ID NO 46
<211> LENGTH: 29
<212> TYPE: DNA
<213> ORGANISM: Artificial Sequence
<220> FEATURE:
<223> OTHER INFORMATION: Primer nt419 Wt LP (U)

<400> SEQUENCE: 46
agtttattgt attgtatctt agagctaaa 29

<210> SEQ ID NO 47
<211> LENGTH: 16
<212> TYPE: DNA
<213> ORGANISM: Artificial Sequence
<220> FEATURE:
<223> OTHER INFORMATION: Primer nt419 RP (U) FAM

<400> SEQUENCE: 47
tttagctcta agatag 16

<210> SEQ ID NO 48
<211> LENGTH: 24
<212> TYPE: DNA

-continued

```
<213> ORGANISM: Artificial Sequence
<220> FEATURE:
<223> OTHER INFORMATION: Primer nt419 (d7i10) LP (C)

<400> SEQUENCE: 48

gaaaacccaa atgttgtttc taag                                  24


<210> SEQ ID NO 49
<211> LENGTH: 20
<212> TYPE: DNA
<213> ORGANISM: Artificial Sequence
<220> FEATURE:
<223> OTHER INFORMATION: Primer nt419 (d7i10) RP (C) ROX

<400> SEQUENCE: 49

ttttcttaga aacaacatta                                       20
```

METHOD FOR PREVENTING FALSE POSITIVES IN METHODS EMPLOYING DDNTP'S

The present invention relates to a method which prevents undesirable binding of ddNTPs to double stranded polynucleotides when in the presence of a polymerase. Such methods may be used to prevent the appearance of false positives in methods employing ddNTPs, e.g. in sequence detection methods. The present invention also provides a method of avoiding a false Tm reading or false FRET effects (such as false positive quenching), for example in a melting curve analysis method. In particular a method is provided in which a target nucleotide sequence in a test polynucleotide is detected using a method in which a double stranded molecule is generated which may or may not comprise two labels depending on whether the target sequence is present in which the presence of the two labels is determined, preferably by performing a melting curve analysis.

Polynucleotide sequencing and the identification of specific polynucleotide sequences within a target sample has been carried out by various methods for many years and allows information on that sample to be gathered, which may be used in a variety of ways, e.g. for diagnostic purposes (e.g. for the presence of a contaminant and/or sample type, incidence or propensity for a disease, etc).

In many cases relevant information may be obtained by detection of variation within a sequence, e.g. in a single base. Such variation may arise from allelic variation or polymorphism, a point mutation, or any deletion or insertion of genetic material. The detection of single nucleotide polymorphisms (SNPs) are of particular interest. These SNPs reflect natural variation within a population. SNPs provide markers that can be used to study population dynamics and evolution, to investigate the genetic basis of complex phenotypes and in forensic or diagnostic assays. In particular SNPs have been found to be associated with specific diseases and hence can be used to identify individuals with propensity for that disease and/or to tailor treatments for that individual based on their genotype.

A number of methods of sequencing, including SNP detection involve the use of dideoxy NTPs. DNA sequencing has been traditionally carried out by the Sanger dideoxy method (Sanger, Nicklen and Coulson, Proc. Natl. Acad. Sci. USA, 1977, 74, 5463-7) which has been used since the 1980s. It is a multimolecular method based on electrophoretic filtering of DNA, which may be cloned, that is firstly treated enzymatically. The enzymatic process produces single stranded DNA by interrupted polymerisation using a mixture of fluorophore labelled dideoxy NTPs which terminate chain extension and dNTPs which do not. Hence, a mixture of chain lengths is obtained using this process where the length of each DNA strand represents the base position and the colour of the connected fluorophore represents the identity of the base at the 3' end. These identities are read as aligned coloured dots, with one line of dots representing one DNA sequence.

Other sequencing methods which may include the use of ddNTP include sequencing by stepwise ligation and cleavage when ddNTP may be used together with probes which ligate to the target sequence.

There are various commonly used methods of detecting SNPs. Hybridization of an oligonucleotide specific for a particular SNP may be used and binding may be detected, e.g. by use of the oligonucleotide as a primer (i.e. amplification in PCR is evidence of the existence of the SNP sequence). The oligonucleotide may bind to the SNP (such that different oligonucleotides need to be used to accommodate different sequences) or may bind upstream of the SNP (where only relevant sequences are extended by the oligonucleotide acting as the primer). Methods involving allele-specific ligation (when two bound probes are able to ligate only when bound to a relevant sequence) or allele-specific enzymatic cleavage may be used.

Of most interest in the present case is the detection of SNPs using allele-specific single-base primer extension in which discrimination occurs at the level of nucleotide incorporation (during extension) rather than at the level of the oligonucleotide (primer) binding. In this case the primers anneal one nucleotide upstream of the polymorphic site such that the first nucleotide to be incorporated on the nascent strand is opposite the polymorphic site. Various different labels and platforms for detection may be used. In one option, a detection method may be used in which primer extension with a ddNTP specific for the SNP of interest may be used to generate a labelled probe (when the SNP is present) and this labelled probe is then captured by binding to a complementary sequence and the amount of label which is attached to the complementary sequence is indicative of the presence (and amount) of the SNP of interest (WO99/50448).

Single nucleotide primer extension using ddNTP has also been used in US2002187477 in which the extension reaction is detected based on the labelled ddNTP which is incorporated or the length of the extended molecule (dNTPs may also be used in the method). US2009305249 also uses single nucleotide primer extension and detects labelled molecules based on the label and size of the product. WO2012/049279 also discusses the use of single nucleotide primer extension to generate products which may be distinguished on the basis of their size and base composition in IP/RP HPLC.

In the above methods, when ddNTP is employed, it is used to bind to a complementary base and terminate any extension reaction. The presence of this molecule may be used to identify the presence or amount of the complementary base (in the relevant sequence context) in the sample, test polynucleotide.

However, it has now been found that under certain conditions, as described hereinafter, and not just during normal primer extension reactions, ddNTP may associate with, or bind to, a double stranded polynucleotide. This may lead to false positives in sequencing/SNP detection methods. However, it has now been found that this binding may be avoided in a number of ways, as described hereinafter. The method of the invention thus serves to prevent erroneous binding of a ddNTP to (or association with) a double stranded polynucleotide which allows false positives in sequence detection methods to be avoided. It has furthermore been found that polymerase also stabilizes polynucleotide duplexes which affects their melting temperature and can cause false FRET effects such as false positive quenching of fluorescent labels. Methods of the invention allow these effects to be avoided, particularly in melting curve analysis methods.

In particular the advantages of methods of the invention may be used in a method of identifying a target nucleotide sequence in a test polynucleotide in which specific single-base primer extension is conducted with a labelling probe and a relevant ddNTP labelled with a first label and the resultant labelling probe (which may be labelled or not depending on the presence of the corresponding complementary base in the sequence of the test polynucleotide) is bound to a reporter probe carrying a second label that affects the signal generated by the first label (or vice versa). The complexes thus generated are subject to melting curve analysis. During the process of denaturation (or dissociation) and/or hybridization of the complexes the two labels are separated from one another such that the effect of one label on the signal of the other is altered. This allows identification of the existence of a label on the labelling probe (and hence the presence of the target SNP) by monitoring the change in signal during the denaturation/hybridization process. This process may be readily subjected to multiplexing by the use of different labels and probes which generate complexes with different melting temperatures, as described in more detail hereinafter.

Whilst not wishing to be bound by theory, it is believed that binding of ddNTP to a double stranded polynucleotide occurs by various mechanisms, depending on the nature of the double stranded polynucleotide. The various mechanisms may be summarized as follows:

a) non-covalent binding of the ddNTP to the double stranded polynucleotide with the polymerase acting as a mediator or adaptor for the binding (e.g. complexing the molecules in the method);
b) covalent binding of the ddNTP to the double stranded polynucleotide by virtue of terminal transferase activity of the polymerase;
c) covalent binding of the ddNTP to the double stranded polynucleotide by virtue of promiscuous incorporation of non-complementary ddNTP by the polymerase.

Covalent binding may also occur by incorporation of the ddNTP into the double stranded polynucleotide by normal polymerase activity if the double stranded polynucleotide provides a recessed 3' end and an adjacent complementary base to the ddNTP. This can generally be avoided by appropriate selection of the sequence and/or length of the component sequences of the double stranded polynucleotide. However, the method described herein also serves to avoid such binding.

It has also been found that the presence of the polymerase affects (raises) the melting temperature of the double stranded polynucleotide thus leading to a false Tm. The polymerase has also been found to generate false FRET effects, such as false positive quenching, which may affect results even when no ddNTP is present. Methods as described herein in which the polymerase is removed serve also to address this cause of inaccurate results.

Such binding has not previously been observed. Whilst not wishing to be bound by theory, whether or not this type of binding will occur is at least partially dictated by the type of double stranded molecule. The non-covalent binding of a) may occur on molecules with blunt ends and 3' or 5' protruding ends. The covalent binding of b) occurs on molecules with blunt ends, but appears sequence sensitive; it does not appear to occur on molecules with 3' or 5' protruding ends. The covalent binding of c) occurs on molecules with a 5' protruding end. It is believed that the covalent binding occurs by incorporation of the base in a chain extension reaction by virtue of the polymerase's enzymatic activity to extend the polynucleotide in the 5' to 3' direction. The polymerase-dependent effects on Tm and the generation of false FRET effects occur on all types of double stranded molecules.

The ddNTP binding can be avoided by various means. The non-covalent binding of a) may be removed by effective removal of the polymerase, dephosphorylation or removal of the ddNTP and/or outcompeting the ddNTP with other ddNTPs (e.g. unlabelled ddNTPs). Similar mechanisms may be used to avoid the covalent binding in b) and c). The undesirable non-covalent and/or covalent binding may also be reduced or eliminated by altering the length of the single stranded region of the double stranded polynucleotide to provide a molecule which is less susceptible to the above described binding (e.g. by providing a single stranded region, e.g. a 3' protruding region or lengthening the single stranded region). Longer single stranded regions are less susceptible to the undesirable binding mentioned above and/or may be used to reduce the influence of the ddNTP (e.g. if it is labelled and interacts with a label elsewhere in the double stranded molecule its influence may be reduced by increasing its distance from the other label).

Thus, in a first aspect the present invention provides a method of preventing binding of a ddNTP to a polynucleotide in the presence of a polymerase, wherein said polynucleotide is double stranded but optionally may contain a single stranded region which is up to 10 nucleotides in length, wherein when said single stranded region provides a 5' protruding sequence it does not contain a base complementary to said ddNTP immediately adjacent to the double stranded region (preferably does not contain a base complementary to said ddNTP anywhere in said single stranded region), wherein said method (i) comprises inactivating, degrading or removing said polymerase, dephosphorylating or removing said ddNTP and/or outcompeting said ddNTP with another ddNTP and/or (ii) uses a polynucleotide with a single stranded region which provides a 3' protruding sequence which is at least 1 (preferably at least 2 or 3) nucleotide in length or a 5' protruding sequence which is at least 2 (preferably at least 3 or 4) nucleotides in length and/or uses a polynucleotide with a single stranded region at one or both of the polynucleotide's ends which is at least one nucleotide in length and said single stranded region results, at least in part, from a mismatch between one or more base pairs in said polynucleotide. The single stranded region which results, at least in part, from a mismatch may provide a 3' or 5' protruding sequence or both, at one or both ends, e.g. a mismatch at one end may lead to both a 3' and 5' protruding sequence at that end.

In one aspect the ddNTP carries a label. In a particularly preferred aspect the ddNTP carries a first label and said polynucleotide carries a second label and the first or second label affects the signal generated by the other label when the labels are in proximity to one another. Preferably the first or second label is a fluorophore and the other label is a molecule which affects the fluorescence of said fluorophore when in proximity to said fluorophore.

In a further preferred aspect, the method also comprises the step of generating the double stranded polynucleotide by contacting a first and second polynucleotide (which are sufficiently complementary to allow binding) under conditions allowing their hybridization.

As used herein, references to entities in the singular includes reference to entities in the plural and vice versa. Reference to a list of alternatives which are conjugated by the term "and/or" indicates that any, all or any combination of those alternatives may be used or present.

As used herein, reference to "preventing" binding of the ddNTP to the polynucleotide in the presence of the polymerase refers to absolute or partial prevention, i.e. to preventing any or some binding of the ddNTP to the polynucleotide which is not by virtue of a normal polymerase-mediated extension reaction from a free 3' end. A normal extension reaction occurs when a polymerase synthesizes a new DNA strand complementary to the DNA template strand by adding dNTPs or ddNTPs that are complementary to the template in 5' to 3' direction by incorporation of consecutive bases which are complementary to the bases in the template sequence.

"Binding" of the ddNTP encompasses both covalent and non-covalent binding and may be direct binding between the polynucleotide and the ddNTP or through the intermediacy of an additional molecule such that the ddNTP is in association with the polynucleotide.

A "ddNTP" is a 2',3' dideoxynucleotide that is a chain-elongating inhibitor of DNA polymerase. ddNTPs lack a 3'-hydroxyl group so once added to a growing nucleotide chain by a DNA polymerase, no further nucleotides can be added as a phosphodiester bond can not be created. The ddNTP may be one of five options, namely ddGTP, ddATP, ddTTP (or ddUTP) and ddCTP, providing, respectively, chain-terminating nucleotides corresponding to the bases guanine, adenine, thymine (or uracil) and cytosine. Functionally equivalent ddNTP variants, derivatives or analogs may also be used, e.g. biologically active, non-nucleotide analogs (e.g. AcycloTerminators (acyNTPs); PERKINELMER™ Life Sciences). Functionally equivalent variants, analogs or derivatives have the same or similar functionality as ddNTPs insofar as they can be incorporated by a DNA polymerase into a growing nucleotide chain (DNA) during chain extension, but once incorporated prevent further chain extension. Preferably the functionally equivalent variant, derivative or analog has a portion(s) of its structure in common with a ddNTP, e.g. comprises a triphosphate group and/or the base of the ddNTP. The polymerase as described herein may be used with the ddNTP variant, derivative or analog, or alternatively a polymerase specific to that variant/analog/derivative, e.g. AcycloPol; PERKINELMER™ Life Sciences, may be used. Reference to "ddNTP" herein includes such ddNTP variants, analogs and derivatives. Preferably the ddNTP is labeled as discussed hereinafter. Reference to a "dNTP" as used herein, is similarly defined, but in relation to a deoxynucleotide (triphosphate) rather than a dideoxynucleotide and similarly includes variants, analogs and derivatives as described above.

The term "base" or "nucleotide" as used (interchangeably) herein includes the natural nucleotides of adenine, guanine, cytosine, thymine and uracil, particularly in the 2'-deoxy form or non-natural nucleotides which function in the same way, i.e. form a complementary base pair with a natural nucleotide.

Reference to a "complementary base" refers to a base which specifically base pairs with its partner base according to Watson-Crick pairing. Partner bases are adenine and thymine (or uracil); and cytosine and guanine. Complementary sequences are sequences which contain a series of complementary bases which allow hybridization of the sequences through base pairing between the complementary bases.

The "polynucleotide" described herein is a DNA sequence containing multiple nucleotides and encompasses oligonucleotides and polynucleotides. The sequence is double stranded comprising a first strand and a second, complementary strand which is able to bind thereto through binding between complementary bases. Preferably said double stranded polynucleotide (in its final form) is not generated by primer extension to form that molecule (i.e. is not a double stranded molecule resulting directly from a primer binding to a polynucleotide and extension of the primer to form a double stranded molecule). Thus, whilst the first and second strands may themselves be generated by primer extension reactions they are preferably not generated together to form that double stranded molecule, where part of the first or second strand has acted as a primer. In the event that primer extension does occur to form the double stranded polynucleotide, said primer extension is preferably less than 6 nucleotides in length, e.g. 1, 2, 3, 4 or 5 nucleotides in length. The double stranded polynucleotide sequence is made up of two sequences which may each be of any length, but preferably each comprise at least 5 nucleotides, and preferably are from 5 to 200 nucleotides, e.g. from 10-100 nucleotides, e.g. from 20-50 nucleotides in length. In one alternative the first and second strands which provide the two sequences may be joined together, e.g. may be provided on a single polynucleotide which exhibits self-binding. However, in a preferred aspect, the first and second strands with the two sequences are separate molecules.

To be able to form a double stranded molecule the two sequences are able to bind to one another via the complementarity of bases within their sequences. The number of bases involved in complementary binding must be sufficient to allow the production of a stable complex. When a blunt ended double stranded molecule is generated this may involve all of the bases, though as discussed further below, even in this case non-complementarity at some bases (mismatch) may be tolerated. When a double stranded molecule with a protruding end is generated, the bases involved in complementary binding (the hybridizing or double stranded region) may comprise all or a portion of the shorter sequence making up the complex and a portion of the longer sequence making up the complex. In a preferred feature, at least 5 consecutive bases, preferably from 5 to 200 consecutive bases, e.g. from 10-100 consecutive bases, e.g. from 20-50 consecutive bases of the sequences making up the double stranded oligonucleotide are complementary to one another (which may form from 50-100%, e.g. 80-100% of the total length of the sequences.) ("Consecutive" bases encompasses the possibility of the occasional, e.g. one or two interspersed, mismatched base.)

In a preferred feature, the regions of the sequences which are involved in binding the sequences together to form the double stranded polynucleotide have 100% complementarity to one another. However, this is not necessary and perfect base pairing is not necessary. Thus, mismatches within this region may be tolerated providing the two molecules are sufficiently complementary to allow the formation of a complex which is stable enough for performance of routine melting temperature analyses. Thus for example, the regions of the sequences which bind to one another may share only 80, 90 or 95% complementarity (e.g. may have one, two, three or more mismatches). As discussed herein, mismatch bases may be used to provide the single stranded region of the double stranded polynucleotide, in full or in part, e.g. may provide one or more bases to said single stranded region.

The double stranded polynucleotide may contain a "single stranded region". Such a region exists when the full lengths of the sequences making up the double stranded polynucleotide are not involved in binding to complementary bases. In particular, single stranded regions may be present at the terminal ends of the double stranded polynucleotide to produce a 3' protruding or 5' protruding single stranded region. A 5' (or 3') protruding sequence is present when the single stranded region that is present terminates at the 5' (or 3') end of one of the sequences making up the double stranded molecule. A single stranded portion may exist, or be extended, by a mismatched base pair whose bases do not bind to one another and hence contribute directly to the single stranded region or affect binding between a matching (complementary) base pair such that they no longer bind thus contributing to the single stranded region.

The single stranded region, when present and forming a 5' protruding sequence, does not contain a base complementary to the ddNTP used in the method immediately adjacent to the double stranded region. Preferably the single stranded region does not contain a base complementary to any dNTP, that might be used in the method, immediately adjacent to the double stranded region. Thus, for example, if the ddNTP that is used is ddGTP, the single stranded region which forms a 5' protruding sequence does not contain the complementary base to guanine, i.e. does not contain cytosine immediately adjacent to the double stranded region. In some methods multiple ddNTPs may be used and in which case no base complementary to any of the ddNTPs which are used (or if the ddNTPs are labelled, no base complementary to any of the labelled ddNTPs which are used) are present in the single stranded region which forms a 5' protruding sequence immediately adjacent to the double stranded region. "Immediately adjacent" to the double stranded region refers to the first base of the single stranded region which is present 5' to the double stranded region. This may be a base to which no base with which it might form a base pair is present, or, in the case of mismatched bases, to which a base is present with which it might form a base pair, but not bound. Preferably when the single stranded region provides a 5' protruding sequence it does not contain a base complementary to said ddNTP (or dNTP) anywhere in said single stranded region.

The single stranded region may be as short as 1 nucleotide in length or up to as long as 5, 10, 20 or 30 nucleotides in length. In methods of preventing binding of a ddNTP to a polynucleotide in the presence of a polymerase, said single stranded region has up to 10 nucleotides. Such methods, but in which longer singled stranded regions are used are, however, also encompassed. A longer single stranded region may be present in other methods of the invention. Preferably, when the method of the invention comprises the step of inactivating, degrading or removing the polymerase and/or desphosphorylating or removing the ddNTP and/or outcompeting the ddNTP, the single stranded region is from 1-5 nucleotides in length, preferably 1, 2 or 3 nucleotides in length.

Reference is made herein to the "presence" of a polymerase. A polymerase which is present is a functionally active polymerase which is in direct contact with both the ddNTP and the double stranded polynucleotide. Preferably the polymerase is provided under conditions and at a concentration sufficient to allow primer extension if relevant complementary dNTPs and/or ddNTPs were present.

As referred to herein the "polymerase" is a DNA polymerase which is capable of primer extension of a double stranded polynucleotide in the 5' to 3' direction. Preferably the polymerase is thermostable for use in methods of the invention, particularly those which use temperature cycling steps. Preferably the polymerase is from any of the families A, B, C, D, X or Y and preferably has the classification EC2.7.7.7 or 2.7.7.49.

Examples of polymerases in family A include T7 DNA polymerase, Pol I, and DNA Polymerase γ. Family B polymerases include Pol II, Pol B, Pol ζ, Pol α, δ, and ε, while family C polymerases include Pol III. Family D polymerase are found in Archaeal organisms. Family X polymerases include Pol β, Pol σ, Pol λ and Pol μ and finally, Family Y polymerases include Pol ι (iota), POI κ (kappa), Pol IV, and Pol V. The polymerase may be of prokaryotic, eukaryotic or Archaeal origin. Preferably the polymerase is a family A polymerase or a Pol III polymerase or pol s polymerase or an Archaeal polymerase, or mutant variants thereof which retain the same or substantially similar functional properties as their parent molecules in terms of their ability to facilitate the same enzymatic role.

In particular, family A polymerases, particularly the Pol I polymerases such as the T7 DNA polymerase and Taq polymerase (such as ThermoSequenase™ which lacks exonuclease activity) are preferred. In a particularly preferred embodiment a thermosequenase-like DNA polymerase such as TERMIPol® or HOT TERMIPol® DNA polymerase (Solis BioDyne) is used. Eubacterial polymerases are particularly preferred. Also preferred are polymerases which effectively incorporate ddNTPs.

The polymerase may be inactivated, degraded or removed in methods of the invention. The choice of method may depend on the nature of the double stranded polynucleotide to which the ddNTP binding is to be prevented. As discussed above, although not wishing to be bound by theory, non-covalent binding of the ddNTP to the double stranded polynucleotide is believed to occur with the polymerase acting as a mediator or adaptor whereas covalent binding is believed to occur via the enzymatic activity of the polymerase. Thus in order to avoid the latter covalent binding only the enzymatic activity of the polymerase needs to be reduced or removed, whereas to avoid the non-covalent binding, preferably the polymerase is degraded or removed. In methods of avoiding a false Tm reading or false FRET effects (e.g. false positive quenching) in methods, such as in a melting curve analysis method as described hereinafter, preferably the polymerase is degraded or removed. However, polymerase inactivation is also contemplated.

As referred to herein "inactivation" of the polymerase refers to removal of one or more of the polymerase's functions, e.g. enzymatic, binding or structural properties, e.g. its polymerase and/or terminal transferase activity and/or DNA binding properties. The effect of the inactivation on the enzyme's function may be tested by performing the methods described in the Examples which illustrate the covalent binding effects of the polymerase. Conveniently, inactivation may be achieved by the use of appropriate inhibitors, such as catalpol or its analogs, or destruction of the relevant tertiary structure of the enzyme, e.g. using denaturation agents. In a preferred aspect, a detergent may be used to inactivate the polymerase, e.g. an anionic detergent which solubilizes proteins. In a particularly preferred aspect sodium dodecyl sulphate (SDS) may be used. Conveniently a concentration of 0.05-1.0%, preferably from 0.1-0.25% may be used.

Alternatively the polymerase may be "degraded". This may be achieved by appropriate chemical or enzymatic means. In a preferred aspect the polymerase is degraded by use of a proteinase. In a particularly preferred aspect, the proteinase is proteinase K (EC 3.4.21.64, e.g. from SIGMA-ALDRICH™ or PROMEGA™, UNIPROT™ P06873) which is a broad-spectrum and robust serine protease. Detergents may also be used to degrade (as well as inactivate) the polymerase.

As referred to herein "removing" the polymerase refers to spatially separating the polymerase from the ddNTP and/or the double stranded polynucleotide. This may be achieved by collection of the ddNTP and/or double stranded polynucleotide or alternatively by collection of the polymerase. Thus, for example, the mixture may be subjected to purification techniques allowing the separation of the different components (e.g. column chromatography or affinity separation). By way of example, antibodies to the polymerase, which may be attached to a solid support (e.g. magnetic beads), may be used to bind to the polymerase and allow its separation from the remainder of the mixture. Alternatively, chemical methods of removal may be used, e.g. extraction in an organic solvent such as chloroform.

To effectively remove the polymerase, as mentioned above, the double stranded polynucleotide may be collected (also effectively removing the ddNTP or separating the molecules). In a preferred method this is achieved by affinity binding, e.g. by use of binding partners (as described and defined hereinafter), one of which is attached to the double stranded polynucleotide, which together form a binding pair. In a preferred embodiment the binding pair may be biotin: streptavidin. For example, the double stranded polynucleotide may carry a biotin (e.g. at the 5' end of one of the strands of the double stranded polynucleotide) and may be collected by affinity binding to streptavidin which may be carried on a solid support, such as magnetic beads. The step of removing the polymerase (or ddNTP) may thus comprise separating said one or both strands of the double stranded polynucleotide from the polymerase or ddNTP by affinity binding as described above. In methods described hereinafter in which the double stranded polynucleotide is made up of a labelling probe and a reporter probe, the labelling probe or the reporter probe (preferably the former) may carry the binding partner discussed above. In this case removal of said polymerase or ddNTP comprises separating said labelling probe and/or reporter probe from said polymerase or ddNTP by affinity binding.

In an alternative method, the ddNTPs may be dephosphorylated. This method is preferably used when inappropriate covalent binding is likely. Suitable phosphatases are from classification EC 3.1.3.1 and include shrimp alkaline phosphatase (SAP) (e.g. available from SIGMA-ALDRICH™ or AFFYMETRIX™, UNIPRO™ Q9BHT8) and calf intestinal phosphatase (CIP) (e.g. available from PROMEGA™ or AFFYMETRIX™, UNIPRO™ P19111) and FastAP (available from THERMO SCIENTIFIC™).

Binding of the ddNTP may be prevented by removal of the ddNTP from the double stranded polynucleotide, e.g. by physical separation of the molecules, or by competition with other ddNTPs. The ddNTP may be removed by any appropriate means, e.g. the double stranded polynucleotide may be removed/separated from the ddNTP by collection of the double stranded polynucleotide as described hereinbefore.

Reference to "outcompeting" refers to providing sufficient amounts of the other ddNTPs such that binding of the ddNTP to the double stranded polynucleotide is reduced or prevented. The ddNTPs to be used to prevent or reduce binding are necessarily different to the ddNTP whose binding is to be prevented and may correspond to a different base (e.g. ddATP instead of ddGTP, preferably unlabelled or carrying a different label) or may correspond to the same or a different base but not carry a label (e.g. a labelled ddNTP may be outcompeted by unlabelled ddNTPs).

As described above, binding of the ddNTP can also be avoided by using a polynucleotide with a single stranded region which is at least 1 nucleotide in length (3' protruding) or at least 2 nucleotides in length (5' protruding) and/or using a polynucleotide with a single stranded region at one or both of the polynucleotide's ends which is at least one nucleotide in length and said single stranded region results, at least in part, from a mismatch between one or more base pairs in said polynucleotide. This protocol may be used as an alternative (or in addition) to the treatment of the polymerase and/or ddNTPs. In methods in which these latter treatments are used the single stranded region is preferably from 1-5 nucleotides in length, preferably 1, 2 or 3 nucleotides in length. However, when the length of the single stranded region is to be used as the sole mechanism to prevent ddNTP binding (or in conjunction with the above described methods), the single stranded region is preferably at least 2 nucleotides in length, preferably from 2-20 (or 2-30), e.g. from 3-15 or 4-10 nucleotides in length (especially preferably 2, 3 or 4 nucleotides in length). Preferably, in methods of preventing binding of a ddNTP to a polynucleotide in the presence of a polymerase the single stranded region has up to 10 nucleotides. This ensures that the single stranded regions are less susceptible to the undesirable binding of the ddNTP and/or reduces the influence of the ddNTP (e.g. if it is labelled and interacts with a label elsewhere in the double stranded molecule its influence may be reduced by increasing its distance from the other label).

One mechanism for introducing single stranded regions, e.g. at either or both ends of an otherwise blunt-ended double stranded polynucleotide, or to increase the length of an existing single stranded region, is to introduce mismatches at the end of the hybridizing region of the double stranded polynucleotide. Thus, for example, instead of using a blunt-ended double stranded polynucleotide, one or more mismatches may be introduced into one of the polynucleotides forming the double stranded polynucleotide. As used herein a "mismatch" refers to a base which does not exhibit complementary binding to the base with which it is paired when formed in the double stranded polynucleotide. "Base pairs" are a pair of bases in different polynucleotides which are brought into proximity when those polynucleotides are hybridized to one another and if complementary would bind to one another.

Preferably the one or more mismatches are at the end of the double stranded region, e.g. at one or more bases at one or both of the ends of the double stranded region. However, mismatches which have the effect of disrupting binding between complementary bases at one of the ends of the double stranded region may also be used. Preferably at least one, but preferably 2 (e.g. 1, 2, 3 or 4) or more bases are altered to provide mismatched bases. In particular, such methods may be used in methods described hereinafter in which the double stranded polynucleotide comprises a labelling probe and a reporter probe. A single stranded region generated by use of mismatches leads to a "protruding" strand even when the single stranded polynucleotides making up the double stranded polynucleotide are of the same length, i.e. the lack of binding between the base pairs leads to a protruding strand. The protruding strand is both 3' and 5' in view of the lack of binding between the base pairs. In a preferred feature the single stranded region is formed solely by the use of mismatches, but the use of mismatches to extend the single stranded region is also contemplated. As referred to herein a single stranded region which results "at least in part" from a mismatch defines the extent of the contribution of the mismatch to the single stranded region. Thus, the mismatch(s) may generate the single stranded region in its entirely or be responsible for only part of that region, e.g. up to 3, e.g. 1, 2 or 3 nucleotides of a longer single stranded region.

As noted above, the method may additionally comprise the step of generating the double stranded polynucleotide by contacting a first and second polynucleotide under conditions allowing their hybridization. The first and second polynucleotide have the definitions described hereinafter. In this case, the step of inactivating, degrading or removing said polymerase, dephosphorylating or removing said ddNTP, outcompeting said ddNTP and/or using a polynucleotide with a single stranded region which is at least 1 nucleotide (3' protruding) or 2 nucleotides (5' protruding) in length and/or using a polynucleotide with a single stranded region at one or both or the polynucleotide's ends which is at least one nucleotide in length and said single stranded region results, at least in part, from a mismatch between one or more base pairs in said polynucleotide may be performed before, during and/or after said double stranded polynucleotide is generated. If performed before the production of the double stranded molecule this avoids the generation of covalent bonds that can not later be severed. Later use of the treatment may avoid the non-covalent ddNTP binding and direct polymerase effects but not covalent binding of ddNTP. In this context the reference to preventing binding of a ddNTP to a (double stranded) polynucleotide in the presence of a polymerase, and the reference to the form that polynucleotide takes concerns the double stranded polynucleotide that will form, even if not yet formed at the time the treatment is undertaken.

In one aspect the ddNTP carries a label. As referred to herein, a "label" is any molecule or group of molecules which is detectable and/or generates a signal directly or indirectly. Convenient labels include colorimetric, chemiluminescent, chromogenic, radioactive and fluorescent labels. As discussed above, in a preferred feature the ddNTP carries a first label and the polynucleotide carries a second label. These labels are not the same. The first or second label affects the signal generated by the other label when the labels are in proximity to one another.

As referred to herein the "signal" of the label is a physical signal which may be detected, e.g. magnetism, optical activity, fluorescence, colour and so on, depending on the nature of the label used. The absence, presence or level of the signal may be determined.

In a preferred aspect, the first or second label is a fluorophore and the other label is a molecule which affects the fluorescence of the fluorophore when in proximity to that fluorophore and may itself be a fluorophore in one embodiment of the invention.

The above described influence on the signal (e.g. fluorescence) is only observed when the first and second labels are in sufficient "proximity" to one another. The proximity between the labels refers to the spatial distance between the labels. The proximity at which an influence on the signal (e.g. fluorescence) is observed may differ depending on the choice of labels. The influence on the signal (e.g. fluorescence) is observed when the labels are present on nucleotides which are involved in base pairing binding to one another (i.e. complementary binding nucleotides) or on adjacent nucleotides in a polynucleotide. In addition the influence on the signal (e.g. fluorescence) may be observed when the labels do not appear on complementary binding or adjacent nucleotides but instead appear on a nucleotide one to 30 (preferably 1-5, e.g. 1, 2 or 3) nucleotides away from the complementary or adjacent nucleotide when considering a linear molecule without tertiary structure. Thus for example the influence may be observed when the first label appears on nucleotide 1 which binds to nucleotide 1' in a complementary sequence but the second label appears at nucleotide 5' in the complementary sequence. In practice, an influence on the signal (e.g. fluorescence) may (also) be observed when the labels are separated by a large distance in a sequence (e.g. more than 30 nucleotides away), but the labels come into closer proximity (e.g. of the distance mentioned above) in view of the tertiary structure of the molecule on which the labels are found.

As referred to herein a "fluorophore" is is a fluorescent chemical compound that can re-emit light upon light excitation at a particular wavelength. This light may be detected during methods of the invention and provides a measurable signal relating to the presence and quantity of the labeled molecule.

The molecule (label) which affects the signal generated by the other label, when in proximity, increases or decreases the level of measurable signal. In a preferred aspect, the molecule which affects the fluorescence of the fluorophore when in proximity to that fluorophore either increases or decreases the fluorescence (i.e. amount of light emitted) of the fluorophore when in proximity to that fluorophore. For example a quencher may be used which decreases the fluorescence intensity of the fluorophore. This is achieved by the excited fluorophore returning to its ground state after activation by transferring its energy to the quencher, without the emission of light, while the quencher is promoted to its excited state. The quencher may itself be a fluorophore or may instead be a non-fluorophore. In a preferred aspect, fluorescence resonance energy transfer (FRET) is used in which the fluorophore transfers energy to the quencher (which itself is a fluorophore). In order for this to happen, the emission spectrum of the fluorophore must overlap with the absorption spectrum of the quencher. If the quencher is also a fluorophore, light emission from that molecule (at a specific wavelength) may be used as an indication that quenching (of the signal of the first fluorophore) has occurred. Alternatively dark quenchers may be used which absorb excitation energy from a fluorophore but dissipate that energy as heat rather than light.

Suitable fluorophores for use in the invention are provided in the table below (any one of these fluorophores may be used in methods of the invention:

TABLE 1

Fluorophore labels

| Fluorophore | Fluorophore Alternative | Excitation (nm) | Emission (nm) |
|---|---|---|---|
| LC Cyan500 | | 450 | 500 |
| FAM | | 495 | 515 |
| BODIPY-FL | | 503 | 512 |
| TET | CAL Fluor Gold 540 A | 525 | 540 |
| Yakima Yellow | | 530 | 549 |
| HEX | JOE, VIC B, CAL Fluor Orange 560 A | 535 | 555 |
| Cy3 C | NED B, Quasar 570 A, Oyster 556 D | 550 | 570 |
| ATTO550 | | 554 | 576 |
| TMR | CAL Fluor Red 590 A | 555 | 575 |
| Alexa Fluor 546 | | 556 | 573 |
| Alexa Fluor 555 | | 556 | 573 |
| ATTO565 | | 563 | 592 |
| TAMRA | | 565 | 580 |
| ROX | LC red 610 E, CAL Fluor Red 610 A | 575 | 605 |
| Texas red | LC red 610 E, CAL Fluor Red 610 A | 585 | 605 |
| Alexa Fluor 633 | | 621 | 639 |
| LC red 640 E | CAL Fluor Red 635 A | 625 | 640 |
| Cy5 C | LC red 670 E, Quasar 670 A, Oyster 645 D, Cy5 | 650 | 670 |
| LC red 705 E | Cy5.5 C, Cy5.5 | 680 | 710 |

The fluorophores are available from various commercial sources including BIOSEARCH TECHNOLOGIES™, GE HEALTHCARE™, LIFE TECHNOLOGIES™, INTEGRATED DNA TECHNOLOGIES™, Epoch Biosciences, Inc. and Atto-tec GmbH.

By selection of appropriate fluorophores, these fluorophores may also provide a fluorophore:quencher couple. However, examples of other suitable quenchers are provided below which include dark quenchers. The invention may be performed with any of the quenchers described herein.

TABLE 2

| Quenchers | |
|---|---|
| Quencher | Absorption Maximum (nm) |
| DDQ-I A | 430 |
| Dabcyl | 475 |
| Eclipse B | 530 |
| Iowa Black FQ C | 532 |
| BHQ-1D | 534 |
| ATTO540Q | 542 |
| QSY-7 E | 571 |
| BHQ-2 D | 580 |
| ATTO580Q | 586 |
| ATTO612Q | 615 |
| DDQ-II A | 630 |
| Iowa Black RQ C | 645 |
| QSY-21 E | 660 |
| DYQ660 | 660 |
| DYQ661 | 662 |
| BHQ-3 D | 670 |

The quenchers are available from various commercial sources including Eurogentec, Epoch Biosciences, Inc., INTEGRATED DNA TECHNOLOGIES™, BIOSEARCH TECHNOLOGIES™, LIFE TECHNOLOGIES™ and Attotec GmbH.

Preferred labels for use in the invention include TAMRA, BODIPY and FAM all of which are readily commercially available. In a preferred feature the two labels to be used are TAMRA and FAM, e.g. on the ddNTP and double stranded polynucleotide (or reporter probe, discussed hereinafter), respectively. Other preferred combinations of dark quencher and fluorophore include ATTO540Q/FAM, ATTO540Q/Yakima Yellow, ATTO580Q/ATTO550 and ATTO580Q/ATTO565. Other preferred combinations included ATTO612Q/ATTO565, ATTO612Q/ROX, ATTO612Q/CY5, ATTO612Q/CY5.5, DYQ660/ATTO565, DYQ660/ROX, DYQ660/CY5, DYQ660/CY5.5. Preferably the second label on the double stranded polynucleotide is a fluorophore and the first label on the ddNTP is the label that affects the fluorescence of the fluorophore.

Labels may be attached to the ddNTP by techniques well known in the art. The labeled polynucleotide may be prepared using labeled nucleotides by techniques well known in the art. Such molecules are readily available commercially. The polynucleotide may be labeled on any of its nucleotides. However, preferably the polynucleotide is labeled at one of the three nucleotides at the 5' terminus of one of its strands. Especially preferably it is labeled at the 5' end (i.e. the terminal 5' nucleotide) of one of the strands making up the polynucleotide.

Labelling may be direct (e.g. the label is attached directly to the ddNTP or polynucleotide thorough appropriate coupling chemistries or through a linker) or may be attached through binding partners. These may give rise to a covalent or non-covalent association. In this case the first binding partner of a binding pair is attached to the ddNTP or the polynucleotide and the second binding partner of the binding pair carries the label. As referred to herein a "binding pair" refers to a pair of molecules which form a specific and stable interaction. Examples included DNA:DNA, ligand:receptor, antibody:antigen interactions. Such binding moieties are well known in the art e.g. biotin/streptavidin.

The double stranded polynucleotide may take various forms. In particular, unless the polynucleotide is made up of single molecule, the double stranded molecule has various options at its ends. Thus, one or both ends of the double stranded polynucleotide may be blunt ended. One or both ends of the double stranded polynucleotide may have a 5' protruding end. One or both ends of the double stranded polynucleotide may have a 3' protruding end. Thus, for example, both ends may be blunt ended, or one end may be blunt ended and the other end may have a 5' protruding end. As described above, it has been found that ddNTP will bind to double stranded molecules as a result of various different mechanisms and that the mechanism that occurs is influenced by the type of ends present on the double stranded polynucleotide.

As referred to herein "blunt" ends refers to complementary base pairing occurring to the relevant end of the double stranded molecule, i.e. to leave no unpaired terminal base. "3' or 5' protruding ends" refer to the presence of one or more unpaired terminal bases which result in an overhang. A 5' protruding end has at its terminus a 5' unpaired base, i.e. at the 5' phosphoryl end. When a mismatch appears at the end of a double stranded molecule, this may result in both a 3' and 5' protruding end at that end of the molecule.

Although not wishing to be bound by theory it appears that blunt ends may allow non-covalent binding of the ddNTP to the double stranded polynucleotide with the polymerase acting as a mediator or adaptor for the binding and also allow covalent binding of the ddNTP to the double stranded polynucleotide by virtue of terminal transferase activity of the polymerase. Thus steps to prevent this binding are focused on removal of the polymerase or its activity (e.g. enzymatic or DNA binding) or the ddNTP. Thus, in a preferred aspect, when one or both ends of said double stranded polynucleotide is blunt ended the method comprises inactivating, degrading or removing said polymerase; desphophorylating or removing said ddNTP and/or outcompeting said ddNTP with another ddNTP.

Similarly, it appears that 5' protruding ends may allow non-covalent binding of the ddNTP to the double stranded polynucleotide with the polymerase acting as a mediator or adaptor for the binding and also allow covalent binding of the ddNTP to the double stranded polynucleotide by virtue of terminal transferase activity of the polymerase or by promiscuous incorporation of non-complementary ddNTP by the polymerase. Thus steps to prevent this binding are focused on removal of the polymerase or its activity or the ddNTP. The 5' protruding end may also be lengthened to diminish the non-covalent binding. Thus, in a further preferred aspect, when one or both ends of said double stranded polynucleotide has a 5' protruding end the method comprises inactivating, degrading or removing said polymerase; dephosphorylating or removing said ddNTP, outcompeting said ddNTP with another ddNTP and/or using a polynucleotide with a single stranded region which is at least 2 nucleotides (5' protruding) in length. Alternatively a polynucleotide may be used which has a single stranded region at one or both of the polynucleotide's ends which is at least one nucleotide in length to form a 5' protruding strand and said single stranded region results, at least in part, from a mismatch between one or more base pairs in said polynucleotide.

Finally, it appears that 3' protruding ends may allow non-covalent binding of the ddNTP to the double stranded polynucleotide with the polymerase acting as a mediator or adaptor for the binding. Thus steps to prevent this binding are focused on removal of the polymerase or its activity or the ddNTP or lengthening the 3' protruding end to diminish the non-covalent binding. Thus, in a yet further preferred aspect, when one or both ends of said double stranded polynucleotide has a 3' protruding end the method comprises inactivating, degrading or removing said polymerase; dephosphorylating or removing said ddNTP, outcompeting said ddNTP with another ddNTP and/or using a polynucleotide with a single stranded region which is at least 1 nucleotide (3' protruding) in length. Alternatively a polynucleotide may be used which has a single stranded region at one or both of the polynucleotide's ends which is at least one nucleotide in length to form a 3' protruding strand and said single stranded region results, at least in part, from a mismatch between one or more base pairs in said polynucleotide.

Methods in which the polymerase is removed, denatured or inactivated also serve to remove any direct polymerase-dependent effects such as false FRET effects.

As described hereinbefore, ddNTPs are used in various methods in which the ddNTP binds to a complementary nucleotide particularly in methods of chain extension under the control of a relevant enzyme such as a polymerase. In particular in this method, and other methods of the invention, the double stranded molecule is subjected to dissociation, as described hereinafter, preferably wherein the dissociation is achieved by heating and the double stranded polynucleotide is subjected to melting curve analysis. Thus in a preferred method said method comprises melting curve analysis. Frequently that ddNTP is labeled, e.g. in sequencing reactions. The above described method that may be used to prevent inappropriate ddNTP binding is therefore particularly useful in preventing the generation of a false positive, particularly in a sequence detection method.

Thus in a further preferred aspect, the present invention provides a method of avoiding false positives in a sequence detection method, wherein said sequence detection method comprises the step of bringing into contact a ddNTP, a polymerase and a first and second polynucleotide which hybridize to one another to form a third polynucleotide which is a double stranded polynucleotide with an optional single stranded region, wherein when said single stranded region provides a 5' protruding sequence it does not contain a base complementary to said ddNTP immediately adjacent to the double stranded region, wherein said method prevents binding of a ddNTP to said third polynucleotide by a method which (i) comprises inactivating, degrading or removing said polymerase, dephosphorylating or removing said ddNTP and/or outcompeting said ddNTP with another ddNTP and/or (ii) uses a polynucleotide with a single stranded region which is at least 1 nucleotide (3' protruding) or 2 nucleotides (5' protruding) in length and/or uses a polynucleotide with a single stranded region at one or both of the polynucleotide's ends which is at least one nucleotide in length and said single stranded region results, at least in part, from a mismatch between one or more base pairs in said polynucleotide.

In a preferred aspect, the step of inactivating, degrading or removing said polymerase, dephosphorylating or removing said ddNTP, outcompeting said ddNTP and/or using a polynucleotide with a single stranded region which is at least 1 nucleotide (3' protruding) or 2 nucleotides (5' protruding) in length and/or using a polynucleotide with a single stranded region at one or both of the polynucleotide's ends which is at least one nucleotide in length and said single stranded region results, at least in part, from a mismatch between one or more base pairs in said polynucleotide is performed before, during and/or after said double stranded polynucleotide (third polynucleotide) is generated.

This method comprises a method of preventing binding of a ddNTP to a polynucleotide in the presence of a polymerase, as described hereinbefore.

The definitions and preferred options provided hereinbefore are equally applicable to this method. In particular the single stranded region, steps (i) and (ii) and polymerase are as described hereinbefore. The "first" and "second" polynucleotides correspond to the first and second strands discussed above and may be present on a single polynucleotide but preferably are provided on separate molecules. The third polynucleotide which is a double stranded polynucleotide corresponds to the double stranded polynucleotide described hereinbefore. The ddNTP and double stranded polynucleotide may be labelled as described hereinbefore. The treatments to be used and the types of double stranded molecules to which they apply are also applicable to this method.

As referred to herein a "false positive" is a result that indicates that an attribute that a test is designed to identify is present when it is not. This also extends to false, apparent, increases in an attribute which may be present but not to the extent indicated by the result. In the case of a sequence detection method, a false positive corresponds to the identification of a particular nucleotide, base or sequence where that nucleotide, base or sequence is not present, e.g. a test polynucleotide is found to contain an SNP using the method but that SNP does not actually appear in the test polynucleotide.

A "sequence detection method" as used herein refers to a method in which a nucleotide sequence is determined. A full or partial sequence may be determined. In some cases only a single base or bases (or nucleotide(s)) in a sequence may be determined, though generally this is in the context of a surrounding sequence, and thus, for example, the test confirms the presence or absence of the SNP in its context sequence. Depending on the method used at least one nucleotide/base is determined, e.g. at least 2, 3, 10, 20, 30, 40, 50, 60, 70, 80, 90, 100, 200, 300, 400, 500, 600, 700, 800, 900, 1000, 2000, 4000, 6000 or 10000 or more nucleotides may be determined, particularly when multiple cycles of the method are used.

Determination of the nucleotide sequence includes the identification of the specific base at a particular position (i.e. A, T/U, G or C), i.e. absolute identification, or provides partial identification of that base, e.g. the method may identify a set of bases, of less than 4, (i.e. 3 or 2) which consists of the options for that base, e.g. A or T, but not G or C, or A, T or G but not C.

In this aspect of the invention the ddNTP, polymerase and first and second polynucleotides are brought into contact with one another. The first and second polynucleotides hybridize to one another to form the third (double stranded) polynucleotide. Thus, at least the first and second polynucleotides are brought into contact under appropriate conditions (e.g. temperature, concentration, buffer conditions) allowing their hybridization. The ddNTP and polymerase are also brought into contact with these molecules (i.e. allowed physical contact with these molecules in the same reaction vessel). The ddNTP and/or polymerase may be added to (or present in) the reaction mix at the same time as the first and second polynucleotides are brought into contact with one another or may be added to the reaction mix after one or both of the first and second polynucleotides have been added to the mixture, i.e. the four elements may be added to the reaction mix in any order, either consecutively or simultaneously (2 or more of the four elements). The step of inactivating, degrading or removing said polymerase, dephosphorylating or removing said ddNTP, outcompeting said ddNTP and/or using a polynucleotide with a single stranded region which is at least 1 nucleotide (3' protruding) or 2 nucleotides (5' protruding) in length and/or using a polynucleotide with a single stranded region at one or both of the polynucleotide's ends which is at least one nucleotide in length and said single stranded region results, at least in part, from a mismatch between one or more base pairs in said polynucleotide. may be performed before, during and/or after said double stranded polynucleotide is generated. Thus, when a particular molecule is to be added, e.g. a phosphatase and/or protease and/or detergent, this may be added with the first reagents or at a later point in the reaction.

The method may also be performed in the presence of other reagents. As the method may follow or occur during a normal extension reaction other reagents used for that extension reaction, such as one or more dNTPs may also be present.

Preferred sequence detection methods are based on the incorporation of a labelled ddNTP into a chain extension reaction by a polymerase and include the Sanger dideoxy method and sequencing by stepwise ligation and cleavage. However, in a preferred aspect the method is used in which sequence detection involves the use of single-base primer extension reactions.

Thus, in a further preferred aspect, the present invention provides a method of identifying a target nucleotide sequence in a test polynucleotide comprising:

(a) contacting said test polynucleotide with a ddNTP and an unlabelled labelling probe, which probe hybridizes to said target nucleotide sequence, when present, immediately 5 to a base which is complementary to said ddNTP in said target nucleotide sequence, in the presence of a polymerase, wherein said ddNTP carries a first label and when said target sequence is present in said test polynucleotide said unlabelled labelling probe hybridizes to said test polynucleotide and is extended in the 3' direction by said polymerase to attach said labelled ddNTP to said unlabelled labelling probe to form a labelled labelling probe;

(b) separating the labelling probe, which may be labelled or unlabelled, from the test polynucleotide;

(c) hybridizing said labelling probe to a reporter probe carrying a second label to form a double stranded polynucleotide (as defined hereinbefore), wherein the first or second label affects the signal generated by the other label when the labels are in proximity to one another (wherein preferably said first or second label is a fluorophore and the other label is a molecule which affects the fluorescence of said fluorophore when in proximity to said fluorophore), wherein when said labelling probe is unlabelled, at the end closest to the second label said double stranded polynucleotide is (i) blunt ended; (ii) has a protruding 5' end or (iii) has a protruding 3' end, and at the end distal to the second label said double stranded polynucleotide is (i) blunt ended; (ii) has a protruding 5' end or (iii) has a protruding 3' end, wherein said protruding ends consist of a single stranded region and when said single stranded region provides a 5' protruding sequence it does not contain a base complementary to said ddNTP immediately adjacent to the double stranded region (preferably does not contain a base complementary to said ddNTP anywhere in said single stranded region);

(d) inactivating, degrading or removing said polymerase, dephosphorylating or removing said ddNTP which did not attach in step a), outcompeting said ddNTP with another ddNTP and/or using a labelling probe and reporter probe which when bound together provide a single stranded region which is at least 1 nucleotide (3' protruding) or 2 nucleotides (5' protruding) in length and/or using a labelling probe and reporter probe which when bound together provide a single stranded region at one or both of the double stranded polynucleotide's ends which is at least one nucleotide in length and said single stranded region results, at least in part, from a mismatch between one or more base pairs in said double stranded polynucleotide, wherein step (d) may be performed before, during and/or after said double stranded molecule is generated; and (e) determining if said labelling probe carries a first label by assessing the signal associated with the double stranded polynucleotide, wherein a change in the first or second label's signal is indicative of the presence of said target sequence in said test polynucleotide.

In a preferred aspect of this method, depending on the form of the double stranded molecule that is generated, the method may be modified such that (i) when one or both ends of said polynucleotide is blunt ended according to step (c), in step (d) said polymerase is inactivated, degraded or removed, said ddNTP which did not attach in step a) is dephosphorylated or removed and/or said ddNTP is outcompeted with another ddNTP, (ii) when one or both ends of said polynucleotide has a 5' protruding end according to step (c), in step (d) said polymerase is inactivated, degraded or removed, said ddNTP which did not attach in step a) is dephosphorylated or removed, said ddNTP is outcompeted with another ddNTP and/or a labelling probe and reporter probe which when bound together provide a single stranded region which forms said 5' protruding end which is at least 2 nucleotides in length is used (which may be achieved using mismatch bases or by extending one of the probes, for example) and/or a labelling probe and reporter probe which when bound together provide a single stranded region at one or both of the double stranded polynucleotide's ends which is at least one nucleotide in length and said single stranded region results, at least in part, from a mismatch between one or more base pairs in said double stranded polynucleotide is used, and/or (iii) when one or both ends of said polynucleotide has a 3' protruding end according to step (c), in step (d) said polymerase is inactivated, degraded or removed (preferably degraded or removed), said ddNTP which did not attach in step a) is dephosphorylated, said ddNTP is outcompeted with another ddNTP and/or a labelling probe and reporter probe which when bound together provide a single stranded region which forms said 3' protruding end which is at least 1 nucleotide in length is used (which may be achieved using mismatch bases or by extending one of the probes, for example) and/or a labelling probe and reporter probe which when bound together provide a single stranded region at one or both of the double stranded polynucleotide's ends which is at least one nucleotide in length and said single stranded region results, at least in part, from a mismatch between one or more base pairs in said double stranded polynucleotide is used.

In the above method preferably said first or second label is a fluorophore and the other label is a molecule which affects the fluorescence of said fluorophore when in proximity to said fluorophore. In that case to determine if the labelling probe carries a first label, fluorescence of the fluorophore in the double stranded polynucleotide is assessed, wherein a change in fluorescence is indicative of the presence of said target sequence in said test polynucleotide.

The method of identifying a target nucleotide sequence, comprises a method of avoiding false positives in a sequence detection method, a method of preventing ddNTP and a method of avoiding false Tm readings or false FRET effects, as described herein. The meanings of the terms used in this aspect of the invention are as described hereinbefore or as further described hereinbelow.

As referred to herein, a "test" polynucleotide refers to a polynucleotide which is present in a sample which is to be examined by the method to determine if it contains (comprises or consists of) a target sequence. The "sample" is any sample which may be obtained or prepared that may contain a relevant polynucleotide. The polynucleotide may be provided in its original form, e.g. in a biological sample sourced from an organism, but more preferably is an amplified product of an original native polynucleotide. Thus, the test polynucleotide may be obtained by amplification of native RNA (e.g. mRNA or ribosomal RNA) or DNA to produce amplified cDNA for use in the method. Preferably the test polynucleotide is DNA or cDNA. The test polynucleotide may be double or single stranded.

The native RNA (which may first be reverse transcribed to cDNA) or DNA may be amplified by known amplification techniques such as the polymerase chain reaction (PCR) by the use of appropriate primers (e.g. forward and reverse), NASBA or ligase chain reaction. Alternatively, the native DNA or cDNA (or relevant parts thereof) may be cloned with a vector, used to transform a bacteria such as *E. coli* which may then be grown to multiply the nucleic acid molecules. When the sequence of the DNA or cDNAs are not known, primers may be directed to regions of the nucleic acid molecules which have been introduced. Thus for example, adapters may be ligated to the DNA molecules and primers directed to these portions for amplification of the DNA molecules. Alternatively, in the case of eukaryotic samples, advantage may be taken of the polyA tail and cap of the RNA to prepare appropriate primers.

The original native polynucleotide is obtained from an organism. This polynucleotide may be obtained directly e.g. from the human or non-human animal under investigation, e.g. from tissues, body fluid or body waste or in the case of prokaryotic organisms, from the organism itself. "Body fluids" include blood, saliva, spinal fluid, semen, lymph. "Body waste" includes urine, expectorated matter (pulmonary patients), faeces etc. "Tissue samples" include tissue obtained by biopsy, by surgical interventions or by other means e.g. placenta. These tissues, body fluid or body waste may provide the sample in which said test polynucleotide is present or from which said test polynucleotide may be derived, e.g. by amplification. In the alternative the sample may not be derived from the organism itself, but contains genetic material from that organism, e.g. an environmental sample (e.g. containing relevant cells or genetic material).

The organism of interest is a prokaryotic or eukaryotic organism which may be any eukaryotic organism such as human beings, other mammals and animals, birds, insects, fish and plants, and any prokaryotic organism such as a bacteria.

Preferred non-human animals include, but are not limited to fish and mammals. Preferred mammals include primates, domestic animals, livestock and laboratory animals. Thus preferred mammals include mice, rats, guinea pigs, cats, dogs, pigs, cows, goats, sheep and horses.

"Identifying a target nucleotide sequence" has the same meaning as used hereinbefore in relation to a sequence detection method, i.e. an absolute or partial sequence of at least one nucleotide within a sequence.

The "target" sequence is a sequence of interest to be identified in a test polynucleotide. The method may be used to identify a particular nucleotide (e.g. a SNP) (and this may be considered the sequence which is identified), but this will be in the context of its surrounding sequence and thus the presence of a target sequence is identified. Preferably the target sequence is from 6 to 30 nucleotides in length.

The "unlabelled labelling probe" (corresponding to the first polynucleotide described hereinbefore) is a polynucleotide which is capable of hybridizing to the target nucleotide sequence. The probe has a length as described hereinbefore which is sufficiently long to hybridize appropriately but specifically to the target sequence and not other sequences which may be present but sufficiently short to avoid excessive chemical synthesis. Some mismatching between the labelling probe and the target sequence contained in the test molecule may be tolerated. Preferably regions of the molecules (in the case of the labelling probe this may be all or a portion of that molecule) which are hybridized together have 100% complementarity to one another. However, this is not necessary and perfect base pairing is not necessary. Thus, mismatches within this region may be tolerated providing the two molecules are sufficiently complementary to allow the formation of a complex which is stable enough for performance of routine melting temperature analyses. Thus for example, the regions of the sequences which bind to one another, may share only 80, 90 or 95% complementarity (e.g. may have one, two, three or more mismatches). In some embodiments of the invention the use of mismatches is preferred as described herein.

The probe is unlabelled insofar as it does not carry a label as described hereinbefore which generates a detectable signal.

"Hybridizing" sequences are those which remain bound under conditions of high stringency, i.e. bind under non-stringent conditions (for example, 6×SSC/50% formamide at room temperature) and remain bound when washed under conditions of high stringency (2×SSC, 65° C.) (where SSC=0.15M NaCl, 0.015M sodium citrate, pH 7.2, e.g. for use with oligonucleotides with 70 or more nucleotides), (or TMACl wash solution at 50-80° C.) (where TMACl wash solution=3.0 M TMACl, 50 mM Tris-Cl (pH 8.0), 0.2 mM EDTA (pH 7.6), 1 mg/ml SDS, e.g. for use with oligonucleotides of between 17 and 50 nucleotides).

The labelling probe binds to said target nucleotide sequence immediately 5' (i.e. upstream) to a base which is complementary to the ddNTP used in the method. Thus, the labelling probe binds to only a portion of the target nucleotide sequence. When the target sequence contains a SNP, the labelling probe may bind to the full target nucleotide sequence, except the base at which the SNP occurs. In this case a double stranded molecule is formed to which the ddNTP may then be bound by a normal chain extension reaction. As referred to herein binding immediately 5' to the base refers to binding to the target sequence such that the final 3' end nucleotide of the labelling probe binds to a nucleotide in the target sequence which is adjacent to, and 5' of, the base which is complementary to the ddNTP. This allows for chain extension to occur at, at least, this complementary base. As discussed hereinbelow chain extension beyond this first nucleotide is also contemplated.

The labelling probe is preferably at least 5 nucleotides, preferably from 5 to 200 nucleotides, e.g. from 10-100 nucleotides, e.g. from 20-50 nucleotides in length.

The labelling probe may not be perfectly complementary to the target sequence (as discussed hereinbefore in relation to binding between the first and second strands in the double stranded polynucleotide). The number of bases involved in complementary binding must be sufficient to allow the production of a stable complex. Preferably at least 5 consecutive bases, preferably from 5 to 200 consecutive bases, e.g. from 10-100 consecutive bases, e.g. from 20-50 consecutive bases of the labelling probe are complementary to bases in the target sequence. Preferably, the labelling probe is perfectly (i.e. 100%) complementary to the target sequence or a region thereof.

As referred to herein "complementarity" defines the relationship between two molecules (or regions thereof) and denotes the extent to which the molecules contains complementary nucleotides/bases in such a way that complementary binding between the molecules may occur, i.e. the complementary bases are provided in the same order. When sequences have 100% complementarity they bind with no mismatches. When they have less than 100% complementarity, one or more mismatches are present.

The ddNTP, polymerase, first and second label are as described hereinbefore. The second label binds to the reporter probe.

When the target sequence is present the unlabelled labelling probe hybridizes to the test polynucleotide and is extended in the 3' direction by the polymerase to attach the labelled ddNTP to the unlabelled labelling probe to form a labelled labelling probe. To allow this to be achieved the labelling probe, ddNTP and polymerase are provided under appropriate conditions (e.g. temperature and concentration) and for the time appropriate to allow both hybridization and chain extension. Appropriate conditions for this purpose are well known in the art (see e.g. Sambrook et. al. (1989), Molecular Cloning: A laboratory manual, 2nd Ed., Cold Spring Harbor Laboratory Press, Cold Spring Harbor, N.Y.)

The labelled labelling probe thus formed is a single stranded polynucleotide into which the labelled ddNTP has been incorporated by chain extension. The ddNTP may be incorporated as the first nucleotide in the chain extension reaction or may be incorporated as a second or subsequent nucleotide (e.g. when dNTPs are also used).

When the target sequence is not present, e.g. if a particular SNP is not present, the labelling probe may still bind to the test polynucleotide (in the case of a SNP, the majority of the target polynucleotide sequence may be present (i.e. its upstream context sequence), even if the particular SNP is not) but no chain extension occurs and thus the labelling probe remains unlabelled.

Separation of the labelling probe from the test polynucleotide requires at least disruption of the base pair binding between these molecules, i.e. melting of the hybridized complex. Conveniently this may be achieved by raising the temperature of the solution in which the complex is held to above the melting temperature (Tm, discussed below) of that complex.

Although not necessary, further physical separation of the labelling probe and the test polynucleotide may be performed. (Nevertheless, in a preferred aspect, further physical separation of the molecules into separate areas or solutions is not performed, e.g. no separation based on charge or size, to separate the different molecules and unbound ddNTP, is performed.) This may be achieved, for example, by affinity, e.g. wherein the labelling probe or test polynucleotide contains a sequence or molecule (e.g. introduced during preparation or amplification) which is not present on the other entity (labelling probe or test polynucleotide) and to which a binding partner (e.g. attached to a solid support) may be provided. For example, as described hereinbefore, the labelling probe may carry a binding partner and may be collected by binding that binding partner to the other binding partner of the binding pair which may be carried on a solid support.

Once separated from the test polynucleotide the (labelled or unlabelled) labelling probe is hybridized to a reporter probe with a second label. Hybridization and the second label are as described hereinbefore. The double stranded polynucleotide that is formed by this hybridization is also as described hereinbefore.

The (labelled and unlabelled) labelling probe and the reporter probe correspond to the first and second polynucleotide as described herein which when hybridized together form the third polynucleotide (the double stranded polynucleotide described hereinbefore). The definitions provided for these polynucleotides as set forth hereinbefore are thus applicable. Thus, for example the reporter probe is preferably 5 nucleotides in length, preferably from 5 to 200 nucleotides, e.g. from 10-100 nucleotides, e.g. from 20-50 nucleotides in length and is labelled with a second label which is preferably the fluorophore. The reporter probe may be labelled at any nucleotide within the probe molecule providing the first and second label are selected such that the required interaction can be achieved based on their proximity. Preferably the reporter probe is labelled at the 5' end, e.g. at one of the three nucleotides at the 5' end, e.g. at the 5' terminus.

In the design of the labelling probe and reporter probe, bases which would produce intrinsic quenching activity (e.g. as shown in the Examples) should be avoided. Thus, guanine residues in close proximity to the label whose signal is to be measured should be avoided. Thus, if the reporter molecule carries a label at its 5' end, a labelling probe with a G-rich 3'-end should be avoided. Furthermore, 5' guanines should be avoided in the reporter molecule.

The double stranded polynucleotide thus formed has blunt or protruding strands, which have the meaning described hereinbefore, at one or both ends. The end closest to the second label is the end closest to the nucleotide on which the label is carried. In a preferred feature the second label appears at the 5' end on the reporter probe and binding of the labelling probe at this (closest) end generates a blunt or protruding end. The end distal to this label, in this case, is at the 3' end of the reporter probe.

In a preferred feature the single stranded region of the protruding strand is one, two or three nucleotides in length.

Dependent on the type of end (blunt or protruding) the double stranded polynucleotide may be treated as described hereinbefore i.e. by treatment or removal of the polymerase, dephosphorylation or removal of ddNTPs, outcompeting ddNTPs or use of a double stranded molecule with a longer single stranded region or mismatched bair pairs. As described above, different types of binding are mediated by the polymerase. Depending on the type of binding to be avoided, the timing of this treatment may be selected appropriately. The treatment may be performed before the double stranded molecule is generated (to avoid the inappropriate covalent binding of ddNTP) and/or the treatment may be performed during and/or after the generation of the double stranded molecule (but before signal detection), where the principle concern is false FRET effects or the stabilizing effects of the polymerase. Conveniently, the agent to be used for this purpose may be present during the generation of the double stranded molecule, e.g. a proteinase or detergent may be added at the same time as the double stranded molecule is generated. Particularly preferably, when a proteinase is used it is added prior to generation of the double stranded polynucleotide. Preferably, when detergent is used, in view of its more rapid effects, it may be added prior to, or during, generation of the double stranded polynucleotide.

After performance of this step, only labels which were present in the polynucleotides as originally prepared or introduced during the chain extension reaction which incorporated the ddNTP should be present. To determine if the target sequence is present it is necessary to determine whether the labelling probe carries a first label (i.e. the ddNTP has been incorporated, indicating the existence of the full target sequence).

This determination may be made by assessing the signal associated with the double stranded polynucleotide. Dependent on the label used and hence signal generated, appropriate methods of determination may be used. As referred to in more detail hereinbelow, for example, one of the labels may be a fluorophore and the extent of it signal (fluorescence) may be examined.

As referred to herein a "change in signal" refers to an alteration in the level (including presence or absence) or type of signal relative to a reference value. The alteration may be an increase or decrease of signal. When assessing whether formation of the double stranded polynucleotide results in a changed signal, the reference value is the signal of the first or second label when not in proximity to one another. Thus, for example in the case of a fluorophore and quencher, if the fluorophore is the second label present on the reporter probe, and the first label on the ddNTP is a quencher, when the ddNTP is incorporated into the labelling probe and that probe binds to the reporter probe such that the labels are in proximity, the signal from the fluorophore will be changed (i.e. the fluorescence will be quenched thus reducing the detectable fluorescence from that label).

The determination that is made may be qualitative (i.e. identifying the presence or absence of a test sequence) and/or quantitative (i.e. identifying the amount or level of the test sequence). This may be expressed as an absolute value, a percentage, a ratio or similar indicator.

The change in signal may be assessed relative to the starting, e.g. unbound signal of the label, e.g. the signal generated by the reporter probe. Conveniently, however, the change in signal is assessed by separating the reporter probe from the labelling probe (labelled or unlabelled) and assessing the change in signal during that dissociation. Conveniently this is performed using melting curve analysis.

Thus, in a preferred aspect, the present invention provides subjecting the double stranded molecule to dissociation wherein a change in the first or second label's signal (preferably fluorescence) during said dissociation is indicative of the presence of said target sequence in said test polynucleotide. Preferably the dissociation is achieved by heating and the double stranded polynucleotide is subjected to melting curve analysis.

In a preferred aspect, the level of fluorescence of the label which is a fluorophore (which is preferably on the reporter probe) is assessed. If the fluorophore is present on the reporter probe, fluorescence from that molecule will be present but may be affected depending on whether or not the first label is present on the labelling probe. If the fluorophore is present on the labelling probe (if labelled), fluorescence will be present only when that labelling probe is present, and that fluorescence will be affected by the presence of the second label on the reporter probe.

Any convenient means may be used to assess fluorescence of the fluorophore. For example, 2-photon and 3-photon time resolved fluorescence spectroscopy, fluorescence lifetime imaging or fluorescence resonance energy transfer may be examined. Fluorescence may be detected using appropriate detectors, e.g. fluorescent microscopes, fluorescence scanners, spectrofluorometers or flow cytometers. Conveniently spectrofluorometers are used. By way of example, conveniently, instruments such as the APPLIED BIOSYSTEMS™ 7500 Fast instrument or the QIAGEN™ Rotor-Q instrument, may be used.

In methods of multiplexing, as discussed in more detail hereinbelow, more than one fluorescent label may be used (e.g. if more than one labelling or reporter probe is used) and in that case a detector capable of discriminating between the fluorescence of different labels if required.

Preferably the method is automated or semi-automated for high throughput screening. The automation is conveniently controlled by computer software.

As described above, conveniently the determination is made by melting curve analysis. Melting curve analysis is an assessment of the dissociation-characteristics of double-stranded DNA during the process of heating. A rise in temperature leads to dissociation of the double stranded molecule into single strands as binding between the base pairs is disrupted. The melting temperature (Tm) is the temperature at which 50% of the double stranded molecules have dissociated into single stranded molecules. The melting temperature is affected by various factors including the extent of complementarity between the binding pairs, the length of the molecules involved and the GC content of the molecules, all of which affect the stability of the double stranded molecule.

In the present case the double stranded molecule has two different forms depending on whether the target sequence is present or not. When the target sequence is present the labelling probe is labelled with the first label. This is then bound to the reporter probe which has a second label. One of these labels affects the signal from the other label. Preferably one of these labels is a fluorophore and the other label affects its fluorescence. When the labelled labelling probe and reporter probe are bound, the labels are in sufficient proximity that the signal (e.g. fluorescence of the fluorophore) is affected. Thus, when these molecules are hybridized the signal (e.g. fluorescence of the fluorophore) is affected. However, when these molecules are dissociated (e.g. during the melting curve analysis), the labels are effectively separated such that the signal (e.g. fluorescence of the fluorophore) is unaffected. Thus, during the course of the melting curve analysis, as the molecules are dissociated, the signal (e.g. fluorescence from the fluorophore) changes. This may be monitored by assessing the signal (e.g. fluorescence) during the melting curve analysis. The melting curve analysis allows the identification of both whether the first and second labels were present together and the temperature at which the two polynucleotides carrying those labels dissociate. When both labels are present this is indicative that the labelling probe was labelled, i.e. that the ddNTP bound to the target sequence.

Instead of a heat-based dissociation method, alternative methods of dissociation may be used. Thus, for example, other denaturation methods may be used such as the use of NaOH, formamide or a single stranded binding protein to separate the labelling probe and reporter probe. These denaturants may be applied at different concentrations or over a time course at a single concentration. An electric field may be applied to assist denaturation. The progression of denaturation and dissociation of the two strands (and hence effects on the label's signal) may be monitored as appropriate by assessing the changes in signal (e.g. fluorescence) during dissociation, as described above. Such methods may be subjected to multiplexing as described herein as different complexes may dissociate at different times/concentrations in these methods, depending on the sequences of the strands making up the double stranded molecules.

Preferably, the labels used are a fluorophore and quencher. In this case, during melting curve analysis fluorescence will increase as the double stranded molecule dissociates and the fluorophore is separated from the quencher.

In a preferred aspect, the double stranded polynucleotide referred to herein (e.g. the molecule to be subjected to melting curve analysis is blunt ended and/or has a 5' protruding end at one of its ends (e.g. it may be blunt ended at both ends, have a 5' protruding end at both ends or have a blunt end at one end and a 5' protruding end at the other end). Where present the 5' protruding end preferably has a one, two or three nucleotide overhang. When mismatched base pairs are used, a 5' protruding end as well as a 3' protruding end may be present at one end of the double stranded polynucleotide.

As noted above, the presence of polymerase also raises the melting temperature of double stranded polynucleotides thus leading to a false Tm in melting curve analysis methods. Furthermore, it has been found that polymerase is responsible for false FRET effects (e.g. a false positive quenching effect) on fluorescent labels, even in the absence of another fluorescence donor or quenching molecule. This has the effect of producing false results in methods in which the level of fluorescence (which may be influenced by quenching and/or donor fluorescence) of a fluorescent label is used to identify or quantify an entity of interest, e.g. binding of a polynucleotide with a quenching molecule in close enough proximity to a polynucleotide carrying a fluorophore to affect the latter's fluorescence. Typically such effects may be monitored in a melting curve analysis method. Such effects may be overcome in the above described methods by inactivation, denaturation or removal of the polymerase.

Accordingly the present invention also provides a method of avoiding a false Tm reading, and/or false FRET effects (e.g. false positive quenching) (preferably in or comprising a melting curve analysis method), wherein said method comprises the step of bringing into contact a polymerase, optionally dNTP and/or ddNTP, and a first and second polynucleotide which hybridize to one another to form a third polynucleotide which is a double stranded polynucleotide with an optional single stranded region, wherein when false FRET effects (e.g. false positive quenching) is to be avoided said first polynucleotide carries a fluorophore, wherein said method further comprises inactivating, degrading or removing said polymerase prior to assessing Tm and/or FRET effects (e.g. prior to said melting curve analysis, when used), and/or, when false FRET effects (e.g. false positive quenching) are to be avoided and dNTP and/or ddNTP are used in said method dephosphorylating or removing said dNTP and/or ddNTP and/or outcompeting said dNTP and/or ddNTP with another dNTP and/or ddNTP, wherein said terms have the meanings as provided hereinbefore, except for said double stranded polynucleotide which preferably has the meanings described hereinbefore.

False FRET effects may be avoided by inactivating, degrading or removed said polymerase and/or removing and/or outcompeting said dNTP or ddNTP. The method of avoiding false FRET effects (e.g. false positive quenching) may be used in a melting curve analysis or other methods, as appropriate, e.g. in which an increase or decrease in the level of fluorescence of a fluorescent label is indicative of the presence (or amount) of a target molecule or sequence (for example methods using one or more probes or primers carrying a fluorescence donor or quencher whose proximity to the fluorescent label is indicative of the presence (or amount) of the target molecule or sequence). Such methods include the use of Taqman probes, scorpion probes and molecular beacons, for example. Melting curve analysis may be carried out as described hereinbefore.

When dNTPs are used in the above described method, they may be used as substitutes (or together with) ddNTPs which might otherwise be used in the method. Hence the teachings provided herein in relation to ddNTPs may apply similarly to dNTPs, as appropriate.

As referred to herein a "false Tm reading" refers to a different melting temperature observed when the method is conducted experimentally relative to an in silico calculation and which experimental result can be restored to the correct Tm reading by removal, inactivation or degradation of the polymerase. This can readily be identified experimentally, as shown in the examples, by using one of the protocols outlined above, to avoid the false reading e.g. performing Tm analysis in the presence of polymerase with or without a proteinase or detergent. Without wishing to be bound by theory it appears that the polymerase has a stabilizing effect and increases the Tm of the double stranded polynucleotide. This increase may be at least 1° C., preferably at least 3, 4 or 5° C., e.g. from 3 or 5-10° C. Said reading may not be directly assessed in said method, i.e. the precise Tm may not be assessed or recorded, but may instead be evident from an examination of the melting curve to the extent that a false Tm, e.g. the absence of a discernible peak or a peak overlapping with another peak, is evident. "Assessing" the Tm extends to such an observation.

As used herein, "false FRET effects" refers to an increase or decrease in the fluorescence of a fluorescent label not resulting from the presence of a quenching or fluorescence donor molecule. FRET as used herein refers to Fluorescence Resonance Energy Transfer. Thus, the polymerase may act as a quenching or fluorescence donor molecule (though it is not identified in the system as such). Such alterations in fluorescence may be an increase or decrease in fluorescence at a given temperature and/or wavelength. "Assessing" FRET effects extends to examining fluorescence during all of part of said method.

As used herein, "false positive quenching" refers to alterations (decreases) in fluorescence of a fluorophore not resulting from the presence of a quenching molecule. Thus, the polymerase may act as a quenching molecule (though it is not identified in the system as a quenching molecule).

The method of avoiding a false Tm reading is particularly effective on double stranded molecules in which both strands are less than 60 nucleotides in length, preferably less than 50, 40, 30 or 25 nucleotides, e.g. from 10-20 nucleotides in length. Preferably said method additionally comprises the step of generating the double stranded polynucleotide by contacting a first and second polynucleotide under conditions allowing their hybridization and preferably said step of inactivating, degrading or removing said polymerase or dephosphorylating or removing or outcompeting said dNTP or ddNTP is performed before, during and/or after said double stranded polynucleotide is generated and performed in accordance with a method described hereinbefore. Conveniently, the agent to be used for this purpose may be present during the generation of the double stranded molecule, e.g. a proteinase or detergent may be added at the same time as the double stranded molecule is generated. Preferably, in methods in which ddNTPs are also used, the detergent or proteinase is added before formation of the double stranded molecule to also prevent erroneous ddNTP incorporation. Particularly in the case of the proteinase, this is preferably added some time before the generation of the double stranded molecule in view of the slow action of the proteinase on the polymerase. Detergent, when used, may be added at a later stage in view of its rapid action, e.g. during formation of the double stranded molecule. One or more agent suitable for the above described purposes may be used in the method.

If a dNTP or ddNTP is used in the method the dNTP or ddNTP and polynucleotide may be labelled as described hereinbefore. However, when a dNTP or ddNTP is not used said first polynucleotide carries a first label as defined hereinbefore and optionally said first or second polynucleotide carries a second label as defined hereinbefore. False FRET effects (e.g. false positive quenching) are observed even in the presence of a fluorophore only and hence only a first label may be present in said method. In particular said fluorophore may be HEX or FAM, as described hereinbefore.

This method has utility in any method in which melting curve analysis is performed. Thus, for example in methods in which the presence of a target molecule carrying a fluorophore (or quencher) is identified or quantified based on whether or not its fluorescence is quenched (or it quenches the fluorescence of a fluorophore) indicative of its binding to a test molecule, the above method avoids false FRET results (e.g. false positive quenching results) from the presence of polymerase which may be present. Various methods employ fluorescence detection quenching to which these methods of the invention may be applied, e.g. molecular beacons or scorpion probes (in which both the quencher and fluorophore is carried on the test/probe), Taqman probes and particularly the above described method in which a first and second polynucleotide, one of which carries a quenching molecule and one carries a fluorophore are dissociated during heating and changes in fluorescence monitored. In such methods polymerase removal/inactivation/degradation is performed only once its required extension properties have been completed in the method.

The method is also of utility when Tm values are important for qualitative or quantitative determinations. Correct Tm values are particularly important when multiplexing is contemplated and peak separation is required to allow identification of different target molecules.

The effect of the polymerase on Tm values may also be taken into account in designing and performing methods in which melting temperature has a bearing on performance of the method or its results. Thus, for example, if polymerase is present during dissociation and association steps in a method its effects will need to be taken into account. For example, in PCR methods temperatures should be selected accordingly to take into account possible higher Tms of double stranded molecules which form during the process. The effect of Tm should also be used to interpret results in which higher than expected Tm values are observed.

The present invention also allows the selection of appropriate molecules for performance of the method or for assessing the extent of the influence of a polymerase in a particular method.

Thus, in a further aspect the present invention provides a method of assessing the effect of a polymerase on the melting temperature (Tm) and/or FRET (preferably quenching) of a double stranded polynucleotide with an optional single stranded region, wherein preferably said method is a melting curve analysis method, wherein said method is performed on two samples and for each sample the method comprises the step of bringing into contact said polymerase, optionally ddNTP and/or dNTP, and a first and second polynucleotide which hybridize to one another to form a third polynucleotide which is said double stranded polynucleotide, wherein when FRET effects are to be assessed said first polynucleotide carries a fluorescent label, wherein said method performed on only one of said samples further comprises inactivating, degrading or removing said polymerase prior to assessing Tm and/or FRET effects, and/or, when FRET effects are to be assessed and dNTP and/or ddNTP are used in said method dephosphorylating or removing said dNTP and/or ddNTP and/or outcompeting said dNTP and/or ddNTP with another dNTP and/or ddNTP, subjecting the two samples to melting temperature analysis and/or FRET analysis, and assessing whether the melting temperature and/or FRET effects differ between the two samples to determine the effect of said polymerase on the melting temperature and/or FRET of said double stranded polynucleotide, wherein preferably said double stranded polynucleotide, and/or preferably performance of the steps is as defined hereinbefore. The definitions of the polymerase, polynucleotides and other entities used in said method are as described herein.

The polymerase to be used in the method may be a test polymerase, e.g. a variant of a known polymerase to assess its FRET/Tm effects. This may be assessed relative to a known polymerase, e.g. the polymerase from which the variant is derived to assess if the variations result in any alterations in FRET/Tm effects. Alternatively the double stranded polynucleotide may be a test molecule to assess how its FRET/Tm is affected by the action of a polymerase. This may assist in design of molecules for use in sequencing and other methods in which FRET/Tm plays a role. Optionally the method includes comparing the results obtained to the results obtained with a control polymerase or polynucleotide.

The two samples which are used are essentially identical (i.e. the method is performed in duplicate), but only one of the samples is subjected to the step which serves to remove false FRET/Tm readings.

The Tm/FRET effect is assessed by measuring Tm or FRET effects as described herein. A different effect is observed if the Tm reading is different between the two samples or the presence or level of fluorescence is different.

Also provided in accordance with the invention are kits for putting the methods described herein into effect. Such kits may contain one or more of the following components: at least one ddNTP labelled with a first label (if more than one ddNTP is used the same label may be used or preferably a different label may be used, as described hereinbefore and hereinafter), at least one first polynucleotide (or labelling probe), at least one second polynucleotide (or reporter probe) labelled with a second label (if more than one second polynucleotide is used the same label may be used or preferably a different label may be used, as described hereinbefore and hereinafter), a polymerase, a means for inactivating the polymerase (e.g. a detergent such as SDS), a means for degrading the polymerase (e.g. a proteinase such as proteinase K or a detergent such as SDS), a means for removing the polymerase (e.g. an antibody specific for that polymerase or streptavidin-coupled magnetic beads if biotin-coupled labelling probes are used, thus separating them from the polymerase), a means for dephosphorylating the ddNTPs (e.g. a phosphatase such as shrimp alkaline phosphatase or calf intestinal phosphatase), a means for removing the ddNTPs (e.g. reagents for organic extraction, streptavidin-coupled magnetic beads if biotin-coupled labelling probes are used, thus separating them from the ddNTPs), unlabelled ddNTPs for outcompeting the labelled ddNTPs and other reagents useful for use in the method e.g. dNTPs and/or unlabelled ddNTPs.

These entities have the definitions and preferred options described hereinbefore.

Thus, in a preferred aspect, the present invention provides a kit comprising:

a) at least one ddNTP labelled with a first label, as described hereinbefore,
b) at least one first polynucleotide (or labelling probe) as described hereinbefore,
c) at least one second polynucleotide (or reporter probe) labelled with a second label, as described hereinbefore,
d) a polymerase, and at least one of:
   (i) a means for inactivating the polymerase (e.g. a detergent such as SDS),
   (ii) a means for degrading the polymerase (e.g. a proteinase such as proteinase K or detergent such as SDS),
   (iii) a means for removing the polymerase (e.g. an antibody specific for that polymerase or streptavidin-coupled magnetic beads if biotin-coupled labelling probes are used, thus separating them from the polymerase),
   (iv) a means for dephosphorylating the ddNTP (e.g. a phosphatase such as shrimp alkaline phosphatase or calf intestinal phosphatase),
   (v) a means for removing the ddNTPs (e.g. reagents for organic extraction or streptavidin-coupled magnetic beads if biotin-coupled labelling probes are used, thus separating them from the ddNTPs), and
   (vi) unlabelled ddNTP for outcompeting the labelled ddNTP;

wherein the first or second label affects the signal generated by the other label when the labels are in proximity to one another.

The first polynucleotide or labelling probe as used in the kit is capable of binding to a target nucleotide sequence. This target sequence, and hence the labelling probe, may be selected based on the intended utility of the kit. For the purposes of this embodiment, the labelling probe may be any oligonucleotide or polynucleotide to which a target sequence may exist.

Optionally the kit may also contain standardizing materials, e.g. mRNA or cDNA from normal and/or diseased organisms for comparative purposes, or reference test polynucleotides, primers for amplification and/or appropriate enzymes, buffers and solutions. Optionally said kit may also contain a package insert describing how the method of the invention should be performed, optionally providing standard graphs, data or software for interpretation of results obtained when performing the invention.

The use of such kits to identify a target nucleotide sequence in a test polynucleotide, as described hereinbefore, forms a further aspect of the invention.

By way of illustration, methods of putting the invention are described in more detail below. Whilst the invention is not limited to such methods, preferred aspects described herein are preferred aspects applicable to all methods described herein.

Identification of a target nucleotide sequence in a test polynucleotide includes the identification of multiple target nucleotide sequences in a test polynucleotide. The ability to identify multiple targets during a single method is referred to herein as multiplexing. Thus, the method allows multiplexing such that more than one target nucleotide sequence (e.g. more than 2, 4, 8 or 16) may be identified in a single method. This may be achieved by the use of different labels which have signals that may be discriminated. Thus, for example, if detection of the label is based on a fluorescence signal, different fluorescence labels may be selected which fluoresce at a different wavelength and may thus be discriminated.

The different target nucleotide sequences to be detected may be present in a single test molecule and/or in multiple discrete test molecules. When present in the same test molecule, the target nucleotide sequences may be at the same or different locations on the test molecule. When present at the same location the method is used to identify which of a number of possible sequences is present at the location, e.g. to detect the SNP allele (in this case differently labelled ddNTPs may be used). If the target sequence is not at the same location, different target sequences may be detected in a single method, e.g. multiple SNPs.

In a preferred aspect, therefore, the method is multiplexed by the use of more than one label (which have signals that may be discriminated). These different labels may appear on the ddNTPs and/or the labelled polynucleotides (e.g. the reporter probes). Where a pair of labels are used and the signal of one label affects the other when in proximity, multiple pairs of labels should be selected for multiplexing such that the resulting signals can be discriminated. For example, when a fluorophore and quencher are used, the resulting quenched and unquenched signals from each pair should be distinguishable from any signal generated by another pair of labels. A pair of labels may have one label in common with another pair of labels. Thus, for example, a common quencher may be used if it is able to quench the emission of two distinguishable fluorophores and the resultant quenched signals can be discriminated.

Thus, in preferred aspects of the invention, preferably at least two ddNTPs which are labelled are used, wherein preferably the first labels on the different ddNTPs are different. Further preferred embodiments include the use of at least two reporter probes (and/or at least two labelling probes), wherein preferably the second labels on the different reporter probes are different. In particular, multiple pairs of labels may be used, wherein each pair of labels comprises a first label on a ddNTP and a second label on a reporter probe, wherein each pair of labels is different to every other pair of labels, wherein preferably each pair contains first and second labels which are different to any first or second label found in any other pair of labels.

Methods of detection may allow other means of multiplexing the method. Thus, the resultant double stranded molecules may be discriminated not just based on the labels they carry, but also on the basis of the form of the double stranded molecule. This may relate to the sequence, length or other distinguishing features of the double stranded molecule. Different sequences may be used to provide a different property, e.g. ability to bind a partner (e.g. in affinity based methods), or to bind together the two strands of the double stranded molecule with greater or lower affinity. For example if the detection method is via melting temperature analysis, the double stranded molecules used in the method may be selected such that they have different melting temperatures. In this case, the labelling probe and reporter probe make up the double stranded molecule. These may be appropriately selected to provide a specific melting temperature (Tm), e.g. by their length or sequence. For example, Tm may be increased by selecting longer sequences, a higher GC content and/or high complementarity (e.g. at least 95, 96, 97, 98, 99 or 100%) between the sequences. Tm may be decreased by the use of shorter sequences, a lower GC content and/or lower than 100% complementarity (e.g. less than 95, 90 or 80%).

The different Tm values may be obtained by altering the properties of the reporter and/or labelling probes that are used. Thus, in one example, pairs of reporter and labelling probes may be used for detecting each test sequence, with each pair being different from any other pairs of probes used in the method and generating a complex (double stranded polynucleotide) that may be discriminated (e.g. in terms of their melting temperature) from any other complex formed by any other pair of probes. However, it is also possible to provide only one reporter (or labelling) probe but various forms of the other probe such that various complexes may be formed, each of which have different properties (e.g. melting temperature). In such methods the complexes would be distinguished by their label and hybridization properties, e.g. melting temperature.

Thus, in a preferred aspect, at least two reporter probes and/or at least two labelling probes are used and when the reporter probe(s) and labelling probe(s) are hybridized to one another they generate at least two double stranded polynucleotides with different melting temperatures. In a preferred aspect, multiple pairs of reporter and labelling probes are provided, wherein each pair of probes is different to every other pair of probes, wherein preferably the label of the reporter probe in each pair is different to the label of the reporter probe in any other pair of probes.

The sequences are selected to provide Tms that can be distinguished in a melting curve analysis, e.g. a Tm difference of from 0.1 to 40° C., preferably at least 3, 4, 5, 6, 7, 8, 9 or 10° C.

In a preferred aspect, methods of multiplexing are combined. Thus, for example, in the case of a melting curve analysis, 2 or more different pairs of first and second labels are used and 2 or more different melting temperatures are used. The use of 2 different pairs of first and second labels and 2 different melting temperatures allows 4 different sequences to be detected (i.e. if at each different melting temperature both pairs of labels are used). Multiplexing of 9 different sequences can readily be achieved using 3 different pairs of labels and 3 different melting temperatures and so on.

Thus, in methods of the invention, conveniently, more than one ddNTP labelled with a first label may be provided (preferably each ddNTP has a different first label). Thus, for example, each of ddATP, ddGTP, ddTTP (or ddUTP) and ddCTP may be provided with a different first label. The reporter probe (or second polynucleotide) may then be provided with four different second labels (as discussed above, some common labels may be used if the signals from the labels may still be discriminated between the different pairs). Multiple unlabelled labelling probes (or first polynucleotides) may be provided directed to different target nucleotide sequences, which may, when bound to the reporter probe (or second polynucleotide) be discriminated. This may be achieved by appropriate selection of the sequence and/or length of the unlabelled labelling probes (or first polynucleotides) and/or the reporter probes (or second polynucleotides).

In performing the sequence detection method, firstly, the test polynucleotide should be isolated and prepared for sequencing. More than one type of test polynucleotide may be present where multiplexing is to be used. Optionally, the polynucleotide (e.g. genomic DNA) obtained from a sample may be amplified as described hereinbefore to provide amplicons containing the target sequence suitable for use in the method. Primers may be appropriately selected to provide an amplicon containing the target sequence. Multiple primers may be used if multiple test polynucleotides and/or multiple target sequences are to be used. Forward and reverse primers may be used. Conveniently the amplicon is from 50-5000 nucleotides in length, e.g. 50-1500, such as 100-500 nucleotides in length.

After PCR, a nuclease, which degrades single stranded polynucleotides but not double stranded extension products (e.g. exonuclease 1) and a phosphatase (e.g. as described hereinbefore) may be added to degrade the PCR primers and dNTPs that have been used in the reaction. These enzymes then need to be treated to achieve their inactivation before progressing to the next step, e.g. treatment at 85° C.

The labelled ddNTP(s) and unlabelled labelling probe(s) (or first polynucleotide(s)) are brought into contact with the test polynucleotide(s) and a polymerase under conditions allowing the incorporation of the ddNTP when the target sequence is present. As mentioned hereinbefore these components may be added together, at different times, or in various combinations. When multiplexing is to be performed, the various ddNTPs and/or unlabelled labelling probes may also be added together, or sequentially, or in various combinations. The conditions allow binding of the unlabelled labelling probe (or first polynucleotide) to the target sequence, when present, and for polymerase chain extension to occur.

The method may be performed in the presence of other molecules such as dNTPs. One or more dNTPs may be used (e.g. dATP and dCTP). In methods of this type chain extension will occur until the relevant ddNTP is incorporated which will prevent further extension. In such methods one may add the ddNTP of interest and other dNTPs to provide complementary bases for all possible nucleotides (e.g. ddATP, dTTP, dCTP and dGTP). Unlabelled ddNTPs may also be used, e.g. for ddNTPs other than the labelled ddNTP. This prevents misincorporation of the labelled ddNTP where complementarity does not exist. This can also be achieved using a labelling probe with a discrete number of mismatches to the target sequence such that further mismatching is less likely to be tolerated. These mechanisms aid specificity in the method.

Conveniently, multiple cycles of ddNTP labelling may be performed to maximize the labelling that is achieved (i.e. to improve sensitivity). For example, after a first round of labelling is performed, the reaction may be heated to provide single stranded molecules, and then cooled to allow hybridization and repeat of the labelling step. Conveniently between 1 and 50 cycles are used, e.g. from 1 to 20, such as from 5-20 cycles.

Depending on how the method is to be performed, once covalent binding has been achieved, the complexes may be washed to remove unbound bases and/or other polynucleotides particularly if they carry the label whose signal is to be detected which would otherwise result in high background readings. This may be achieved where, for example, the labelling probe (or first polynucleotide) carries a moiety that may be used for affinity binding, e.g. a binding partner of a binding pair where the other pair is on a solid support. However, the present method conveniently allows the full method to be achieved in solution and for subsequent method steps to be carried out in the presence of the reagents of former steps. In a preferred aspect the method is carried out in solution without the need for the participating molecules to be bound to a solid support.

Following this step, the labelling probe(s) (or first polynucleotide(s)) (which may be unlabelled or may not carry a label by virtue of incorporation of a labelled ddNTP, is separated from the test polynucleotide(s). Conveniently this is achieved by heating the complexes to cause dissociation.

The resultant single stranded molecules are then contacted with the reporter probe(s) (or second polynucleotide(s)) carrying the second label under conditions allowing the hybridization of the labelling probe(s) (first polynucleotide (s)) to the reporter probe(s) (second polynucleotide(s)). When multiplexing methods are to be used, the different reporter probes (or second polynucleotides) may be added together, separately or in various combinations. The resultant double stranded molecule has ends selected from blunt, 3' protruding or 5' protruding, as described hereinbefore.

To avoid inappropriate incorporation of the ddNTP label, treatment to remove/inactivate/degrade/outcompete the polymerase/ddNTPs/lengthen the single stranded portion as described hereinbefore is performed. This treatment may be performed as soon as the chain extension reaction in which ddNTP is incorporated commences (or during that process). Thus this treatment may commence at the same time as the polymerase reaction to incorporate the ddNTP (providing the polymerase is not immediately inactivated) or may commence during this reaction or immediately follow the step of labelling the labelling probe(s) (first polynucleotide (s)) and/or be carried out during and/or after the hybridization step involving the labelling probe(s) and reporter probe (s) (first and second polynucleotides). Preferably this treatment is performed after the polymerase reaction to incorporate the ddNTP and before the hybridization step/addition of the reporter probe (or second polynucleotide).

Following the treatment/double stranded polynucleotide preparation, analysis is performed to determine whether a reporter probe (second polynucleotide) has bound to a labelled labelling probe (first polynucleotide). The signal generated by the label(s) may be detected at various points during the method. In some cases only a single measurement may be required if that measurement can be compared to control levels of the signal which are indicative of whether or not the first and second polynucleotides have bound to one another (e.g. when quantitative measurements are made). Measurements may be taken before, during and/or after preparation of the double stranded molecule (to assess differences in the signal as the double stranded molecule is formed). Alternatively or additionally, measurements may be taken, before, during and/or after dissociation of the double stranded molecule.

Conveniently, as described above, this may be by use of melting curve analysis. In that case, the signal is detected continuously or periodically during a protocol in which the temperature is increased to cause melting of the double stranded molecule.

In methods in which melting curve analysis is performed, if desired, the melting curve analysis may be repeated by cooling to allow hybridization and repeating the temperature increase to allow dissociation. Whilst, preferably, the treatment (to remove polymerase etc.) is performed before, during and/or immediately after preparation of the double stranded molecule, in one aspect, the treatment may be performed only after a first melting curve analysis, e.g. after a first, but before a second, melting curve analysis. This has some merit in identifying polymerase-dependent false FRET effects (and possibly non-covalent binding of ddNTPs) that may be removed before the second analysis allowing the qualitative and quantitative identification of that false FRET effect (and possibly non-covalent binding), as opposed to covalent ddNTP binding. Control reactions may also be performed by performing the above described methods with or without the above treatments (e.g. with or without a protease) and/or use of internal controls to assess (qualitatively or quantitatively) the extent of false ddNTP binding and/or false FRET effects. For example, if two melting curve analyses are performed (see the examples) and quenching is observed during the first melting curve but is not observed in the second melting curve which is performed after polymerase removal/inactivation/degradation, then the quenching observed in the first melting curve may be attributed to the polymerase-dependent false FRET effect (and possibly some ddNTP non-covalent binding).

If multiplexing is to be performed in a melting curve analysis method, changes in signal (e.g. fluorescence) are monitored from temperatures at least 5° C. below the lowest Tm of any of the possible complexes to at least 5° C. above the highest Tm of any of the possible complexes as the temperature increases. If a fluorophore:quencher label combination is used, and both labels are attached to the same complex such that the quencher affects the fluorophores' signal, during the melting the fluorescence signal with change (increase) as the strands melt apart. This change in signal (e.g. fluorescence) may be monitored, e.g. as described hereinbefore. When multiplexing is used, fluorescence at more than one wavelength may be monitored. The results obtained may conveniently be represented as the derivative of the change of fluorescence with temperature (i.e. derivative fluorescence (−dF/dT)) to allow the Tm to be identified as a peak.

The above method may be performed in cycles if desired to identify more than one target sequence in the test polynucleotide, by using the test polynucleotide in further cycles of the method using different labelling probes and reporter molecules.

The method may conveniently be used for identifying a target sequence in a test polynucleotide. The method may be used to identify one or more unknown nucleotides in a target sequence. This may be achieved, for example, by use of multiple labelling probes (first polynucleotides) each directed to different adjacent sequences (which may be discriminated by using the multiplexing methods described above), e.g. labelling probes whose ends bind within a nucleotide of one another at their 3' end. Alternatively (or additionally), labelling probes which are specific for different possible sequences (but binding at the same site in the target sequence) may be used and their signal identified on the basis of their specific Tm and/or label's signal. Thus, for example, a set of labelling probes may be used in which the 3' terminal nucleotide varies, e.g. XXXXA, XXXXT, XXXXC, XXXXG. These probes may then be used in an extension reaction to determine the identity of the next nucleotide by ddNTP binding. If these labelling probes can be distinguished (either by the label on the reporter probe to which they bind) or the Tm of the complex that is formed, two nucleotides may be sequenced during the method. Thus, one, two, three or more nucleotides may be sequenced/identified in the method using the multiplexing methods described hereinbefore.

Where appropriate, sets of labelling probes may be used in which one or more nucleotides are degenerate if sequence variation is possible but should not impede binding of the probe.

Conveniently the method is used to detect SNPs. Thus, in a preferred aspect, the target nucleotide sequence is a SNP. In a further preferred aspect, at least two target nucleotide sequences are detected in said method, preferably at least two SNPs (e.g. at least 4, 6, 8 or 16 SNPs).

In this case multiplexing is conveniently performed to allow assessment of multiple SNPs in a single assay and/or to assess homozygosity of the SNP. In the latter case, for example, the nucleotide in question may have an adenine or a guanine base. A labelling probe is used and at least two ddNTPs (ddUTP and ddCTP) each carrying a different label are used in the chain extension reaction. The binding of the ddUTP or ddCTP is then assessed based on their signal when the double stranded molecule is generated. If both ddUTP and ddCTP are found to have bound, the genotype is heterozygous for A/G but if only one of ddUTP or ddCTP binds a homozygous AA or GG may be identified.

The method of the invention may be used in any methods in which detection of nucleic acids is required, e.g. in diagnosis, detection of infections or contaminating organisms or pathogens, clinical monitoring, forensics, food and environmental safety and monitoring, for distinguishing between different cells types, mutation detection analysis of polymorphism, e g. in tissue typing and as a general molecular biology tool.

The method finds particular application in methods in which one or more SNPs are to be detected quickly and efficiently. SNP analysis has a series of diagnostic applications such as testing for genetic predisposition to disease in humans, animals and plants, as markers associated with breeding parameters and for detection, typing and quantification of microbes in biological and environmental samples. The method may conveniently be used in methods of diagnosis or genotyping. By way of example, the method may be used to identify important genetic markers, e.g. to identify a propensity for, or risk of, disease. For example genetic markers of relevance to salmon breeding may be assessed. There are currently no technologies that can efficiently and inexpensively fulfil the breeding-related pre-screening needs involving a relatively low number (<100) of SNPs in a very large number of individuals (>100,000 per year). Methods of the invention may be used to identify SNPs in individuals to determine pedigree and the presence of important breeding traits (e.g. IPN resistance).

Heterozygous states may also be assessed as discussed above. The method may also be used diagnostically, e.g. to diagnose Irritable Bowel Syndrome (IBS) by examining microbial markers. Up to 60 SNPs may be evaluated simultaneously.

Thus in a preferred aspect the method may be used to detect SNPs, in particular it may be used to diagnose IBS where more than one bacterium is causative by identifying SNP markers for those bacteria. Thus in a further preferred aspect, the present method provides a method of diagnosing Irritable Bowel Syndrome, comprising a method as described herein before, wherein preferably at least two SNPs are detected in said method.

The method may also be used in genotyping. Thus, in a further preferred aspect the present invention provides a method of genotyping an organism, comprising a method as described hereinbefore, wherein preferably at least two SNPs are detected in said method.

FIG. 1 provides an overview of a preferred method of the invention in which the method is used to identified the presence of two SNPs in a test polynucleotide (after amplification) (see FIG. 1B) or the identify the SNP allele (see FIG. 1C). The methods described in the Examples form further preferred aspects of the invention.

All combinations of the preferred features described above are contemplated, particularly as described in the Examples. The invention will now be described by way of a non-limiting Examples with reference to the drawings in which:

FIG. 1 shows an overview of Liquid Array Diagnostics (LAD) technology for SNP typing. (A) Main steps of LAD. (B) Application of LAD for SNP typing to identify/quantify bacterial species. (C) Application of LAD for SNP-typing in non-haploid species.

FIG. 2 provides a demonstration of non-template-, polymerase-dependent quenching. The complementary RP 2_1_in1bFAMRevComp is quenched by unlabelled labelling probe in the presence of $ddCTP^{TAMRA}$ and HOT TERMIPol.

FIG. 3 shows that removal of $ddCTP^{TAMRA}$ and/or HOT TERMIPol by chloroform extraction alleviates the non-template-dependent false-positive quenching phenomenon. The same "+ polymerase" samples shown in FIG. 2 were dissociated anew, following chloroform extraction. Note the apparent Tm shift in the quenching response.

Figure 6:
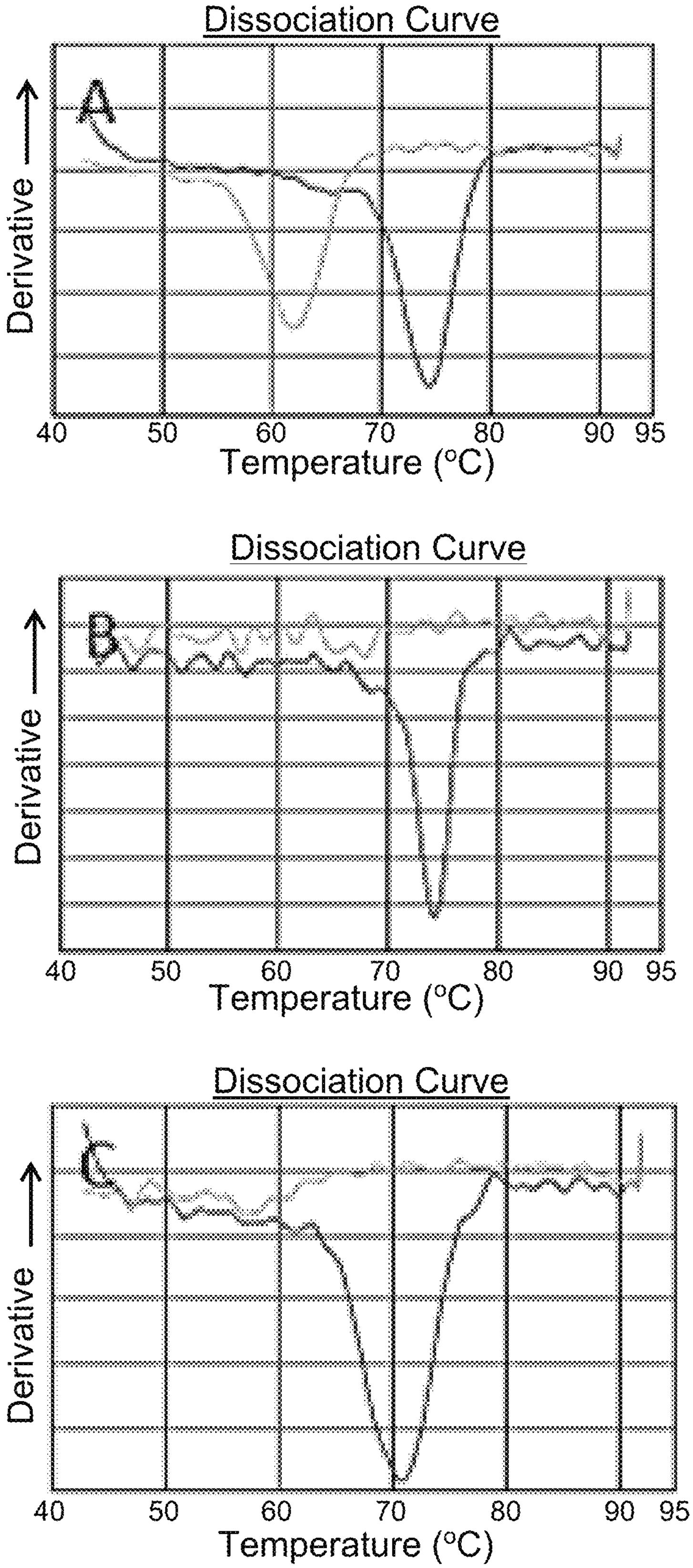
Figure 6:
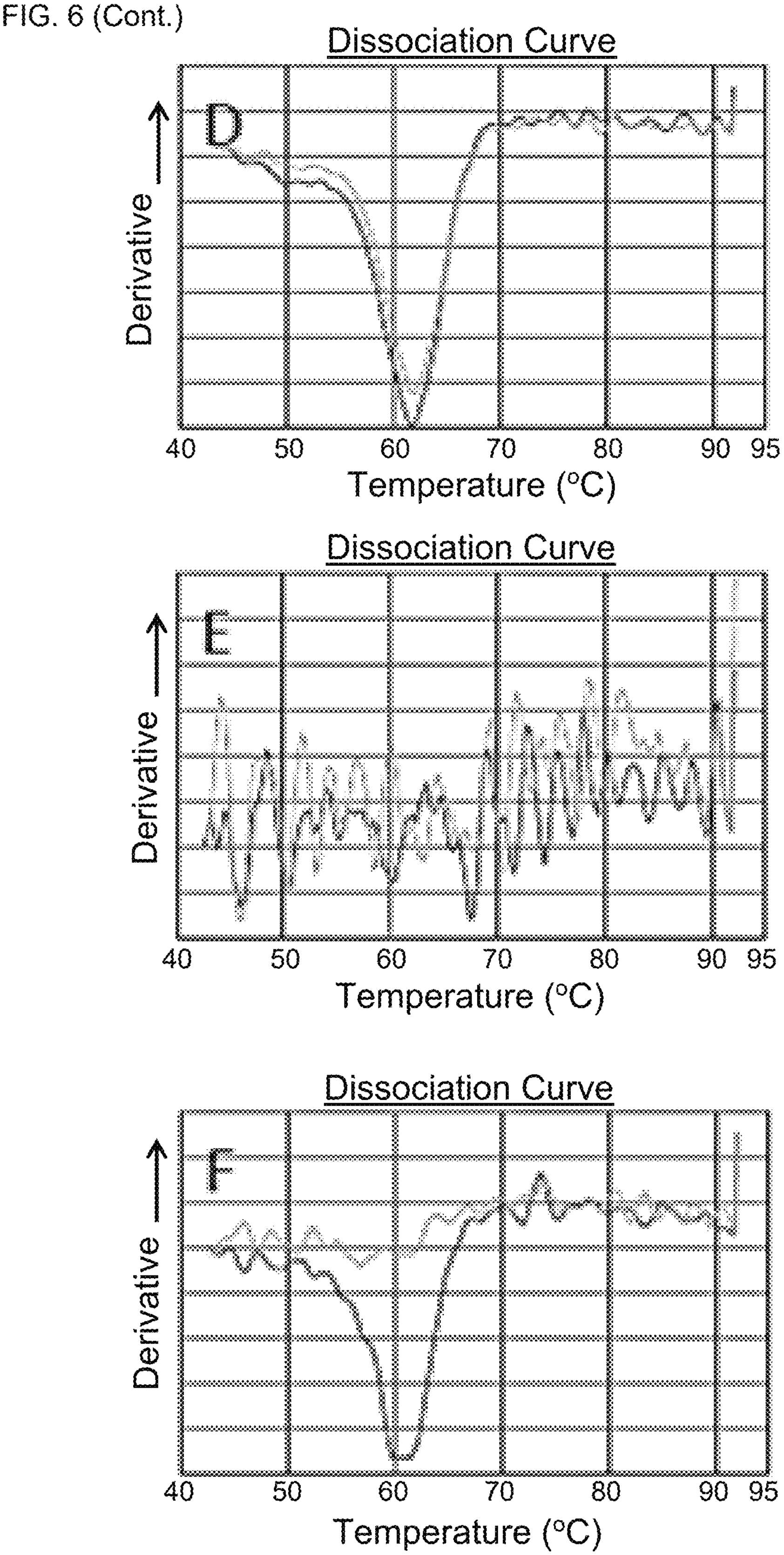

FIG. 6 provides an indication of a terminal transferase-like activity for HOT TERMIPol. (A)-(C). Three LP-RP duplexes were combined in the presence of HOT TERMIPol, $ddCTP^{TAMRA}$ in the presence (lighter curves), or absence (darker curves) of proteinase K. (D)-(F). The proteinase K-untreated samples from A-C were treated with proteinase K and all samples were subject to a second dissociation. A and D contain the duplex Faecali LP/Faecali RevComp+1 FAM that forms a blunt end on one side and a protruding 5' FAM-G on the other; B and E contain the dual blunted-ended duplex 2_1 LP/2_1_in1bFAMRevComp; C and F contain the dual blunted-ended duplex Faecali LP/Faecali RevComp FAM.

Figure 7:
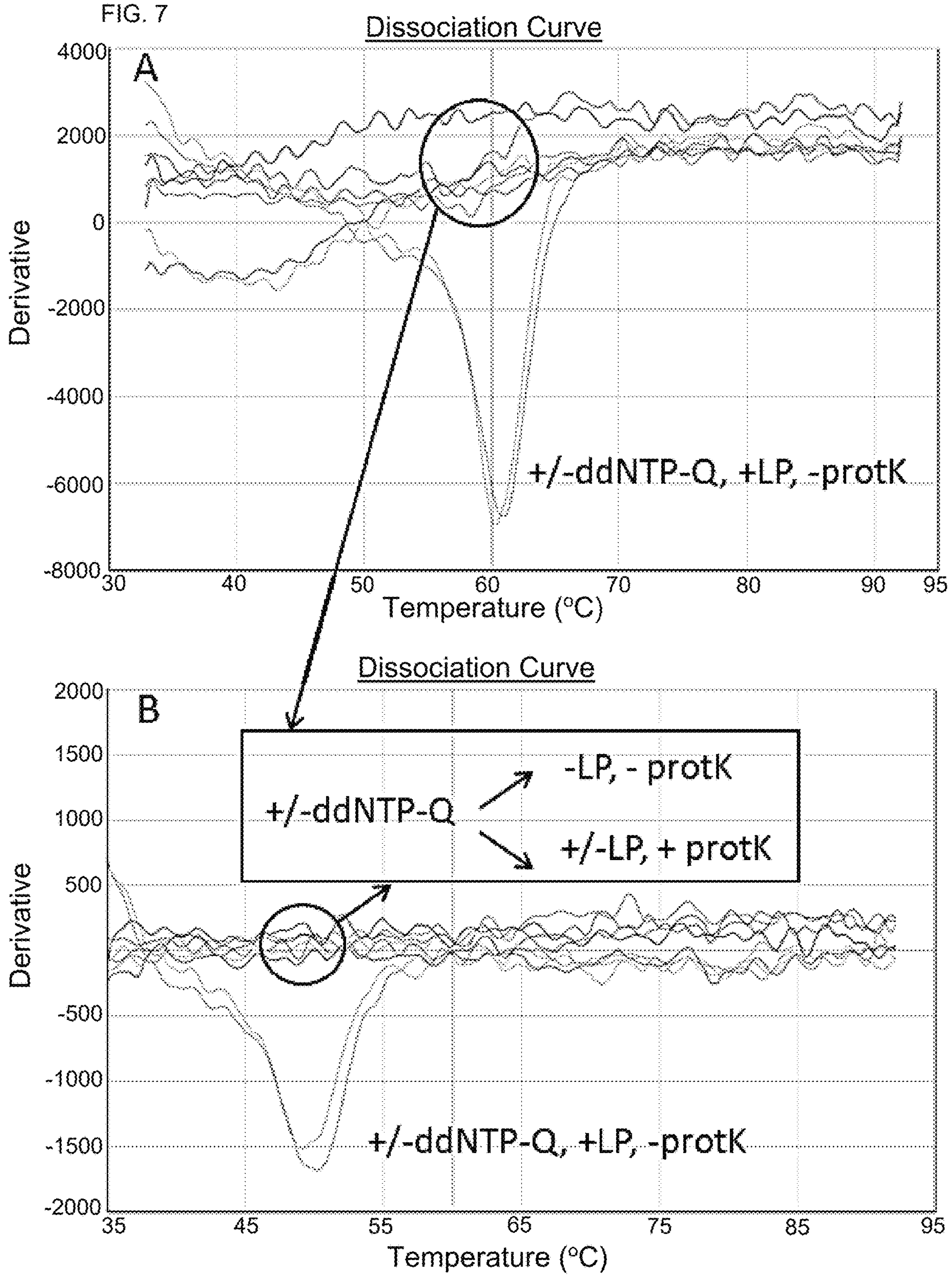

FIG. 7 shows the false FRET effect is dependent on active polymerase alone, and does not require ddNTP-Quencher. Mock labelling reactions all lacking template and harbouring all combinations of +/−LP, +/−ddUTP-ATTO540Q were first incubated at 95° C. for 10 minutes to activate the Hot TERMIpol DNA polymerase. Each reaction was then split in two; proteinase K (in 1× Buffer C) was added to one set at a final concentration of 58 μg/mL, and the other set received an identical volume of 1× Buffer C. Both sample sets were incubated at 56° C. for 30 min. prior to generating melting curves from 30° C. to 95° C. (A) the FAM-labelled RP C313Y RP (U)FAM showed a quenching response in samples containing its complementary LP C313Y LP (C_U) regardless of the presence or absence of ddNTP-Q, but only those untreated with proteinase K where the polymerase remains active. (B) Similar results were observed on a different fluorescence channel for the HEX-labelled RP nt821 RP (U) HEX and its complementary LP nt821 (del11) LP (U).

FIG. 8 shows SDS treatment is as effective as proteinase K at alleviating the Tm shift. (A) The LP nt821 (del11) LP (U) was first labelled with ddUTP-ATTO540Q in the presence of template and was subsequently incubated at 56° C. in the presence of proteinase K (58 μg/mL in 1× Buffer C), SDS (0.1% in 1× Buffer C), BSA (58 μg/mL in 1× Buffer C), or Untreated (1× Buffer C) prior to the addition of RP nt821 RP (U) HEX and melting curve determination. Both the Untreated and BSA-treated samples that still harbour active Hot TERMIPol DNA polymerase exhibit quenching curves of a higher Tm than the proteinase K- and SDS-treated samples. (B) Similar results were observed for the LP/RP duplex Q204X LP (C_U)/Q204X RP2 (C) ROX.

FIG. 9 shows SDS treatment is as effective as proteinase K at alleviating the false FRET effect. (A) Mock labelling reactions lacking template but harbouring the LP nt821 (del11) LP (U), ddUTP-ATTO540Q were performed in a volume of 50 μL. Four 10 μL aliquots were subsequently incubated at 56° C. in the presence of proteinase K (58 μg/mL in 1× Buffer C), SDS (0.1% in 1× Buffer C), BSA (58 μg/mL in 1× Buffer C), or Untreated (1× Buffer C) prior to the addition of RP nt821 RP (U) HEX and melting curve determination. While the BSA- and 1× Buffer C-treated samples exhibited a temperature-dependent quenching (FRET) effect, both the SDS- and proteinase K-treated samples did not. (B) The same experimental setup was employed as above, this time using the LP/RP duplex E291X LP (C)/E291X RP (C) CY5 and ddCTP-ATTO612Q. Here, the Untreated and BSA-treated samples showed a temperature dependent fluorescence (FRET) effect, while the SDS- and proteinase K-treated samples did not.

FIG. 10 shows hot FIREPol, a "normal" Taq polymerase, also stabilizes LP-RP duplexes, causing a Tm shift. Labelling probes were labelled with ddNTP-Quenchers using the enzyme Terminal deoxynucleotidyl Transferase (TdT; NEB) under standard reaction conditions at 37° C. for 60 min. followed by inactivation of the enzyme at 75° C. for 30 min. Hot FIREPol was then added to each reaction, activated at 95° C. for 10 minutes prior to adding the corresponding RP to a final concentration of 0.1 μM in either 0.1% SDS (in 1×TdT buffer), or in 1×TdT buffer (Untreated). The untreated samples in all panels (A, LP=Q204X LP (C_U) labelled with ddUTP-ATTO540Q; RP=Q204X RP2 (U) FAM), (B, LP=E226X LP (U) labelled with ddUTP-ATTO540Q; RP=E226X RP (U)YY), (C, LP=Q204X LP (C_U) labelled with ddCTP-ATTO612Q; RP=Q204X RP3 (C) ROX), (D, LP=D182N LP (C_U) labelled with ddCTP-ATTO612Q; RP=D182N RP (C) CY5) showed a quenching response at a higher temperature than those treated with SDS (inactivated polymerase).

Figure 11:
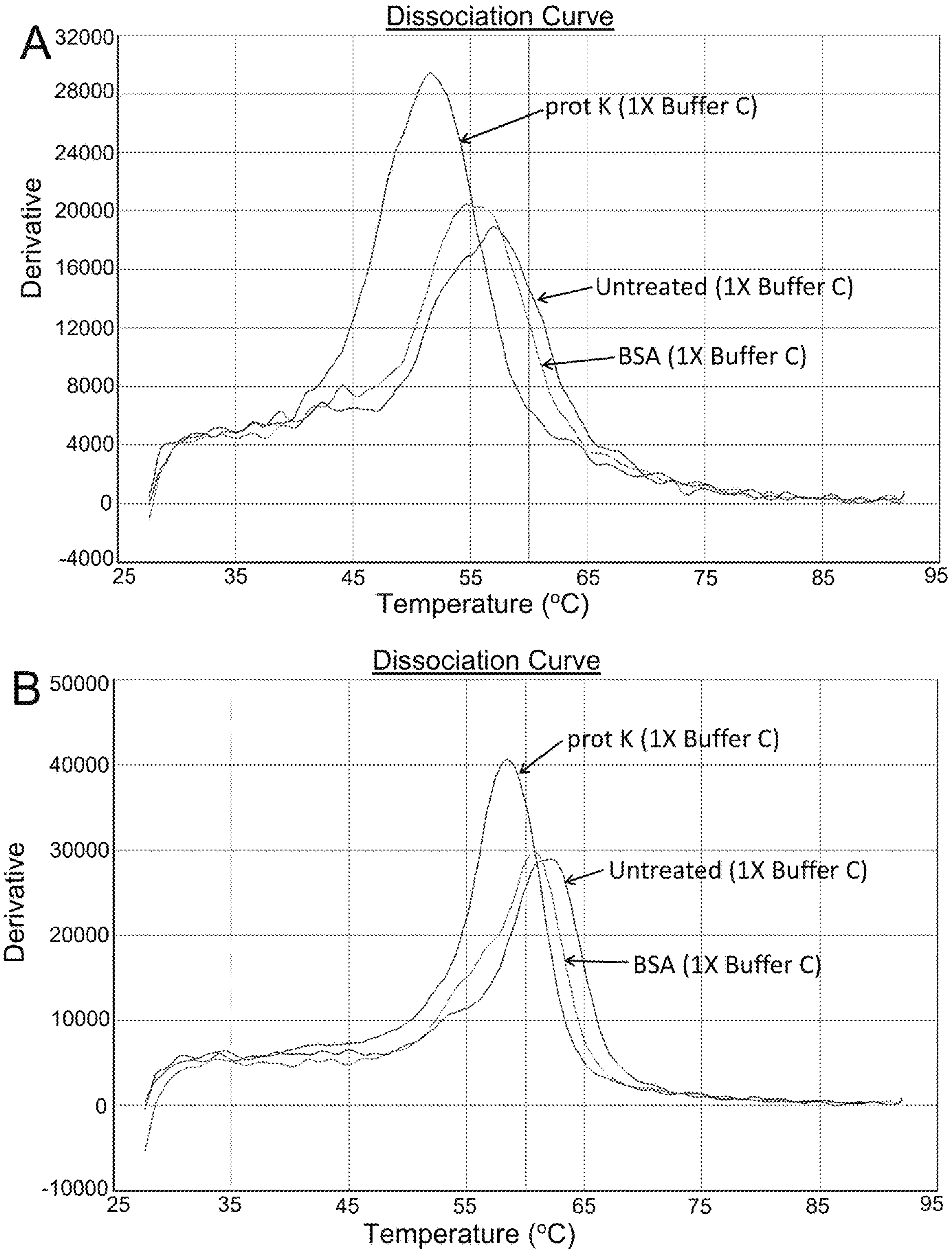

FIG. 11 shows active DNA polymerase also stabilizes unlabelled LP-RP duplexes as detected by the dsDNA-intercalating fluorochrome EvaGreen. Complementary oligo duplexes were combined at a concentration of 0.1 μM in 40 μL (1× Buffer C, 5 U Hot TERMIPol, 1× EvaGreen) and the reactions were split into three aliquots of 10 μL each. Proteinase K, BSA or nothing was added to one of each set of three samples to a concentration of 58 μg/mL (in 1× Buffer C), incubated at 56° C. for 30 minutes prior to melting curve determination. (A) shows results for duplex ASP16/SP60, (B) ASP20/SP60, (C) ASP30/SP60 and (D) ASP60/SP60. For all duplexes, the BSA- and un-treated samples exhibit a dF/dT derivative curve of apparent higher Tm than those in which the polymerase was inactivated by proteinase K, but the Tm shift effects were most pronounced with the shortest duplexes in panels (A) & (B).

Figure 12:
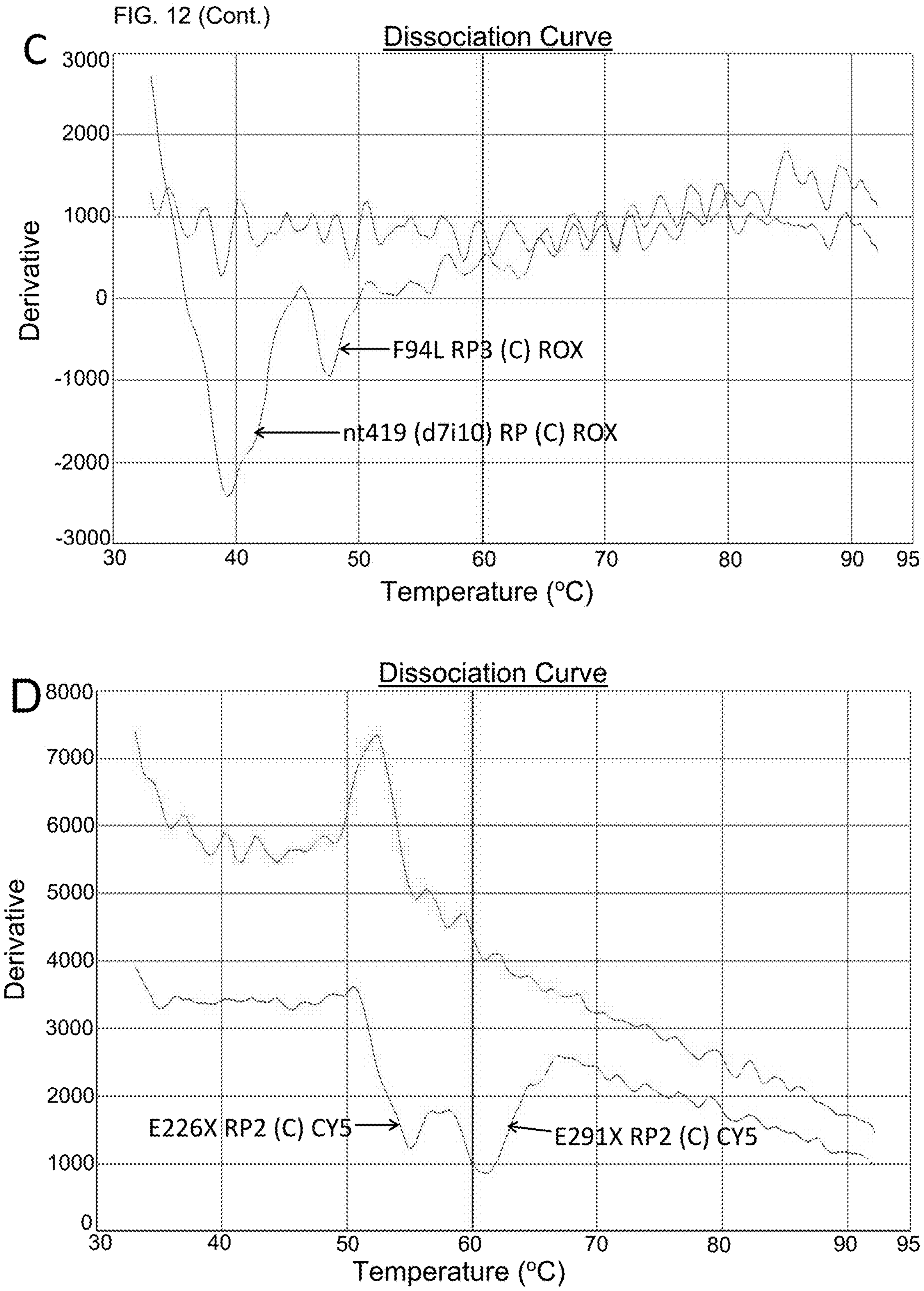

FIG. 12 shows an octoplex LAD assay using 4 channels with 2 melting temperatures per channel successfully distinguishes heterozygotes at four bovine polymorphic loci. Three multiplexed amplicons representing nucleotides 371-480, 2329-2688 and 4787-4976 of the bovine MYOSTATIN gene (Accession number NC_007300 from 6 Jan. 2012) were generated from sequences representing heterozygotes for 3 SNPs and one indel polymorphism. The Exo-SAP-treated amplicons were then used in multiplexed, Hot TERMIPol-based LP-labelling reactions containing both ddUTP-ATTO540Q and ddCTP-ATTO612Q. The corresponding eight RPs labelled with four different fluorochromes were then added to a concentration of 0.1 μM in 0.1% SDS and 1× Buffer C. (A) shows two quenching signals of differing melting temperatures in FAM channel, (B) the corresponding two signals on the Yakima Yellow (YY) channel, similarly for both the ROX channel (C) and the CY5 channel (D), thus providing the correct genotype of a quadruple heterozygote. The no-template negative control (no arrow) shows no quenching signal in any of the panels.

EXAMPLES

Example 1

Materials & Methods

Template Generation for LP Labelling

Plasmids harbouring 16S rDNA sequences from *E. coli* or *Faecalibacterium* spp. were utilised in polymerase chain reactions to generate template for labelling probe (LP) labelling. In brief, 1 μL of a lysate of bacteria harbouring the plasmid clone was added to the following reaction components: 1.25 U HOT FIREPol® DNA polymerase, 1×B2 buffer, 2.5 mM $MgCl_2$ (all from Solis Biodyne, Estonia), 0.1 mM dNTPs (THERMO FISHER SCIENTIFIC™, USA), 0.2 μM HU primer and 0.2 μM HR primer (see Table 3 for primer sequences) in a total volume of 30 μL. PCR amplification was carried out using an APPLIED BIOSYSTEMS™ Veriti™ Thermal Cycler (LIFE TECHNOLOGIES™, USA) and included an initial activation step for 12 minutes at 95° C., followed by 30 cycles of 30 seconds denaturation at 95° C., 30 seconds annealing at 65° C. and elongation at 72° C. for 1 minute and 30 seconds; a final elongation step at 72° C. for 7 minutes was also included. PCR products were visualised under UV illumination following electrophoresis of 5 μL of each reaction on 1% agarose gels containing 1×TAE buffer and 0.6 μg/mL ethidium bromide. To the remaining 25 μL of each reaction, 3 U of Exonuclease I (ExoI; BioLabs Inc., Ipswich, MA, USA) and 8 U of shrimp alkaline phosphatase (USB Corporation, Cleveland, OH, USA) were added prior to incubation at 37° C. for 90 min, 80° C. for 15 min before being placed on ice.

Labelling Primer End-Labelling

Four μL of a dilution series (undiluted, $10^{-1}$, $10^{-2}$, $10^{-3}$ and $10^{-4}$ diluted) Exo-SAP-treated PCR product template (or $H_2O$ as no template control) was added to 16 μl labelling reaction master mix for a total reaction volume of 20 μL [5 U HOT TERMIPol® DNA polymerase, 1× Reaction Buffer C, 1 mM $MgCl_2$ (all from Solis Biodyne), 0.4 μM $ddCTP^{TAMRA}$ (TAMRA-labelled dideoxycytidine triphosphate; Jena Bioscience, Germany) and 0.1 μM LP (Table 3) in DNase/RNase free water]. The thermocycling conditions employed were: initial activation step for 10-12 minutes at 95° C., followed by 10 cycles of 30 seconds denaturation at 96° C., a 1 minute combined annealing and elongation step at 60° C. and a final hold at 10° C.

Melting Curve Analysis

To each LP labelling reaction, 5' fluorescently labelled reporter probe (RP) was added to a final concentration of 0.05-0.1 μM in the presence or absence of proteinase K (final concentration of 25-50 μg/mL). Reactions were placed in a fluorescence-detecting thermocycler (ABI 7500 Fast, APPLIED BIOSYSTEMS™) with the following temperature profile: 56° C. for 30 minutes, 95° C. for 15 seconds, 40° C. for 15 s, 95° C. for 15 s and 60° C. for 15 s. These last four steps comprise the dissociation stage in which fluorescence is detected and expressed in dissociation curves as the derivative (dF/dT) of the fluorescence vs. temperature measurements.

Organic Extraction to Eliminate False Positive Quenching

In one experiment a chloroform extraction (1:1 v/v) was performed on the melting curve reaction after the initial dissociation before performing a secondary dissociation (as described above) to assess the effect of the extraction.

Proteinase K Treatment to Eliminate False Positive Quenching

Initially, proteinase K was added to a final concentration of 25-50 μg/mL simultaneously with the reporter probe prior to dissociation analysis. Later the concentration was raised to 100 μg/mL and treatment with the enzyme was allowed to proceed for 30 minutes at 56° C. prior to the addition of reporter probe. Furthermore, samples subjected to melting curve analysis that had not been treated with proteinase K, were subsequently treated with the enzyme prior to a second dissociation.

Analysis of Terminal Transferase-Like Activity of HOT TERMIPol DNA Polymerase

When testing for interactions between LP-RP duplexes and HOT TERMIPol DNA polymerase in the presence of $ddCTP^{TAMRA}$, the reactions were set up as above with the polymerase in 1× buffer C, the $ddCTP^{TAMRA}$ and $MgCl_2$. These reactions were first subjected to 95° C. for 10-12 minutes to activate the polymerase prior to adding the LP and splitting the reactions in two, one receiving proteinase K (50 μg/mL final concentration) prior to incubation for 30 minutes at 56° C. Corresponding RP's were then added and the reactions were further split in two, one set for dissociation as above and the other for capillary electrophoresis (see below).

Capillary Electrophoresis

To assess potential covalent, HOT TERMIPol-based labelling of oligonucleotides (LP and/or RP) with $ddCTP^{TAMR}$ in the presence or absence of labelling template (ExoSAP-treated PCR product), complementary oligonucleotides or proteinase K treatment, melting curve reactions were first treated with Calf Intestinal Phosphatase (CIP) to remove phosphate groups from unincorporated $ddCTP^{TAMRA}$ before being subject to capillary electrophoresis on an ABI 3130xl Genetic Analyzer (APPLIED BIOSYSTEMS™, USA) using DyeSet G5, with or without a GSLIZ120 size standard, in which the TAMRA label is detected as the yellow (NED) dye of this dyeset.

Results and Discussion

FIG. 1 shows one example of a method using the Liquid Array Diagnostics (LAD) SNP typing technology. Briefly, templates harbouring each SNP are PCR-amplified in multiplex from genomic DNA (for simplicity, FIG. 1 shows only one such template/SNP). Following treatment with Exonuclease I (Exo I) and Shrimp Alkaline Phosphatase (SAP) to remove the PCR primers and dNTPs, respectively, the PCR product is used as a template in a single nucleotide extension reaction using quencher-labelled ddNTPs complementary to the SNP variants to label a labelling probe (LP) that anneals to the template with its 3'-end immediately adjacent to the SNP. To assay LP-labelling, a complementary, 5' fluorescently-labelled reporter probe (RP) is added, and a melting curve analysis is performed; temperature-dependent and fluorochrome-specific quenching indicates LP labelling. This method can be used to type species-specific SNPs to quantify bacterial species present in a sample (FIG. 1B), or to type SNP alleles in non-haploid species (FIG. 1C). Utilizing LP-RP duplexes of varying lengths (Tm's) for each of several fluorochrome detection channels increases the degree of multiplexing, allowing the typing of 20-30 SNPs per sample.

False Positive Quenching and its Alleviation

Figure 2:
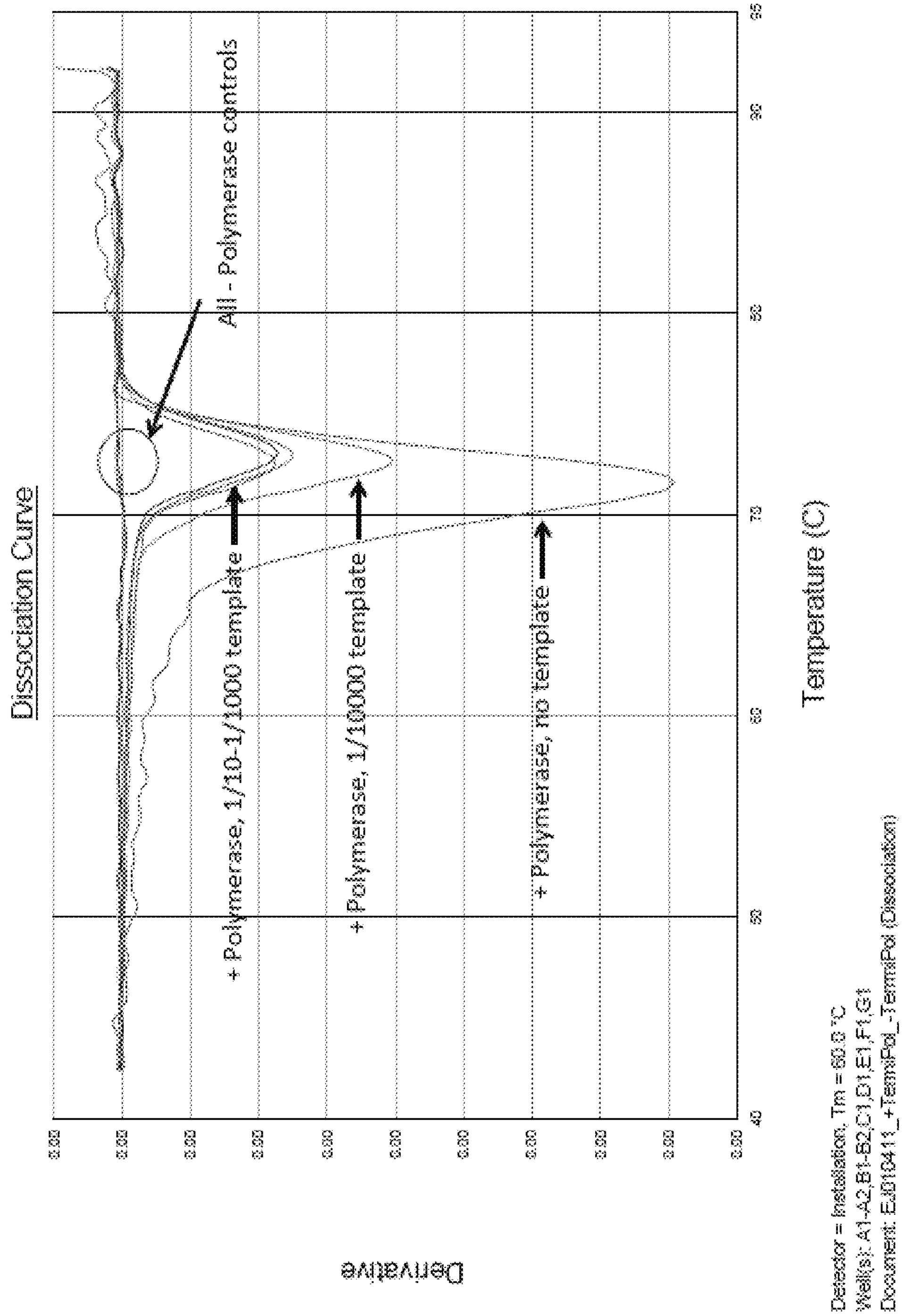
Figure 3:
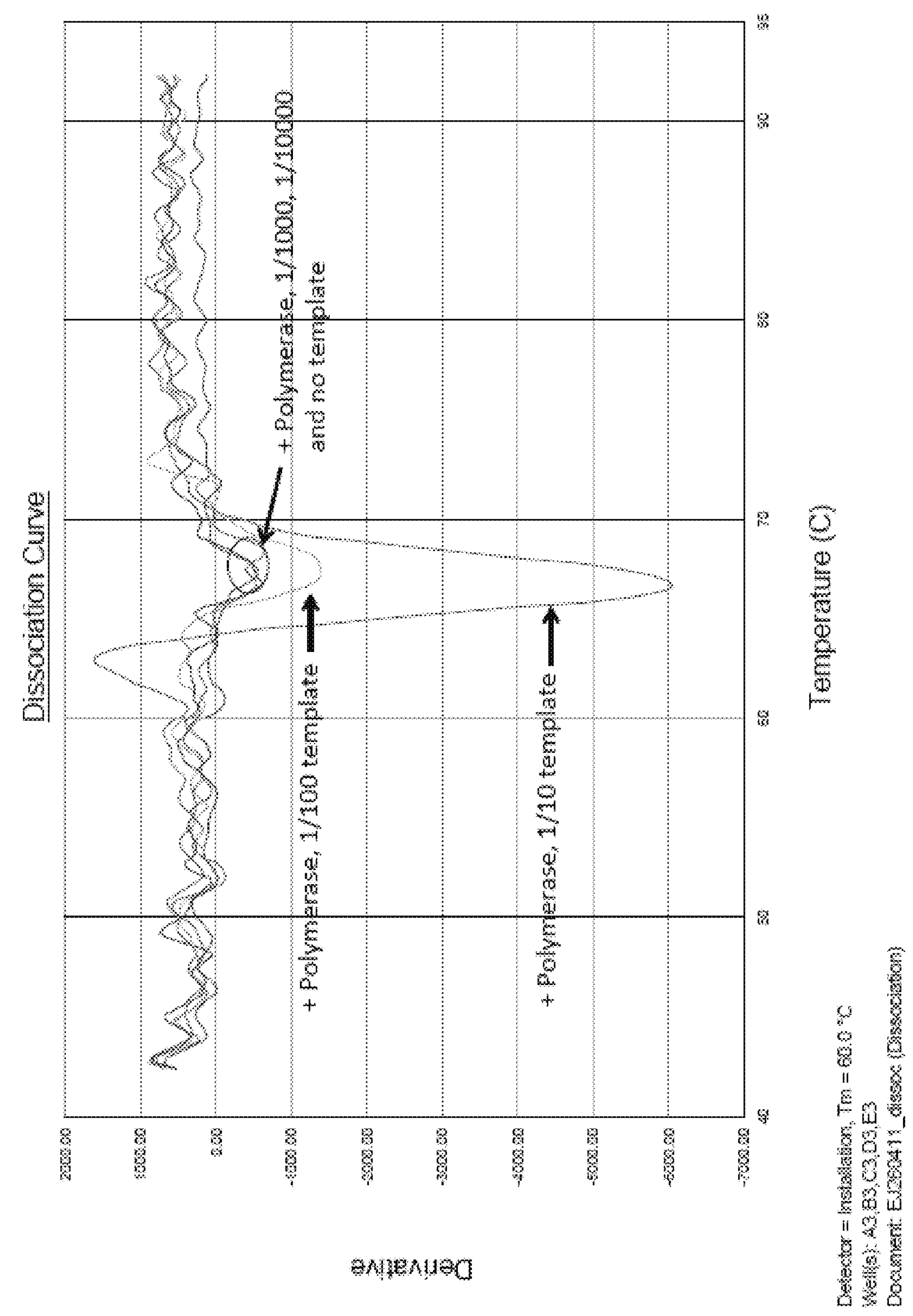

Our initial experiments developing the technology to quantify the presence of bacterial species involved the amplification of 16S rDNA sequences for use as template to end-label species-specific LPs adjacent to a G on the template strand. These experiments utilized lysates of transformants harbouring plasmids containing 16S rDNA sequences from *E. coli* and *Faecalibacterium* spp., and plasmid-specific PCR primers (HU and HR; see Table 3) were employed to avoid amplification of bacterial host sequences. As shown in FIG. 2, we unexpectedly observed an inverse relationship between template quantity and the quenching response, with the "no template" control yielding the greatest degree of quenching. Furthermore, regardless of template concentration, all quenching responses required the presence of the polymerase. LP-RP primer duplexes were designed such that labelling of the LP would create a 3' $ddCTP^{TAMRA}$ protrusion close to the reporter label when duplexed with its respective RP; thus duplexes of unlabelled LP with RP would form blunt ends (both ends) such that no RP-directed, false-positive primer extension could occur by the still-active polymerase during melting curve analysis. With a view to testing whether the polymerase was binding both to the unlabelled-LP-RP duplex and the $ddCTP^{TAMRA}$, thus tethering the quencher near the reporter fluorochrome, we performed a simple chloroform extraction of the quenching-positive samples from FIG. 2. As shown in FIG. 3, the organic extraction apparently alleviated the false positive quenching phenomenon, revealing a template dose-dependent quenching response, although the Tm of the quenching response was reduced from ca. 72° C. before organic extraction (FIG. 2) to ca. 66° C. after (FIG. 3). Chloroform likely partitions the $ddCTP^{TAMRA}$ to the organic phase due to the hydrophobic nature of the TAMRA label; some of the polymerase may have also become similarly partitioned. This result may also be explained by the false FRET effect resulting directly from the polymerase.

Figure 4:
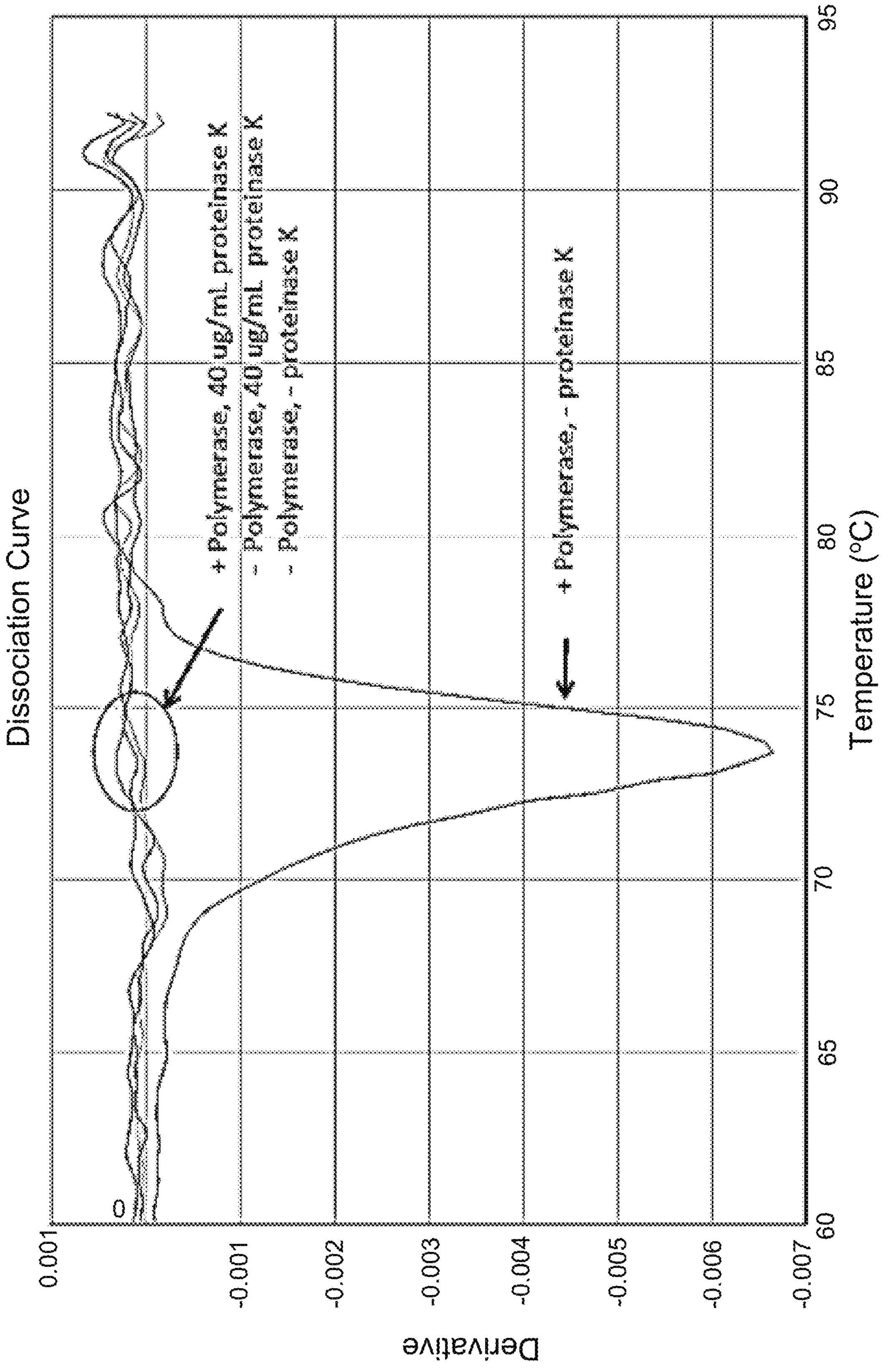
FIG. 4 shows that Proteinase K also alleviates false positive quenching. Quenching of RP 2_1_in1bFAMRev Comp occurs in the presence of unlabelled complementary LP 2_1 LP in the presence of HOT TERMIPol in the absence of proteinase K.

As an alternative to organic extraction, in line with the observation that the false positive effect was entirely polymerase-dependent, we chose to test whether including a proteinase K step to inactivate the polymerase could replace the chloroform extraction. The 2_1 LP and 2_1_in1bFAMRevComp RP (see Table 3 for sequences) were combined in the presence of $ddCTP^{TAMRA}$ and in the presence/absence of both the HOT TERMIPol DNA polymerase and proteinase K. To allow proteinase K to inactivate the polymerase, a 30 minute incubation at 56° C. was included after polymerase activation but prior to melting curve generation. Only the sample harbouring the polymerase without proteinase K showed a quenching response (FIG. 4). No false positive quenching was observed in samples either lacking the polymerase or after having been treated with proteinase K.

Figure 5:
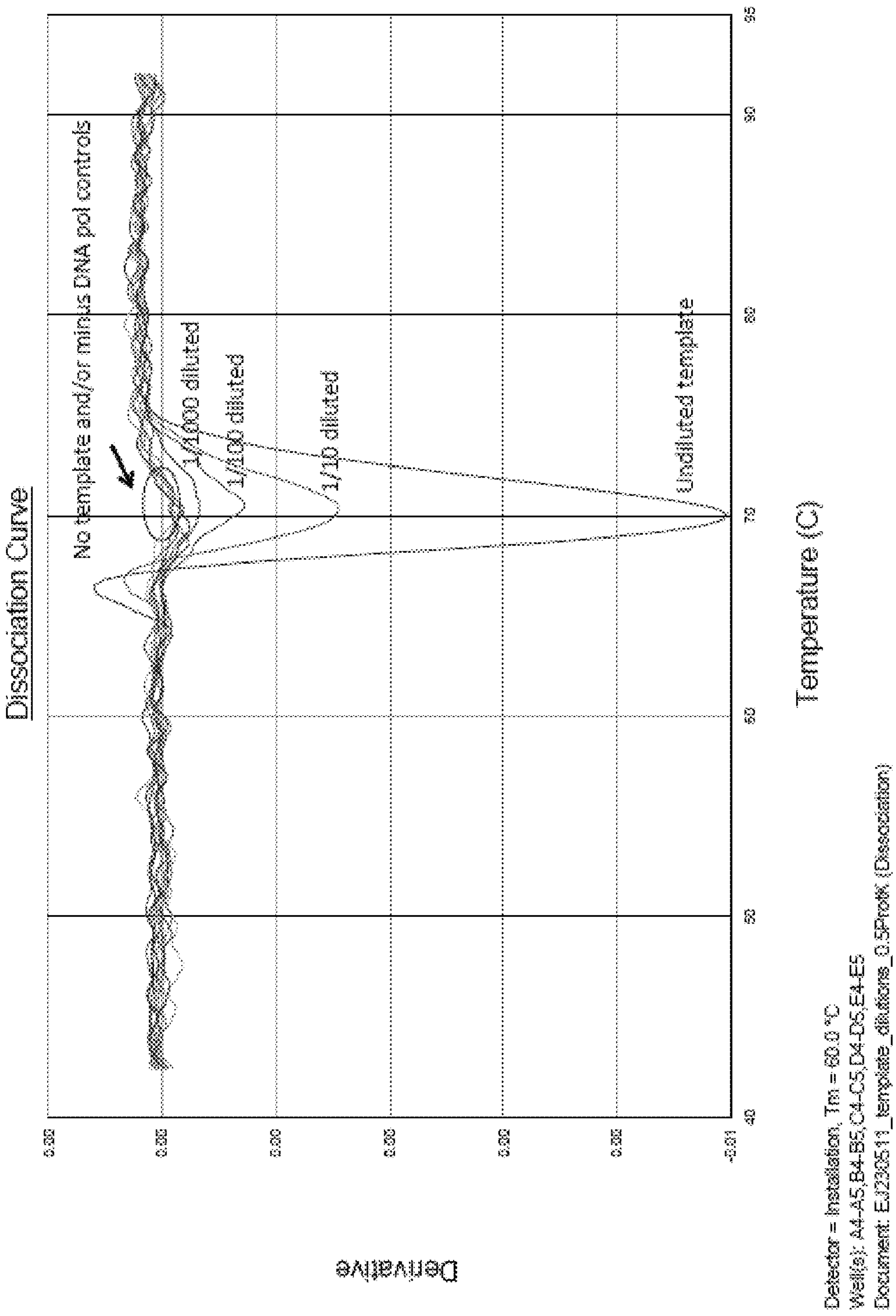
FIG. 5 shows LAD technology incorporating proteinase K treatment and demonstrates a dose-dependent, template-based quenching response.

Using the proteinase K treatment to avoid the false positive effect, we then performed a new test of our LAD method. FIG. 5 shows that when proteinase K treatment is included prior to LP-RP dissociation, the LAD method exhibits a template-dose-dependent labelling of the labelling probe yielding the corresponding differential quenching response; control samples lacking template or DNA polymerase showed no quenching, as expected.

False Positive Quenching Appears to Involve a Terminal Transferase-Like Activity Although inclusion of a proteinase K treatment to inactivate the polymerase alleviated the false positive effect allowing our LAD method to perform successfully, we wished to explore the mechanism underlying the false positive effect to provide information effecting LP-RP probe duplex design parameters. To address whether the mechanism underlying the false positive effect possibly involved a covalent addition of the ddCTP$^{TAMRA}$, the following experiment was performed. Two pairs of LP-RP duplexes (2_1 LP/2_1_in1bFAMRevComp RP and Faecali LP/Faecali RevComp FAM), each forming double blunt ends and a third in which the RP forms a 5'-FAM-G overhang at one end when duplexed with its complementary LP (Faecali LP/Faecali RevComp+1 FAM) were each placed in a reaction mix containing activated HOT TERMIPol DNA polymerase, ddCTP$^{TAMRA}$, buffer/$MgCl_2$, with and without proteinase K. Samples were first incubated at 56° C. for 30 minutes, then subjected to melting curve analysis. The proteinase K-untreated samples were then treated with proteinase K before both sets of samples were dissociated once again. The first two double blunt ended duplexes represent those employed in LAD, while the third having a 5'-protruding G was thought to function as a positive control for polymerase primer extension activity as the ddCTP$^{TAMRA}$ should be incorporated opposite this residue due to the enzyme's 5'→3' polymerase activity.

FIG. 6 and Table 4 summarise the results of these experiments. As shown in FIG. 6 A-C (darker curves with peaks at >70° C.), all three duplexes exhibit a quenching response when untreated with proteinase K. In addition, the positive control duplex (duplex 3 in Table 4, harbouring the 5'-G overhang) also showed quenching in the proteinase K-treated sample (lighter curve in FIG. 6A with peak at <70° C.), whereas the other duplexes treated with proteinase K did not (lighter curves not showing peaks, FIGS. 6B and C; duplexes 1 and 2 in Table 4). The second dissociation following proteinase K treatment of the previously untreated samples revealed expected results for the positive control duplex 3, namely that both samples exhibited a quenching response (FIG. 6D), although the non-proteinase K-treated first dissociation sample now showed quenching with a reduced Tm similar to that of the previously proteinase K-treated sample from the first dissociation. Neither of the 2_1 LP/RP double blunt ended duplex 1 (Table 4) samples showed quenching (FIGS. 6B and 6E) while the Faecali LP/RP double blunt ended duplex 2 (Table 4) sample that had showed quenching during the first dissociation (when untreated with proteinase K; FIG. 6C) continued to exhibit a significant, albeit reduced, quenching during the second dissociation following proteinase K treatment, also here with an apparent reduction in Tm (FIG. 6F).

Results for the positive control duplex indicate that the proteinase K-treatment prior to the first dissociation was not sufficient to inhibit polymerase-directed LP extension with ddCTP$^{TAMRA}$, while its eventual inactivation by proteinase K in both samples lead to an apparent lowered Tm of the quenching response. The fact that neither of the 2_1 double blunt ended duplex samples showed quenching in FIG. 6E indicates that this duplex was not covalently modified with ddCTP$^{TAMRA}$ by the polymerase and that another mechanism underlies the quenching observed in the first dissociation of this duplex (FIG. 6B). Results for the double blunt ended duplex 2 (Faecali LP/Faecali RevComp FAM) suggests that, in the absence of proteinase K treatment, the polymerase was capable of a non-template-dependent addition of ddCTP$^{TAMRA}$ to one or both 3' ends of the duplex. These results point to several effects of the Thermosequenase-like HOT TERMIPol DNA polymerase on duplexes in the presence of ddCTP$^{TAMRA}$ The polymerase may harbour a terminal transferase activity that can add ddCTP$^{TAMRA}$ to selected blunt ended duplexes, but not others, perhaps indicating an end-sequence specificity or preference of this activity. (it is known that selected DNA polymerases, some of which are thermostable, are capable of exercising a template-independent polymerase activity, adding a single 3' dAMP to blunt ended duplexes (Clark, 1988k, Nucleic Acids Research, 16:20, p 9677-9686) a fact that has been widely exploited in so-called T/A cloning of PCR amplicons. However, this had not been observed for ddNTPs.)

The polymerase can also, in the presence of ddCTP$^{TAMRA}$, direct a false positive quenching response of a fluorescently labelled RP when in duplex with a complementary, unlabelled LP. Thirdly, the polymerase has an apparent stabilization effect on quenched duplexes, regardless of the nature of ddCTP$^{TAMRA}$ binding/tethering; inactivation of the polymerase reduces the Tm of the quenching response.

These results are unexpected in view of the observations of Clark (1988, supra) who found that blunt ended oligonucleotide duplexes could be efficiently labelled with dATP by a non-template-dependent terminal deoxyribonucleotidyltransferase (TdT)-like activity of thermostable DNA polymerases; similar labelling with dGTP was much less efficient, and nearly undetectable for dTTP and dCTP.

Verification of the TdT-Like Activity of HOT TERMIPol

In the previous experiment, only one of two blunt ended duplexes were labelled by the TdT-like activity, possibly indicating a sequence-context specificity of this activity. Also, the proteinase K was added simultaneously with the reporter probe, allowing for polymerase activity prior to full inactivation by the proteinase K. Detection of the TdT-like activity was also indirect, based on the observation of quenching during melting curve generation. We wished to test the potential HOT TERMIpol-based labelling of a third double blunt-ended LP-RP duplex directly by detecting fluorescence labelling of oligonucleotides by capillary electrophoresis. To determine polymerase-dependency of any such labelling, we treated the reactions containing activated polymerase with proteinase K prior to addition of the RP. The summary of these experiments is shown in Table 5. In the presence of active HOT TERMIPol DNA polymerase (i.e. in the absence of proteinase K treatment), both oligonucleotides of duplex 4 showed template-independent labelling with ddCTP$^{TAMRA}$ and the duplex showed the corresponding false positive quenching and Tm shift responses. It should be noted that the duplex also exhibited a background quenching response even when treated with proteinase K. The 3' end of the LP in this duplex contains two terminal guanine bases that are known harbour intrinsic quenching activity (Marras et al., 2002, Nucleic Acids Research, e122; Seidel et al., 1996, J. Phys. Chem., 100, p 5541-5553).

Alternative Duplex Structures to Circumvent the TdT-Like Activity of HOT TERMIPol We have demonstrated a novel TdT-like activity of HOT TERMIPol DNA polymerase that can add a single ddCTP to the ends of blunt-ended oligonucleotide duplexes. In addition, the evidence supports the ability of active polymerase to, by an unknown mechanism, tether unincorporated ddCTP$^{TAMRA}$ to a duplex harbouring a fluorescent label, thus generating a temperature-dependent quenching response that also shows an increased Tm indicative of a duplex-stabilising effect of the polymerase. This may also result from the direct polymerase-dependent false FRET effects. Collectively, these effects may be overcome by the inclusion of a polymerase inactivation step (by proteinase K treatment) prior to melting curve analysis.

With the aim of reducing some or all of these effects, we evaluated alternative duplex structures containing combinations of 5' non-complementary protruding and/or 3' protruding ends, some of which were labelled with a reporter fluorochrome, and assayed their ddCTP$^{TAMRA}$-labelling and temperature-dependent quenching behaviours in the presence of active or inactive HOT TERMIPol DNA polymerase.

As shown in Table 6, none of the oligonucleotides of duplexes 5-9 that form 5 T protrusions (either one or two T's in the presence or absence of a FAM label), or 3' C or G protrusions become labelled with ddCTP$^{TAMRA}$ in the presence or absence of active DNA polymerase. The presence of a 5' protrusion containing a FAM-labelled T (duplex 5) somewhat reduced the intrinsic double G quenching effect of the unlabelled LP in the absence of active polymerase as compared with that of duplex 4 (Table 5). Extending the distance between these two G bases of the LP and the 5' FAM label in duplex 7 further reduced this effect. In the presence of non-proteinase K-treated, active polymerase, both duplex 5 and 7 showed increased quenching, a combination of the double G effect and the false positive ddCTP$^{TAMRA}$-tethering effect and/or polymerase-dependent false FRET effect in the case of duplex 5 and less so of the former and more of the latter for duplex 7; both exhibited the corresponding Tm shift. Duplex 8 had the FAM-label positioned closer to the two guanines and yielded a correspondingly increased double G quenching effect.

Surprisingly the presence of active polymerase neither increased the quenching via the false positive effect, nor stabilised the duplex significantly as judged by the meagre increase in Tm. This result may indicate that the polymerase exhibits reduced binding at duplex ends harbouring a 5' recess.

Results from Table 6 are consistent with the view that primer duplexes containing an LP with a G-rich 3'-end will have intrinsic quenching properties and the extension of the reporter fluorophore labelled 5' end of the corresponding RP with a base (or two, i.e. T) not complementary to the ddCTP$^{TAMRA}$ label appeared to alleviate this G-mediated quenching effect, but did not seem to affect the false positive quenching effect caused by active polymerase in the presence of the labelled ddCTP as was observed for duplex 8. The differences in false positive quenching behaviour of duplexes may be explained by potential difference in binding efficiencies the active polymerase has for dsDNA end containing a 5' recess vs. a 5' protrusion, even with a base that is non-complementary to the free dideoxynucleoside triphosphate.

We wished to test whether the inclusion of 5' LP-protrusions harbouring a non-complementary base in duplex with RPs containing either similar 5' protrusions or a 5' recess could further reduce the false positive effect. As shown in Table 7, the 3' ends of RPs in duplex with an LP containing a 5' T protrusion unexpectedly became labelled with ddCTP$^{TAMRA}$ in the presence of active polymerase, as verified by capillary electrophoresis (CE). That a similar 3' extension of LPs opposite corresponding 5' RP T-extensions (duplexes 10-12, Table 7 and duplexes 5-7, Table 6) was not observed may indicate a 3'-end-sequence-context specificity for this activity; the presence of a FAM label on these 5' RPs does not appear to account for this discrepancy when considering the results for duplexes 11 (Table 7) and 6 (Table 6). Assessment of the false positive effect of the duplexes in Table 7 was confounded by the background double G effect and the potential for a 3' TAMRA label on the RP exercising intramolecular quenching of the FAM-label on its 5' end. In addition, depletion of unincorporated ddCTP$^{TAMRA}$ due to the 3' RP-labelling might also be expected to reduce false positive quenching by the active polymerase and/or removal of polymerase to avoid the polymerase-dependent false FRET effects. These effects may be most profound in duplex 13, which showed the greatest degree of 3' RP labelling of all the duplexes analysed by CE (data not shown), and in which the distance between the 3'-TAMRA and 5'-FAM moieties in the dually labelled RP is the shortest.

Preliminary Conclusions Regarding Optimal LAD Duplexes and Pre-Dissociation Treatments From the results presented here, especially with regard to the hitherto undocumented TdT-like and non-complementary primer extension activities of the Thermosequence-like HOT TERMIPol DNA polymerase in addition to the false positive and Tm shift effects that occur during duplex dissociation irrespective of these activities, we can summarise important characteristics for optimal LAD duplexes.

1. Unlabelled LPs in duplex with 5' reporter-labelled RPs should generate single-base 5' recesses at both ends. Blunt ends have the potential of becoming labelled by the TdT-like activity of the polymerase (duplexes 2 and 4 in Tables 4 and 5, respectively). Duplexes that contain 5' protrusions complementary to the ddNTP should be avoided as they risk becoming labelled by primer extension activity of the polymerase. Such protrusions should also be avoided even when non-complementary to the ddNTP due to the non-complementary primer extension activity of the polymerase documented herein (duplexes 10-14).
2. LPs can be designed adjacent to either side of an SNP and when possible, they should be designed to avoid guanines at the 3' end to limit their intrinsic quenching effects. Similarly, RPs may be 5'-labelled with a reporter fluorochrome and 5' guanines should be avoided when possible. These are not absolute requirements for the LAD method to work successfully as one measures the difference in temperature-dependent quenching between duplexes in which the LP becomes extended by the quencher-coupled ddNTP vs. those in which the LP remains unlabelled.

It should be noted that primer duplexes harbouring 5' recessed ends will likely also be subject to the false positive and Tm shift effects of the active polymerase regardless of whether the quencher-coupled ddNTP is present or not. The results from duplex 8 suggest that the polymerase may bind 5' recessed dsDNA ends less efficiently than blunt ends or 3' recessed ends, thus abating the false positive and Tm shift effects. These effects may be avoided by inactivating the polymerase with proteinase K treatment prior to RP addition and dissociation (as described above). This may also be used for duplexes with blunt and/or 3' recessed ends, both to alleviate the false positive and Tm shift effects, but also to avoid pre-dissociation duplex labelling by TdT-like or primer extension activities of the polymerase.

Alternative treatments to alleviate the false positive effect may be to treat the post-LP-labelling sample with a phosphatase to inactivate the quencher-coupled ddNTP, or add unlabelled ddNTP to outcompete the quencher-coupled ddNTP as described herein. To abate both the false positive and Tm shift effects, an anti-DNA polymerase antibody that cross-reacts with HOT TERMIPol could added to the samples prior to RP addition and dissociation.

TABLE 3

Primer names and sequences
(fluorescent FAM label indicated at 5' ends).

| Primer name | Sequence (5'-3') | SEQ ID NO: |
|---|---|---|
| 2_1 LP | CAGGTGTAGCGGTGAAATGCGTAGAGAT | 1 |
| 2_1_in1bFAMRevComp | FAM-ATCTCTACGCATTTCACCGCTACACCTG | 2 |
| Faecali LP | CGTAGTTAGCCGTCACTTC | 3 |
| Faecali RevComp +1 FAM | FAM-GGAAGTGACGGCTAACTACG | 4 |
| Faecali RevComp FAM | FAM-GAAGTGACGGCTAACTACG | 5 |
| LAD LP GP2 | GAGCTGGGGTAGCAGG | 6 |
| LAD LP GP2 -1(5') | AGCTGGGGTAGCAGG | 7 |
| LAD LP GP2 5'T | TGAGCTGGGGTAGCAGG | 8 |
| LAD RP1 GP2atda -1 | CTGCTACCCCAGCTC | 9 |
| LAD RP1 GP2atda -1 FAM | FAM-CTGCTACCCCAGCTC | 9 |
| LAD RP1 GP2atda +1T | TCCTGCTACCCCAGCTC | 10 |
| LAD RP1 GP2atda +1T FAM | FAM-TCCTGCTACCCCAGCTC | 10 |
| LAD RP1 GP2atda +2T FAM | FAM-TTCCTGCTACCCCAGCTC | 11 |
| LAD RP1 GP2atda 0 FAM | FAM-CCTGCTACCCCAGCTC | 12 |
| HR | GCTTCCGGCTCGTATGTTGTGTGG | 13 |
| HU | CGCCAGGGTTTTCCCAGTCACGACG | 14 |

TABLE 4

Primer duplexes treated with proteinase K prior to either first or second dissociation (solid circles represent the FAM labels and the stippled circles indicate sites of covalent ddCTP$^{TAMRA}$ labelling that can explain the quenching behaviour observed).

| Duplex | Pairing Alignment | Oligo names | No Prot. K added at 1st dissoc; Prot. K-treat. --> 2nd dissoc. | | Prot. K added at 1st dissoc.; directly to --> 2nd dissoc. | |
|---|---|---|---|---|---|---|
| | | | 1st Dissociation Quenching | 2nd Dissociation Quenching | 1st Dissociation Quenching | 2nd Dissociation Quenching |
| 1 | 5' CAGGTGTAGCGGTGAAATGCGTAGAGAT<br>\|\|\|\|\|\|\|\|\|\|\|\|\|\|\|\|\|\|\|\|\|\|\|\|\|\|\|\|<br>3' GTCCACATCGCCACTTTACGCATCTCTA● | LP: 2_1/<br>RP: 2_1in1bFAM RevComp | Yes | No | No | No |
| 2 | 5' CGTAGTTAGCCGTCACTTC◌<br>\|\|\|\|\|\|\|\|\|\|\|\|\|\|\|\|\|\|\|<br>◌3'GCATCAATCGGCAGTGAAG● | LP: Faecalibact./<br>Rp: Faecalibact RevComp FAM | Yes | Yes<br>(↓Tm shift) | No | No |

TABLE 4-continued

Primer duplexes treated with proteinase K prior to either first or second dissociation (solid circles represent the FAM labels and the stippled circles indicate sites of covalent ddCTP$^{TAMRA}$ labelling that can explain the quenching behaviour observed).

| | | | No Prot. K added at 1st dissoc; Prot. K-treat. --> 2nd dissoc. | | Prot. K added at 1st dissoc.; directly to --> 2nd dissoc. | |
|---|---|---|---|---|---|---|
| Duplex | Pairing Alignment | Oligo names | 1st Dissoci-ation Quenching | 2nd Dissoci-ation Quenching | 1st Dissoci-ation Quenching | 2nd Dissoci-Dation Quenching |
| 3 | 5′ CGTAGTTAGCCGTCACTTC<br>\|\|\|\|\|\|\|\|\|\|\|\|\|\|\|\|\|\|\|<br>3′ GCATCAATCGGCAGTGAAGG | LP: Faecalibact./ RP: Faecalibact RevComp +1 FAM | Yes | Yes (↓Tm shift) | Yes | Yes |

The sequence for oligo 2_1 is set forth in SEQ ID NO: 1; the sequence for oligo 2_1in1bFAM RevComp is set forth in SEQ ID NO: 2; the sequence for oligo Faecalibact. is set forth in SEQ ID NO: 3; the sequence for oligo Faecalibact RevComp FAM is set forth in SEQ ID NO: 5; the sequence for oligo Faecalibact RevComp +1 FAM is set forth in SEQ ID NO: 4.

TABLE 5

Verification of blunt-end labelling of oligonucleotide duplexes by HOT TERMIPol (solid circle represents the FAM label and the strippled circles indicate sites of covalent ddCTP$^{TAMRA}$ labelling that can explain the quenching behaviour observed).

| Duplex | Pairing Alignment | Oligo names | CE-verified labelling with ddCTP$^{TAMRA}$ (- prot. K only) | Dissociation Quenching (+/- prot. K) | | Interpretation |
|---|---|---|---|---|---|---|
| 4 | 5′ GAGCTGGGGTAGCAGG<br>\|\|\|\|\|\|\|\|\|\|\|\|\|\|\|\|<br>3′ CTCGACCCCATCGTCC | LP GP2/ RP1 GP2 atda 0 FAM | Yes | + | +++ | 3' ends of blunt-ended duplex labelled with ddCTP TAMRA by TdT-like activity of polymerase. |
| | | | | - | ++++ (↑Tm) | Quenching in absence of labelling (i.e. + prot. K treatment) is due to double G (LP 3' end) effect. |

The sequence for oligo LP GP2 is set forth in SEQ ID NO: 6; the sequence for RP1 GP2atda 0 FAM is set forth in SEQ ID NO: 12.

TABLE 6

No labelling of 3' protruding ends (solid circles represent the FAM labels).

| Duplex | Pairing Aligment | Oligo names | CE-verified labelling with ddCTP$^{TAMRA}$ (+/- prot. K) | Dissociation Quenching (+/- prot. K) | | Interpretation |
|---|---|---|---|---|---|---|
| 5 | 5′ AGCTGGGGTAGCAGG<br>\|\|\|\|\|\|\|\|\|\|\|\|\|\|\|<br>3′ CTCGACCCCATCGTCCT | LP GP2 -1 (5')/ RP1 GP2atda +1T FAM | No (+/-) | + | ++ | Double G (LP 3'end effect) |
| | | | | - | ++++ (↑Tm) | Combo of Double G (LP 3' end) effect and false positive effect |
| 6 | 5′ AGCTGGGGTAGCAGG<br>\|\|\|\|\|\|\|\|\|\|\|\|\|\|\|<br>3′ CTCGACCCCATCGTCCT | LP GP2 -1 (5')/RP1 GP2atda +1T | No (+/-) | | | N/A |
| 7 | 5′ AGCTGGGGTAGCAGG<br>\|\|\|\|\|\|\|\|\|\|\|\|\|\|<br>3′ CTCGACCCCATCGTC | LP GP2 -1 (5')/ RP1 GP2atda +2T FAM | No (+/-) | + | + | Extra distance to FAM label → Less/no double G (LP 3'end) effect |
| | | | | - | ++++ (↑Tm) | False positive effect |

TABLE 6-continued

| No labelling of 3' protruding ends (solid circles represent the FAM labels). | | | | | |
|---|---|---|---|---|---|
| Duplex | Pairing Aligment | Oligo names | CE-verified labelling with ddCTP$^{TAMRA}$ (+/- prot. K) | Dissociation Quenching (+/- prot. K) | Interpretation |
| 8 | 5' AGCTGCGGTAGCAGG <br>    \|\|\|\|\|\|\|\|\|\|\|\|\|\|\| <br> 3' CTCGACCCCATCGTC ● | LP GP2 -1 (5')/ RP1 GP2 atda -1 FAM | No (+/-) | +    ++++++ <br> -    +++++++ (slight ↑Tm) | Double G (LP 3'end) effect <br> Double G (LP 3'end) effect. Less false positive effect due to less efficient polymerase binding at 5' recessed effect. |
| 9 | 5' AGCTGCGGTAGCAGG <br>    \|\|\|\|\|\|\|\|\|\|\|\|\|\|\| <br> 3' CTCGACCCCATCGTC | LP GP2 -1 (5')/RP1 GP2 atda -1 | No (+/-) | | N/A |

The sequence for oligo LP GP2-1 (5') is set forth in SEQ ID NO: 7; the sequence for oligos RP1 GP2atda +1T FAM is set forth in SEQ ID NO: 10; the sequence for oligo RP1 GP2atda +2T FAM is set forth in SEQ ID NO: 11; the sequence for oligos RP1 GP2atda-1 and RP1 GP2atda-1 FAM is set forth in SEQ ID NO: 9.

TABLE 7

| Non-template-based labelling of 3' recessed ends opposite a 5' protruding, non-complementary base (solid circles represent the FAM labels and the strippled circles indicate sites of covalent ddCTP$^{TAMRA}$ labelling that can explain the quenching behaviour observed). | | | | | |
|---|---|---|---|---|---|
| Duplex | Pairing Aligment | Oligo names | CE-verified labelling with ddCTP$^{TAMRA}$ (+/- prot. K) | Dissociation Quenching (+/- prot. K) | Interpretation |
| 10 | 5' TGASCTGGGGTAGCAGG <br>     \|\|\|\|\|\|\|\|\|\|\|\|\|\|\|\|\| <br> 3' (◌)CTCGACCCCATCGTCCT ● | LP GP2 5'T/ RP1 GP2- atda +1T FAM | Yes (- only) | +    ++ <br> -    +++++ (↑Tm) | Double G (LP 3' end effect) <br> Combo of Double G (LP 3' end) effect and false positive effect despite 3' TAMRA-labelling effect on RP (quenched as ssDNA) and reduced free free ddCTP$^{TAMRA}$ due to this labelling. |
| 11 | 5' TGAGCTGGGGTAGCAGG <br>     \|\|\|\|\|\|\|\|\|\|\|\|\|\|\|\| <br> 3'(◌)CTCGACCCCATCGTCCT● | LP GP2 5'T/ RP1 GP2atda +1T | Yes (- only) | | N/A |
| 12 | 5' TGAGCTGGGGTAGCAGG <br>     \|\|\|\|\|\|\|\|\|\|\|\|\|\|\|\| <br> 3'(◌)CTCGACCCCATCGTCCTT● | LP GP2 5'T/ RP1 GP2atda +2T FAM | Yes (- only) | +    + <br> -    ++++ (↑Tm) | Extra distance to FAM label → Less double G (LP 3'end)effect 3'TAMRA-labelling effect on RP (quenched as ssDNA): reduced false positive effect due to reduced free ddCTP$^{TAMRA}$ as a result of RP labelling. |

TABLE 7-continued

Non-template-based labelling of 3' recessed ends opposite a 5' protruding, non-complementary base (solid circles represent the FAM labels and the strippled circles indicate sites of covalent ddCTP$^{TAMRA}$ labelling that can explain the quenching behaviour observed).

| Duplex | Pairing Aligment | Oligo names | CE-verified labelling with ddCTP$^{TAMRA}$ (+/- prot. K) | Dissociation Quenching (+/- prot. K) | Interpretation |
|---|---|---|---|---|---|
| 13 | 5' TGAGCTGGGGTAGCAGG<br>\|\|\|\|\|\|\|\|\|\|\|\|\|\|\|<br>3' CTCGACCCCATCGTC | LP GP2 5'T/ RP1 GP2 atda -1 FAM | Yes (- only) | + +++++++<br>- ++ | Double G (LP 3' end) effect<br>Reduced false positive effect since free ddCTP$^{TAMRA}$ exhausted during effective RP labelling and less efficient polymerase binding at 5' recessed end. Also 3' TAMRA-labelling effect on shorter RP (quenched as ssDNA): FAM-label also closer to antepenultimate G on RP |
| 14 | 5' TGAGCTGGGGTAGCAGG<br>\|\|\|\|\|\|\|\|\|\|\|\|\|\|\|<br>3' CTCGACCCCATCGTC | LP GP2 5'T/ RP1 GP2 atda -1 | Yes (- only) | | N/A |

The sequence for oligo LP GP2 5'T is set forth in SEQ ID NO: 8; the sequence for oligos RP1 GP2atda +1T and RP1 GP2atda +1T FAM is set forth in SEQ ID NO: 10; the sequence for oligos RP1 GP2atda +2T FAM is set forth in SEQ ID NO: 11; the sequence for oligos RP1 GP2atda-1 FAM is set forth in SEQ ID NO: 9.

Example 2

Materials & Methods

Template Generation for LP Labelling

Plasmids harbouring bovine MYOSTATIN (MSTN) sequences were utilised in polymerase chain reactions to generate template for labelling probe (LP) labelling. In brief, 100 µg plasmid DNA was added to the following reaction components: 1.25 U HOT FIREPol® DNA polymerase, 1×B2 buffer, 1.5 mM MgCl2 (all from Solis Biodyne, Estonia), 0.1 mM dNTPs (THERMO FISHER SCIENTIFIC™, USA), 0.1-0.2 µM sense primer (SP) and 0.1-0.2 µM antisense primer (ASP; see Table 8 for primer sequences) in a total volume of 30 µL. PCR amplification was carried out using an APPLIED BIOSYSTEMS™ Veriti™ Thermal Cycler (LIFE TECHNOLOGIES™, USA) and included an initial activation step for 10 minutes at 95° C., followed by 30 cycles of 30 seconds denaturation at 95° C., 30 seconds annealing at 50-60° C. and elongation at 72° C. for 1 minute and 30 seconds; a final elongation step at 72° C. for 7 minutes was also included. PCR products were visualised under UV illumination following electrophoresis of 5 µL of each reaction on 1% agarose gels containing 1×TAE buffer and 0.6 µg/mL ethidium bromide. To the remaining 25 µL of each reaction, 3 U of Exonuclease I (ExoI; BioLabs Inc., Ipswich, MA, USA) and 8 U of shrimp alkaline phosphatase (USB Corporation, Cleveland, OH, USA) were added prior to incubation at 37° C. for 90 min, 80° C. for 15 min before being placed on ice.

TABLE 8

Primer names and sequences.

| Primerr name | Sequence (5'-3') | SEQ ID NO: |
|---|---|---|
| SP_MSTNgene_371-480 | CTCCTCCACTCCTGGAACTG | 15 |
| ASP_MSTN gene_371-480 | CGTCCTGGCGTGGTAGTC | 16 |
| SP_MSTN gene_2329-2683 | TTATAGCTGATCTTCTAACGCAAGTG | 17 |
| ASP_MSTN gene_2329-2688 | CTGGGAAGGTTACAGCAAGATC | 18 |
| SP_MST gene_4787-4976 | GGAGAGATTTTGGGCTTGATTG | 19 |
| ASP_MSTN gene_4787-476 | TGCACAAGATGGGTATGAGGATAC | 20 |
| ASP60 | TTGTGATGTAGATGGCGGTTAGGACG GCAGTTTTATGGAGGTGGATAGGTCT TTACTCAG | 21 |
| ASP30 | AGTTTTATGGAGGTGGATAGGTCTTT ACTC | 22 |

TABLE 8 -continued

Primer names and sequences.

| Primerr name | Sequence (5'-3') | SEQ ID NO: |
|---|---|---|
| ASP20 | AGTTTTATGGAGGTGGATAG | 23 |
| ASP16 | TTATGGAGGTGGATAG | 24 |
| SP60 | CTGAGTAAAGACCTATCCACCTCCAT AAAACTGCCGTCCTAACCGCCATCTA CATCACAA | 25 |
| D182N LP (C_U) | TTCCAGTATACCTTGTACCGT | 26 |
| D182N RP (C)CY5 | CY5-TTTCGGTACAAGGTATACTGGA AT | 27 |
| C313Y LP (C_U) | GGATACTTTTGCAAAAATACAAATTC A | 28 |
| C313Y RP (U)FAM | FAM-AAuTTGTATTuTTGCAAAAGTA TccT | 29 |
| nt821 (del11} LP (U) | GGGCTTGATTGTGATGAACAC | 30 |
| nt821 RP (U) HEX | HEX-TTTGTTCATCACtATCAA | 31 |
| Q204X LP (C_U) | CCAGGCACTGGTATTTGG | 32 |
| Q204X RP2 (C) ROX | ROX-TTTTTCAAATACtAGTGCCTGG G | 33 |
| E291X LP (C) | CCAATCCCATCCAAAAGCTT | 34 |
| E291X RP (C) CY5 | CY5-TTTAGcTuTTGGATGGGATTGG A | 35 |
| F94L LP (C) | CTGGAACTGATTGATCAGTT | 36 |
| F94L RP (C) ROX | ROX-TTTACTGATCAATCAGTTCCAG G | 37 |
| E226X LP (C) | CCATTCTCATCTAAAGCTTTGATTT | 38 |
| E226X RP (C) CY5 | CY5-AATCAAA3CTTTAGATGAGAAT GGC | 39 |
| E226X LP (U) | CTGAATCCAACTTAGGCATT | 40 |
| E226X RP (U)YY | YY-ATGCCTAAGcTGGATTCAGG | 41 |
| E291X LP (U) | GTTACCCTCTAACTGTGGATTTT | 42 |
| E291X RP (U)YY | YY-AAATcCAcAGTTAGAGGGTAAcG | 43 |
| F94L LP (U) | GGCATCTCTCTGGACATC | 44 |
| F94L RP (U)FAM | FAM-ATGTCCAGAGAGATGCCA | 45 |
| nt419 Wt LP (U) | AGTTTATTGTATTGTATCTTAGAGCT AAA | 46 |
| nt419 RP (U) FAM | FAM-TTTAGCTCTAAGATAG | 47 |
| nt419 (d7l10) LP (C) | GAAAACCCAAATGTTGTTTCTAAG | 48 |
| nt419 (d7l10) RP (C) ROX | ROX-TTTTCTTAGAAACAACATTA | 19 |

Fluorescent FAM, HEX, Yakima Yellow (YY), ROX and CY5 labels of reporter probes are indicated.
Lower case letters may indicate intentional mismatches or modified nucleotides (pdU, pdC or 5Me-C) utilized to achieve good Tm resolution between quenching signals on a given fluorescence channel.

Labelling Primer End-Labelling

Four μL of Exo-SAP-treated PCR product template (or $H_2O$ as no template control) was added to 16 μl labelling reaction master mix for a total reaction volume of 20 μL [5 U HOT TERMIPol® DNA polymerase, 1× Reaction Buffer C, 1 mM MgCl2 (all from Solis Biodyne), 0.4 μM $ddNTP^{QUENCHER}$ (ATTO540Q-labelled dideoxyuridine triphosphate, ATTO612Q-labelled and DYQ660-labelled dideoxycytidine triphosphate; Jena Bioscience, Germany) and 0.1 μM LP (Table 8) in DNase/RNase free water]. The thermocycling conditions employed were: initial activation step for 10-12 minutes at 95° C., followed by 10 cycles of 30 seconds denaturation at 96° C., a 1 minute combined annealing and elongation step at 60° C. and a final hold at 10° C.

Terminal Transferase Labelling

Reactions harbouring 0.1 μM labelling probe, 1×TdT buffer, 0.5 mM $ddNTP^{QUENCHER}$ (ATTO540Q-labelled dideoxyuridine triphosphate, ATTO612Q-labelled and DYQ660-labelled dideoxycytidine triphosphate; Jena Bioscience, Germany), 0.25 mM $CoCl_2$, 0.2 U/μL Terminal (deoxynucleotidyl) Transferase (New England Biosciences) were incubated at 37° C. for 1 hour, and the enzyme was then heat-inactivated at 75° C. for 30 min.

Melting Curve Analysis

Prior to adding reporter probe and performing melting curve analysis, samples were treated with proteinase K (final concentration of 25-58 μg/mL in $H_2O$, 1× Buffer C or 1×TdT buffer), bovine serum albumin (BSA, final concentration of 25-58 μg/mL in $H_2O$, 1× Buffer C or 1×TdT buffer), SDS (final concentration of 0.1-0.25% in $H_2O$, 1× Buffer C or 1×TdT buffer), or simply an identical volume of $H_2O$, 1× Buffer C or 1×TdT buffer was added. Samples were then incubated at 56° C. for 30 min. Reporter probes were then added to a final concentration of 0.025-0.1 μM. Once it had been determined that SDS was as effective as proteinase K in inactivating the polymerase thus alleviating both the Tm shift and false FRET effects, reporter probes were added directly in a solution containing SDS (final concentration of 0.1-0.25% in $H_2O$, 1× Buffer C or 1×TdT buffer). Reactions were then placed in a fluorescence-detecting thermocycler (ABI 7500 Fast, APPLIED BIOSYSTEMS™) with the following temperature profile: 95° C. for 15 seconds, 25-30° C. for 15 s, 95° C. for 15 s and 60° C. for 15 s. These last four steps comprise the dissociation stage in which fluorescence is detected and expressed in dissociation curves as the derivative (dF/dT) of the fluorescence vs. temperature measurements. Samples that contained duplexes where neither oligonucleotide was conjugated to a fluorophore, EvaGreen (Biotium) was added to a final concentration of 1×.

Results & Discussion

The Polymerase-Dependent False FRET Effect is Independent of ddNTP-Quencher

In order to further investigate the possible mechanism underlying the polymerase-dependent false quenching (FRET) effect, we performed mock labelling reactions lacking template and harbouring all combinations of +/−LP (labelling probe), +/−ddUTP-ATTO540Q that were first incubated at 95° C. for 10 minutes to activate the Hot TERMIpol DNA polymerase prior to being split into two equal sets of aliquots. Proteinase K (in 1× Buffer C) was added to one set at a final concentration of 58 μg/mL, and the other set received an identical volume of 1× Buffer C. Both sample sets were incubated at 56° C. for 30 min. prior to generating melting curves from 30° C. to 95° C. The FAM-labelled RP C313Y RP (U)FAM and the HEX-labelled RP nt821 RP (U) HEX showed quenching responses in samples containing their respective complementary LPs, C313Y LP (C_U) and nt821 (del11) LP (U) regardless of the presence or absence of the quencher-labelled ddNTP, but only those untreated with proteinase K where the polymerase remains active (FIG. 7, panels A & B). These results also verify that the polymerase-dependent false FRET effect is not specific to duplexes in which one of the oligonucleotides is labelled with the fluorochrome FAM as it was also observed for those containing HEX (FIG. 7, panel B).

SDS Treatment Alleviates the Tm Shift and False FRET Effects

To find alternative methods to inactivate the polymerase that would not require a separate treatment and incubation step prior to adding the reporter probe(s), SDS was used. Sodium dodecyl sulfate (SDS) is a detergent and powerful protein denaturant that does not significantly affect nucleic acid hybridization at concentrations below 1%. The addition of SDS to a final concentration of 0.1-0.25% to samples harbouring LPs prior to adding RPs and performing melting curve analysis was tested.

FIG. 8 shows that the addition of SDS to 0.1% was as efficient as proteinase K in alleviating the polymerase-based Tm shift effect seen in the negative control reaction treated with non-supplemented 1× buffer C. Another control reaction was included to confirm that addition of extra protein did not contribute to the lower Tm seen in the proteinase K-treated samples. When added at identical concentrations, bovine serum albumin (BSA) did not exhibit the Tm shift observed for samples treated with proteinase K, indicating that the Tm shift is the result of the polymerase-inactivating activity of the proteinase K and not its generic properties as a protein.

When added to unlabelled LPs prior to RP addition and melting curve generation, 0.1% SDS was also as effective as proteinase K in alleviating the false FRET effect seen in the negative control reaction treated with non-supplemented 1× buffer C (FIG. 9). Another control reaction was included to confirm that addition of extra protein did not contribute to the alleviation of false FRET seen in the proteinase K-treated samples. When added at identical concentrations, bovine serum albumin (BSA) showed false FRET and thus did not exhibit this alleviation observed for samples treated with proteinase K, indicating that alleviating false FRET is the result of the polymerase-inactivating activity of the proteinase K and not its generic properties as a protein. It is also of interest to note that for the fluorochrome CY5, the polymerase-based false FRET did not manifest itself as quenching but rather as a temperature-dependent increase in fluorescence, by definition, also a form of FRET (FIG. 9, panel B).

The use of SDS to inactivate the polymerase represents a significant improvement to the LAD method by obviating an extra reagent addition step and the intervening incubation period; the reporter probe(s) may be added simultaneously with the SDS and melting curve determination can be initiated directly.

The Duplex Tm Shift Effect is a Generic Property of DNA Polymerases

Non-Thermosequenase-like DNA polymerases do not incorporate fluorochrome-conjugated ddNTPs into DNA efficiently, so to test the ability of a conventional, PCR-amenable DNA polymerase (e.g. Hot FIREPol) to elicit the duplex-stabilising Tm shift effect observed for Hot TERMIPol, the labelling probes were labelled with quencher-labelled ddNTPs using the heat labile terminal (deoxynucleotidyl) transferase. Once the labelling reaction at 37° C. was complete, the terminal transferase activity was eliminated by incubation at 75° C. for 30 minutes. Hot FIREPol was then added to the reactions, heat activated at 95° C. for 10-12 minutes prior to adding the complementary reporter probe either in a polymerase-inactivating SDS solution or in sample buffer in which the polymerase would remain active.

As shown in FIG. 10, all samples harbouring active DNA polymerase exhibit quenching curves with an increased Tm compared to identical samples in which the polymerase was inactivated. This effect was seen for RPs containing four different fluorochromes (FAM, Yakima Yellow, ROX & CY5) and LPs with two different quenchers (ATTO540Q & ATTO612Q). In addition to having a higher Tm, the width of the quenching curves appears to be much broader in the active-polymerase samples. This appears to be more pronounced for Hot FIREPol (FIG. 10) than for Hot TERMIPol (e.g. FIG. 8). Our interpretation is that the relative widths of the active-polymerase sample quenching curves reflects the relative binding affinity a polymerase has for the duplex. As such, Hot TERMIPol appears to have a higher binding affinity for duplexed DNA, providing a possible explanation for the enhanced ability of Thermosequenase-like polymerases to incorporate ddNTPs with bulky modifications.

The Polymerase-Dependent Duplex Tm Shift Effect does not Require Conjugated Fluorophores In order to verify that the polymerase-dependent Tm shift effect is not a property observed only for duplexes in which both oligonucleotides are conjugated with a fluorophore/quencher, we employed the dsDNA-binding fluorescent dye EvaGreen that only fluoresces when it reversibly intercalates between nucleotide pairs in duplexed DNA. FIG. 11 shows that duplexes 16 and 20 nucleotide pairs length (panels A and B, respectively) exhibit a fluorescence peak of higher Tm in the presence of active polymerase compared with samples in which the polymerase has been inactivated by proteinase K treatment. SDS could not be used to inactivate the polymerase since it abolishes the dsDNA binding ability of EvaGreen (data not shown). The Tm shift is much less pronounced for duplexes 30 and 60 nucleotide pairs in length (FIG. 11, panels C & D). That fluorescence intensity increases with duplex length is expected since longer duplexes have increased numbers of base pairs between which EvaGreen can intercalate. The lower relative fluorescence in active-polymerase samples for the shorter duplexes (FIG. 11, panels A & B) may indicate the polymerase exercising a physical hindrance to EvaGreen binding, or the polymerase quenching EvaGreen fluorescence.

Use of LAD Technology to Genotype 8 Alleles at 2 Tms Across 4 Fluorescent Channels We applied LAD technology to genotype four polymorphisms (three SNPs and one indel) across three amplicon regions of the bovine MYOSTATIN (MSTN) gene, mutations in which are the causative factor in the double-muscling trait. FIG. 12 shows that LAD technology successfully detected all eight alleles in the three amplified regions of the MSTN gene representing an individual heterozygous at all four polymorphic loci. The alleles were detected as two quenched peaks of different Tm in each of four fluorescence detection channels (FIG. 12 panels A-D). No quenching signals were observed in the no-template control samples on any of the fluorescence detection channels (FIG. 12, panels A-D). By increasing the range and number of resolvable Tms per fluorescence channel, and by implementing additional such channels, it is anticipated LAD technology may be used for multiplexed genotyping of up to 60 distinct alleles.

The invention claimed is:

1. A method of identifying a target nucleotide sequence in a test polynucleotide comprising:

(a) contacting said test polynucleotide with a ddNTP and an unlabelled labelling probe, which probe comprises from 5 to 200 nucleotides and hybridizes to said target nucleotide sequence, when present, immediately 5' to a base which is complementary to said ddNTP in said target nucleotide sequence, in the presence of a polymerase, wherein said ddNTP carries a first label and when said target sequence is present in said test polynucleotide said unlabelled labelling probe hybridizes to said test polynucleotide and is extended in the 3' direction by said polymerase to attach said labelled ddNTP to said unlabelled labelling probe to form a labelled labelling probe;

(b) separating the labelling probe which is a first polynucleotide, which may be labelled or unlabelled, from the test polynucleotide;

(c) hybridizing said labelling probe to a reporter probe, which is a second polynucleotide which comprises from 5 to 200 nucleotides and, carries a second label to form a double stranded third polynucleotide, wherein the first or second label is a fluorophore and the other label is a molecule which affects the fluorescence of said fluorophore when in proximity to said fluorophore, wherein said first and second polynucleotides are complementary to one another over 80-100% of the total length of their sequences and wherein when said labelling probe is unlabelled, at the end closest to the second label said double stranded third polynucleotide is (i) blunt ended; (ii) has a protruding 5' end or (iii) has a protruding 3' end, and at the end distal to the second label said double stranded third polynucleotide is (i) blunt ended; (ii) has a protruding 5' end or (iii) has a protruding 3' end, wherein said protruding 3' or 5' end consists of a single stranded region and when said single stranded region provides a 5' protruding sequence it does not contain a base complementary to said ddNTP immediately adjacent to the double stranded region;

(d) avoiding the generation of a false melting temperature for the double stranded third polynucleotide and/or avoiding the generation of false FRET effects by inactivating or degrading said polymerase in the period during the extension in step a) or after step a) and before or during generation of said double stranded third polynucleotide in step c), wherein when said inactivation or degradation is performed during the extension in step a) the polymerase is not immediately inactivated; and (e) determining if said labelling probe carries a first label by assessing the signal associated with the double stranded third polynucleotide, wherein said double stranded third polynucleotide is subject to melting curve analysis in which melting temperature and/or FRET effects are assessed and in which a change in the first or second label's signal during dissociation which occurs during said melting curve analysis is indicative of the presence of said target sequence in said test polynucleotide.

2. The method of claim 1 wherein said first and/or second label is a fluorophore and the other label is a molecule which affects the fluorescence of said fluorophore when in proximity to said fluorophore and/or said labelling probe and/or reporter probe is from 10-100 nucleotides in length.

3. The method of claim 1 wherein said polymerase is inactivated or degraded with proteinase K or SDS.

4. The method of claim 1 wherein said target nucleotide sequence is a single nucleotide polymorphism (SNP).

5. The method of claim 1 wherein at least two target nucleotide sequences are detected in said method.

6. The method of claim 1 wherein at least two ddNTPs which are labelled are used.

7. The method of claim 1 wherein at least two reporter probes and/or labelling probes are used.

8. The method of claim 7 wherein the at least two reporter probe(s) and the at least two labelling probe(s) are hybridized to one another generating at least two double stranded third polynucleotides with different melting temperatures.

9. The method of claim 6 wherein multiple pairs of labels are provided, wherein each pair of labels comprises a first label on a ddNTP and a second label on a reporter probe, and wherein each pair of labels is different from every other pair of labels.

10. The method of claim 1 wherein the reporter probe is labelled at one of the three nucleotides at its 5' end.

11. The method of claim 1 wherein said first or second label is a fluorophore and the other label is a quencher.

12. The method of claim 1 wherein when said single stranded region provides a 5' protruding sequence it does not contain a base complementary to said ddNTP anywhere in said single stranded region.

13. The method of claim 1 wherein said first and second label is a fluorophore.

14. The method of claim 5 wherein at least two SNPs are detected in said method.

15. The method of claim 6 wherein the first labels on the at least two ddNTPs are different.

16. The method of claim 7 wherein the second labels on the at least two reporter probes are different.

17. The method of claim 9 wherein each pair of the multiple pairs of labels contains first and second labels which are different to any first or second label found in any other pair of labels.

18. The method of claim 10 wherein the reporter probe is labelled at the 5' terminus.

* * * * *